US011767361B2

(12) United States Patent
Tschaika

(10) Patent No.: US 11,767,361 B2
(45) Date of Patent: Sep. 26, 2023

(54) METHOD OF TREATING LUNG CANCER

(71) Applicant: Bristol-Myers Squibb Company, Princeton, NJ (US)

(72) Inventor: Marina Tschaika, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 21 days.

(21) Appl. No.: 17/370,791

(22) Filed: Jul. 8, 2021

(65) Prior Publication Data

US 2021/0403569 A1  Dec. 30, 2021

Related U.S. Application Data

(63) Continuation of application No. 16/306,383, filed as application No. PCT/US2017/035808 on Jun. 2, 2017, now abandoned.

(60) Provisional application No. 62/345,463, filed on Jun. 3, 2016.

(51) Int. Cl.
| | | |
|---|---|---|
| *C07K 16/28* | (2006.01) | |
| *A61P 35/00* | (2006.01) | |
| *A61K 39/395* | (2006.01) | |
| *A61K 39/00* | (2006.01) | |

(52) U.S. Cl.
CPC .... *C07K 16/2818* (2013.01); *A61K 39/39558* (2013.01); *A61P 35/00* (2018.01); *C07K 16/2803* (2013.01); *A61K 2039/507* (2013.01); *A61K 2039/545* (2013.01); *C07K 2317/21* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,977,318 A | 11/1999 | Linsley et al. | |
| 6,051,227 A | 4/2000 | Allison et al. | |
| 6,682,736 B1 | 1/2004 | Hanson et al. | |
| 6,808,710 B1 | 10/2004 | Wood et al. | |
| 6,984,720 B1 | 1/2006 | Korman et al. | |
| 7,034,121 B2 | 4/2006 | Carreno et al. | |
| 7,488,802 B2 | 2/2009 | Collins et al. | |
| 7,595,048 B2 | 9/2009 | Honjo et al. | |
| 7,605,238 B2 | 10/2009 | Korman et al. | |
| 7,943,743 B2 | 5/2011 | Korman et al. | |
| 8,008,449 B2 | 8/2011 | Korman et al. | |
| 8,168,179 B2 | 5/2012 | Honjo et al. | |
| 8,168,757 B2 | 5/2012 | Finnefrock et al. | |
| 8,217,149 B2 | 7/2012 | Irving et al. | |
| 8,354,509 B2 | 1/2013 | Carven et al. | |
| 8,609,089 B2 | 12/2013 | Langermann et al. | |
| 8,728,474 B2 | 5/2014 | Honjo et al. | |
| 8,779,105 B2 | 7/2014 | Korman et al. | |
| 8,779,108 B2 | 7/2014 | Queva et al. | |
| 8,900,587 B2 | 12/2014 | Carven et al. | |
| 9,067,999 B1 | 6/2015 | Honjo et al. | |
| 9,073,994 B2 | 7/2015 | Honjo et al. | |
| 9,084,776 B2 | 7/2015 | Korman et al. | |
| 9,212,224 B2 | 12/2015 | Cogswell et al. | |
| 9,358,289 B2 | 6/2016 | Korman et al. | |
| 9,387,247 B2 | 7/2016 | Korman et al. | |
| 9,393,301 B2 | 7/2016 | Honjo et al. | |
| 9,402,899 B2 | 8/2016 | Honjo et al. | |
| 9,439,962 B2 | 9/2016 | Honjo et al. | |
| 9,492,539 B2 | 11/2016 | Korman et al. | |
| 9,492,540 B2 | 11/2016 | Korman et al. | |
| 9,856,320 B2 | 1/2018 | Cogswell et al. | |
| 10,072,082 B2 | 9/2018 | Cogswell et al. | |
| 10,138,299 B2 | 11/2018 | Cogswell et al. | |
| 10,266,594 B1 | 4/2019 | Cogswell et al. | |
| 10,266,595 B2 | 4/2019 | Cogswell et al. | |
| 10,266,596 B1 | 4/2019 | Cogswell et al. | |
| 10,308,714 B2 | 6/2019 | Cogswell et al. | |
| 10,316,090 B2 | 6/2019 | Cogswell et al. | |

(Continued)

FOREIGN PATENT DOCUMENTS

| | | | |
|---|---|---|---|
| WO | WO-2004004771 A1 | 1/2004 | |
| WO | WO-2006121168 A1 | 11/2006 | |

(Continued)

OTHER PUBLICATIONS

Bristol-Meyers Squibb (A Phase 1/2 , Open-label Study of Nivolumab Monotherapy or Nivolumab Combined With Ipilimumab in Subjects With Advanced Metastatic Solid Tumors, Study NCT01928394, posted Aug. 23, 2013; https://www.clinicaltrials.gov/ct2/history/NCT01928394?V_1=View#StudyPageTop).*
Ott et al (J Clin Oncol, vol. 33, No. 15 suppl: 7502).*
Alaoui, L.H., et al., "Lung Cancer: Biology and Treatment Options," Biochimica et Biophysica Acta, 1856(2):189-210, Elsevier Publishing Company, Netherlands (Dec. 2015).
Brahmer., J.R., et al., "Phase I Study of Single-agent Anti-programmed Death-1 (MDX-1106) in Refractory Solid Tumors: Safety, Clinical Activity, Pharmacodynamics, and Immunologic Correlates," Journal of Clinical Oncology 28(19):3167-3175, American Society of Clinical Oncology, United States (Jul. 2010).

(Continued)

*Primary Examiner* — Brian Gangle
(74) *Attorney, Agent, or Firm* — Sterne, Kessler, Goldstein & Fox P.L.L.C.

(57) ABSTRACT

This disclosure provides a method for treating a subject afflicted with a tumor derived from a small cell lung cancer, which method comprises administering to the subject an antibody or an antigen-binding portion thereof that specifically binds to a Programmed Death-1 (PD-1) receptor and inhibits PD-1 activity or the combination of (a) an antibody or an antigen-binding portion thereof that specifically binds to a PD-1 receptor and inhibits PD-1 activity; and (b) an antibody or an antigen-binding portion thereof that specifically binds to a Cytotoxic T-Lymphocyte Antigen-4 (CTLA-4) and inhibits CTLA-4 activity.

15 Claims, 20 Drawing Sheets

(56) References Cited

U.S. PATENT DOCUMENTS

| | | | |
|---|---|---|---|
| 10,316,091 | B2 | 6/2019 | Cogswell et al. |
| 10,323,093 | B2 | 6/2019 | Cogswell et al. |
| 10,441,655 | B2 | 10/2019 | Korman et al. |
| 10,577,423 | B2 | 3/2020 | Cogswell et al. |
| 10,584,170 | B2 | 3/2020 | Cogswell et al. |
| 10,604,575 | B2 | 3/2020 | Cogswell et al. |
| 2006/0110383 | A1 | 5/2006 | Honjo et al. |
| 2009/0217401 | A1 | 8/2009 | Korman et al. |
| 2009/0297518 | A1 | 12/2009 | Honjo et al. |
| 2011/0081341 | A1 | 4/2011 | Honjo et al. |
| 2012/0263677 | A1 | 10/2012 | Eagle et al. |
| 2013/0017199 | A1 | 1/2013 | Langermann et al. |
| 2013/0133091 | A1 | 5/2013 | Korman et al. |
| 2013/0309250 | A1 | 11/2013 | Cogswell et al. |
| 2014/0212422 | A1 | 7/2014 | Korman et al. |
| 2014/0294852 | A1 | 10/2014 | Korman et al. |
| 2014/0314714 | A1 | 10/2014 | Honjo et al. |
| 2014/0328833 | A1 | 11/2014 | Korman et al. |
| 2014/0341917 | A1 | 11/2014 | Nastri et al. |
| 2014/0348743 | A1 | 11/2014 | Korman et al. |
| 2014/0356353 | A1 | 12/2014 | Queva et al. |
| 2015/0079109 | A1 | 3/2015 | Li et al. |
| 2015/0093380 | A1 | 4/2015 | Honjo et al. |
| 2015/0125463 | A1 | 5/2015 | Cogswell et al. |
| 2015/0165025 | A1 | 6/2015 | Korman et al. |
| 2015/0197572 | A1 | 7/2015 | Honjo et al. |
| 2016/0090417 | A1 | 3/2016 | Cogswell et al. |
| 2016/0158355 | A1 | 6/2016 | Honjo et al. |
| 2016/0158356 | A1 | 6/2016 | Honjo et al. |
| 2016/0376367 | A1 | 12/2016 | Yuan et al. |
| 2017/0051060 | A1 | 2/2017 | Honjo et al. |
| 2017/0088615 | A1 | 3/2017 | Korman et al. |
| 2018/0273624 | A1 | 9/2018 | Cogswell et al. |
| 2018/0282413 | A1 | 10/2018 | Cogswell et al. |
| 2018/0282414 | A1 | 10/2018 | Cogswell et al. |
| 2018/0312590 | A1 | 11/2018 | Cogswell et al. |
| 2018/0319887 | A1 | 11/2018 | Cogswell et al. |
| 2019/0092863 | A1 | 3/2019 | Cogswell et al. |
| 2019/0100589 | A1 | 4/2019 | Cogswell et al. |
| 2019/0100590 | A1 | 4/2019 | Cogswell et al. |
| 2019/0112376 | A1 | 4/2019 | Cogswell et al. |
| 2019/0112377 | A1 | 4/2019 | Cogswell et al. |
| 2019/0135920 | A1 | 5/2019 | Cogswell et al. |
| 2019/0153099 | A1 | 5/2019 | Cogswell et al. |
| 2020/0062846 | A1 | 2/2020 | Honjo et al. |
| 2020/0138945 | A1 | 5/2020 | Korman et al. |
| 2020/0308282 | A1 | 10/2020 | Cogswell et al. |

FOREIGN PATENT DOCUMENTS

| | | | |
|---|---|---|---|
| WO | WO-2007113648 | A2 | 10/2007 |
| WO | WO-2012122444 | A1 | 9/2012 |
| WO | WO-2012145493 | A1 | 10/2012 |
| WO | WO-2013173223 | A1 | 11/2013 |
| WO | WO-2014179664 | A2 | 11/2014 |
| WO | WO-2014194302 | A2 | 12/2014 |
| WO | WO-2015085847 | A1 | 6/2015 |
| WO | WO-2015112800 | A1 | 7/2015 |
| WO | WO-2015112900 | A1 | 7/2015 |
| WO | WO-2016069727 | A1 | 5/2016 |
| WO | WO-2016149201 | A2 | 9/2016 |
| WO | WO-2017210631 | A1 | 12/2017 |

OTHER PUBLICATIONS

Brahmer, J.R., et al., "Safety and Activity of Anti-PD-L1 Antibody in Patients with Advanced Cancer," The New England Journal of Medicine 366(26):2455-2465, Massachusetts Medical Society, United States (Jun. 2012).

Byers, L.A and Rudin, C.M., "Small Cell Lung Cancer: Where Do We Go From Here?," Cancer, 121(5):664-672, Wiley, United States (Mar. 2015).

Calvo, E., et al., "Nivolumab (NIVO) Monotherapy or in Combination With Ipilimumab (IPI) for Treatment of Recurrent Small Cell Lung Cancer (SCLC)," European Journal of Cancer 51(3):S633, Pergamon Press, England (Sep. 2015).

ClinicalTrials, "An Investigational Immuno-therapy Study of Nivolumab, or Nivolumab in Combination With Ipilimumab, or Placebo in Patients With Extensive-Stage Disease Small Cell Lung Cancer (ED-SCLC) After Completion of Platinum-based Chemotherapy (CheckMate 451)," NCT02538666, accessed at https://clinicaltrials.gov/ct2/show/NCT02538666, accessed on Aug. 1, 2018.

ClinicalTrials, "Effectiveness Study of Nivolumab Compared to Chemotherapy in Patients With Relapsed Small-cell Lung Cancer (CheckMate331)," NCT02481830, accessed at https://clinicaltrials.gov/ct2/show/NCT02481830, accessed on Aug. 1, 2018.

Condeelis, J. and Weissleder, R., "In Vivo Imaging in Cancer," Cold Spring Harbor Perspectives in Biology 2(12):a003848, Cold Spring Harbor Laboratory Press, United States (Dec. 2010).

GenBank, "cytotoxic T-lymphocyte-associated protein 4 [*Homo sapiens*]," Accession No. AAB59385.1, accessed on https://www.ncbi.nlm.nih.gov/protein/AAB59385, Nov. 1, 1994.

GenBank, "Human hPD-1 (hPD-1) mRNA, complete cds," Accession No. U64863.1, accessed on https://www.ncbi.nlm.nih.gov/nuccore/U64863, Oct. 12, 2005.

GenBank, "RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen=CD274; Flags: Precursor," Accession No. Q9NZQ7.1, accessed on https://www.ncbi.nlm.nih.gov/protein/Q9NZQ7, Nov. 2, 2016.

Hanna, N., et al., "Randomized Phase III Trial Comparing Irinotecan/cisplatin With Etoposide/cisplatin in Patients With Previously Untreated Extensive-stage Disease Small-cell Lung Cancer," Journal of Clinical Oncology, 24(13):2038-2043, American Society of Clinical Oncology, United States, (May 2006).

Herbst, R.S., et al., "A Study of MPDL3280A, an Engineered PD-L1 Antibody in Patients with Locally Advanced or Metastatic Tumors," Journal of Clinical Oncology 31(Suppl):Abstract 3000, American Society of Clinical Oncology, United States (2013).

Hodi, F.S., et al., "Improved Survival with Ipilimumab in Patients with Metastatic Melanoma," The New England Journal of Medicine 363(8):711-723, Massachusetts Medical Society, United States (Aug. 2010).

Johnson, D.B., et al., "Severe Cutaneous and Neurologic Toxicity in Melanoma Patients during Vemurafenib Administration Following Anti-PD-1 Therapy," Cancer Immunology Research 1(6):373-377, American Association for Cancer Research, United States (Dec. 2013).

Khleif, S., et al., "MEDI4736, An Anti-PD-L1 Antibody with Modified Fc Domain: Preclinical Evaluation and Early Clinical Results from a Phase 1 Study in Patients with Advanced Solid Tumors," Abstract 802, in Proceedings from the European Cancer Congress 2013, Amsterdam, The Netherlands (Sep. 27-Oct. 1, 2013).

Li, Y. and Wu, Y,L., "Immunotherapy for Small-cell Lung Cancer," The Lancet Oncology 17(7):846-847, Lancet Pub. Group, England (Jul. 2016).

McCabe, K.E. and Wu, A.M., "Positive Progress in ImmunoPET—not Just a Coincidence," Cancer Biotherapy & Radiopharmaceuticals 25(3):253-261, Mary Ann Liebert, Inc, United States (Jun. 2010).

NCCN Guidelines® (2014), available at http://www.nccn.org/professionals/physician_gls/f_guidelines.asp, last accessed May 14, 2014, 4 pages.

NCI Drug Dictionary, anti-PD-1 Fusion Protein AMP-224, accessed on Dec. 1, 2016, retrieved from the Internet URL: https://www.cancer.gov/publications/dictionaries/cancer-drug?cdrid=700595.

NCI Drug Dictionary, anti-PD-1 monoclonal antibody MEDI0680, accessed on Dec. 1, 2016, retrieved from the Internet URL: https://www.cancer.gov/publications/dictionaries/cancer-drug?cdrid=756047.

NCI Drug Dictionary, pembrolizumab, accessed on Dec. 1, 2016, retrieved from the Internet URL: https://www.cancer.gov/drugdictionary?cancer-drug?cdrid=695789, 3 pages.

(56) References Cited

OTHER PUBLICATIONS

Olafsen, T., et al., "ImmunoPET Imaging of B-Cell Lymphoma Using 124I-Anti-CD20 scFv Dimers (Diabodies)," Protein Engineering, Design & Selection 23(4):243-249, Oxford University Press, England (Apr. 2010).

International Search report and Written Opinion for Application No. PCT/US2017/035808, dated Aug. 14, 2017, 10 pages.

Puglisi, M., et al., "Treatment Options for Small Cell Lung Cancer—Do We Have More Choice?," British Journal of Cancer, 102(4):629-638, Nature Publishing Group on behalf of Cancer Research UK, England, (Feb. 2010).

Retrieved from the Internet: (http://www.cancer.org/cancer/lungcancer-smallcell/detailedguide/small-cell-lung-cancer-staging), last visited Jun. 2, 2016.

Zatloukal, P., et al., "A Multicenter International Randomized Phase III Study Comparing Cisplatin in Combination With Irinotecan or Etoposide in Previously Untreated Small-cell Lung Cancer Patients With Extensive Disease," Annals of Oncology, 21(9):1810-1816, Oxford University Press, England (Sep. 2010).

Rini, B.I., et al., "Phase 1 Dose-escalation Trial of Tremelimumab Plus Sunitinib in Patients with Metastatic Renal Cell Carcinoma," Cancer 117(14):758-767, Wiley, United States (Feb. 2011).

Rossi, A., et al., "Optimal Drugs for Second-line Treatment of Patients With Small-cell Lung Cancer," Expert Opinion on Pharmacotherapy 17(7):969-976, Ashley Publications, England (Feb. 2016).

Sharp, A., et al., "Development of Molecularly Targeted Agents and Immunotherapies in Small Cell Lung Cancer," European Journal of Cancer 60:26-39, Pergamon Press, England (Jun. 2016).

Simon, R., "Optimal Two-stage Designs for Phase II Clinical Trials," Controlled Clinical Trials, 10(1):1-10, Elsevier, United States (Mar. 1989).

Sjoblom, T., et al., "The Consensus Coding Sequences of Human Breast and Colorectal Cancers," Science 314(5797):268-274, American Association for the Advancement of Science, United States (Oct. 2006).

Taube, J.M., et al., "Colocalization of Inflammatory Response with B7-H1 Expression in Human Melanocytic Lesions Supports an Adaptive Resistance Mechanism of Immune Escape," Science Translational Medicine 4(127):127ra37, American Association for the Advancement of Science, United States (Mar. 2012).

Taylor, M., et al., "Phase I/II Study of Nivolumab with or without Ipilimumab for Treatment of Recurrent Small Cell Lung Cancer (SCLC): CA209-032," Journal for Immunotherapy of Cancer 3(Suppl 2):1-2, BioMed Central, England (Nov. 2015).

Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).

Topalian, S.L., et al., "Targeting the PD-1/B7-H1(PD-L1) Pathway to Activate Anti-tumor Immunity," Current Opinion in Immunology 24(2):207-212, Elsevier, England (Apr. 2012).

Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).

Wolchok, J.D., et al., "Nivolumab Plus Ipilimumab in Advanced Melanoma," The New England Journal of Medicine 369(2):122-133, Massachusetts Medical Society, United States (Jul. 2013).

Bai, S., et al., "A guide to rational dosing of monoclonal antibodies," Clin Pharmacokinet 51(2): 119-135, Springer Link, Germany (Feb. 1, 2012).

* cited by examiner

Nivolumab-3

Nivolumab-1 + Ipilimumab-3

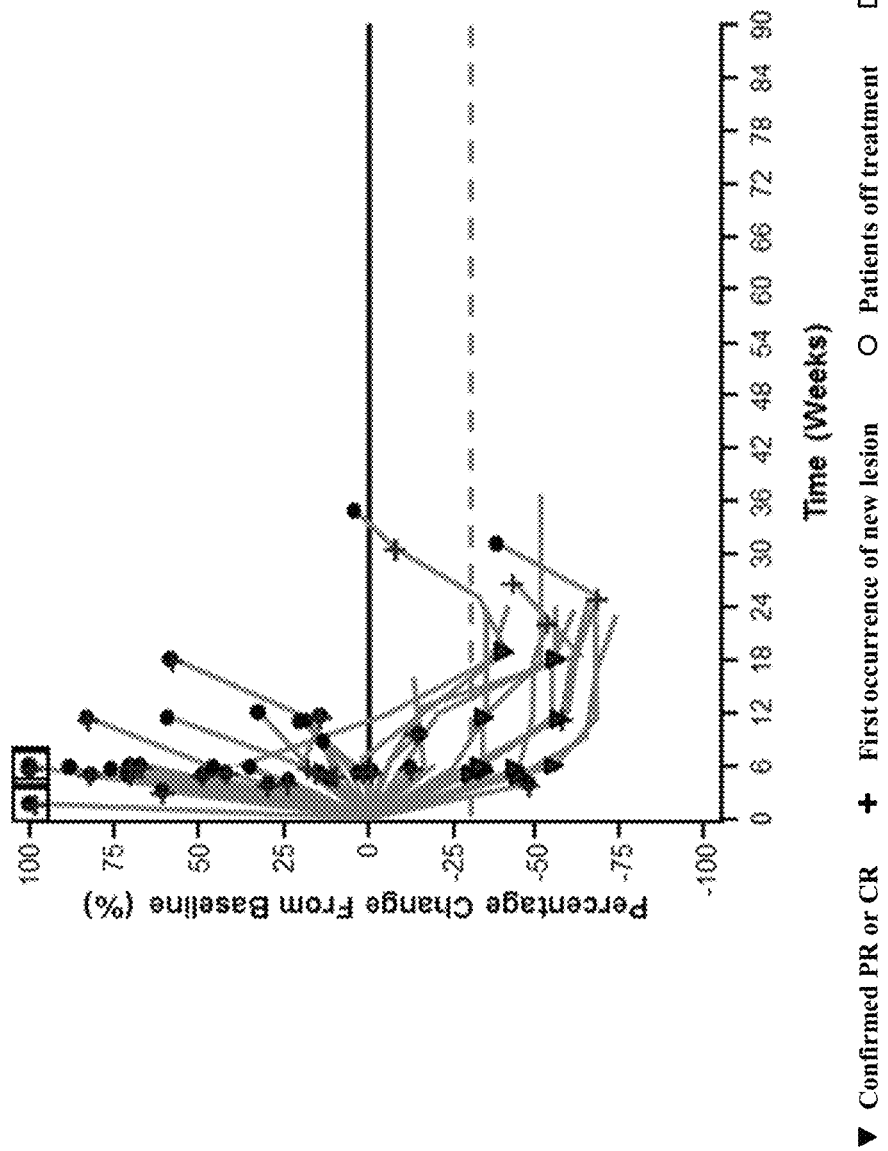

Nivolumab-3

Nivolumab-1 + Ipilimumab-3

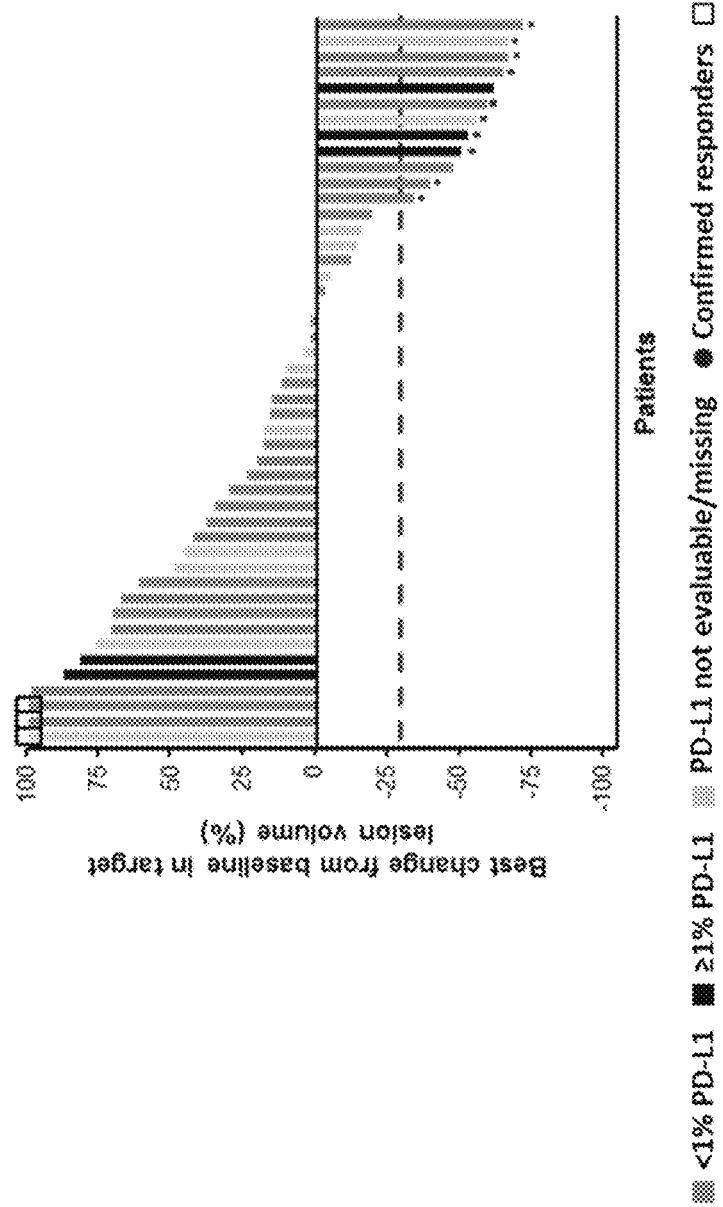

METHOD OF TREATING LUNG CANCER

FIELD OF THE DISCLOSURE

This disclosure relates to methods for treating a tumor derived from a small cell lung cancer in a subject comprising administering to the subject an anti-Programmed Death-1 (PD-1) antibody or a combination of an anti-PD-1 antibody and an anti-Cytotoxic T-Lymphocyte Antigen-4 (CTLA-4) antibody.

BACKGROUND OF THE DISCLOSURE

Human cancers harbor numerous genetic and epigenetic alterations, generating neoantigens potentially recognizable by the immune system (Sjoblom et al., (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down-regulate T cell activation and cytokine secretion upon binding to PD-1.

Nivolumab (formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol* Res. 2(9):846-56).

Ipilimumab (YERVOY®) is a fully human, IgG1 monoclonal antibody that blocks the binding of CTLA-4 to its B7 ligands, thereby stimulating T cell activation and improving overall survival (OS) in patients with advanced melanoma (Hodi et al. (2010) *N Engl J Med* 363:711-23). Concurrent therapy with nivolumab and ipilimumab in a Phase 1 clinical trial produced rapid and deep tumor regression in a substantial proportion of patients with advanced melanoma, and was significantly more effective than either antibody alone (Wolchok et al. (2013) *N Engl J Med* 369(2):122-33; WO 2013/173223). However, it was hitherto not known whether this combination of immunoregulatory antibodies would be similarly effective for the treatment of small-cell lung cancer (SCLC).

SCLC accounts for approximately 14% of all lung cancers (Byers and Rudin, *Cancer* 121:664-72 (2015)). Most patients present with extensive-stage disease characterized by widespread metastases and poor survival. Although 35% to 86% of patients respond to first-line chemotherapy, disease progresses rapidly, and outcomes with second-line treatment are poor (Hanna et al., *J. Clin. Oncol.* 24:2038-43 (2006); Puglisi et al., *Br. J. Cancer* 102:629-38 (2010); Zatloukal et al., *Ann. Oncol.* 21:1810-16 (2010)). Accordingly, there remains a need for effective therapies for the treatment of SCLC and, in particular, second line therapies for patients that relapse following initial treatment.

SUMMARY OF THE DISCLOSURE

The present disclosure relates to a method for treating a subject afflicted with a tumor derived from a small-cell lung cancer (SCLC) comprising administering to the subject a combination of: (a) an antibody or an antigen-binding portion thereof that binds specifically to a Programmed Death-1 (PD-1) receptor and inhibits PD-1 activity ("anti-PD-1 antibody").

Other aspects of the present disclosure relate to a method for treating a subject afflicted with a tumor derived from a SCLC comprising administering to the subject a combination of: (a) an anti-PD-1 antibody and (b) an antibody or an antigen-binding portion thereof that binds specifically to Cytotoxic T-Lymphocyte Antigen-4 (CTLA-4) and inhibits CTLA-4 activity ("anti-CTLA-4 antibody").

In some embodiments, the anti-PD-1 antibody cross-competes with nivolumab for binding to human PD-1. In embodiments, the anti-PD-1 antibody is a chimeric, humanized or human monoclonal antibody or a portion thereof. In other embodiments, the anti-PD-1 antibody comprises a heavy chain constant region which is of a human IgG1 or IgG4 isotype. In certain embodiment, the anti-PD-1 antibody is nivolumab. In one embodiment, the anti-PD-1 antibody is pembrolizumab.

In some embodiments, the anti-CTLA-4 antibody is a chimeric, humanized or human monoclonal antibody or a portion thereof. In some embodiments, the anti-CTLA-4 antibody comprises a heavy chain constant region which is of a human IgG1 isotype. In certain embodiments, the anti-CTLA-4 antibody is ipilimumab. In other embodiments, the anti-CTLA-4 antibody is tremelimumab. In some embodiments, the anti-CTLA-4 antibody o cross-competes with ipilimumab for binding to human CTLA-4.

In some embodiments, the anti-PD-1 antibody or antigen-binding portion thereof is administered at a dose of about 1 mg/kg or about 3 mg/kg body weight once about every 2 weeks. In other embodiments, the anti-PD-1 antibody or antigen-binding portion thereof is administered at a dose of about 1 mg/kg or about 3 mg/kg body weight once about every 3 weeks. In certain embodiments, the anti-CTLA-4 antibody or antigen-binding portion thereof is administered at a dose of about 1 mg/kg or about 3 mg/kg body weight. In other embodiments, the anti-PD-1 antibody or antigen-binding portion thereof is administered at a dose of about 3 mg/kg body weight once about every 3 weeks and the anti-CTLA-4 antibody or antigen-binding portion thereof is administered at a dose of about 1 mg/kg body weight once about every 3 weeks. In certain embodiments, the anti-PD-1 antibody or antigen-binding portion thereof is administered at a dose of about 1 mg/kg body weight once about every 3 weeks and the anti-CTLA-4 antibody or antigen-binding portion thereof is administered at a dose of about 3 mg/kg body weight once about every 3 weeks.

In certain embodiments, a subject treated with a disclosed method exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years.

In some embodiments, the subject exhibits progression-free survival of at least about eight months after the initial administration.

In embodiments, the subject has a lung tumor that has ≥1% PD-L1 expression. In certain embodiments, the anti-PD-1 antibody or the anti-PD-1 antibody and anti-CTLA-4 combination is administered for as long as clinical benefit is observed or until disease progression or unmanageable toxicity occurs. In one embodiment, the anti-PD-1 and/or anti-CTLA-4 antibodies are formulated for intravenous administration. In certain embodiments, the anti PD-1 antibody and the anti-CTLA-4 antibody are administered sequentially to the subject. In some embodiments, the anti-PD-1 and anti-CTLA-4 antibodies are administered within 30 minutes of each other. In one embodiment, the anti-PD-1 antibody is administered before the anti-CTLA-4 antibody. In another embodiment, the anti-CTLA-4 antibody is administered before the anti-PD-1 antibody. In some embodiments, the anti-PD-1 antibody and the anti-CTLA-4 antibody are administered concurrently in separate compositions. In certain embodiments, the anti-PD-1 antibody and the anti-CTLA-4 antibody are administered concurrently as a single composition.

In one embodiment, the anti-PD-1 antibody is administered at a subtherapeutic dose. In certain embodiments, the anti-CTLA-4 antibody. In some embodiments, the anti-PD-1 antibody and the anti-CTLA-4 antibody are each administered at a subtherapeutic dose.

The present disclosure further relates to a kit for treating a subject afflicted with a tumor derived from a SCLC, the kit comprising: (a) an amount ranging from about 4 mg to about 500 mg of an anti-PD-1 antibody; and (b) instructions for using the PD-1 antibody and the CTLA-4 antibody in any disclosed method.

The present disclosure further relates to a kit for treating a subject afflicted with a tumor derived from a SCLC, the kit comprising: (a) an amount ranging from about 4 mg to about 500 mg of an anti-PD-1 antibody; (b) an amount ranging from about 4 mg to about 500 mg of a CTLA-4 antibody; and (c) instructions for using the PD-1 antibody and the CTLA-4 antibody in any disclosed method.

Other features and advantages of the instant disclosure will be apparent from the following detailed description and examples which should not be construed as limiting. The contents of all cited references, including scientific articles, newspaper reports, GenBank entries, patents and patent applications cited throughout this application are expressly incorporated herein by reference.

EMBODIMENTS

E1. A method for treating a subject afflicted with a tumor derived from a small-cell lung cancer (SCLC) comprising administering to the subject an antibody or an antigen-binding portion thereof that binds specifically to a Programmed Death-1 (PD-1) receptor and inhibits PD-1 activity ("anti-PD-1 antibody").

E2. The method of embodiment E1, further comprising administering to the subject an antibody or an antigen-binding portion thereof that binds specifically to Cytotoxic T-Lymphocyte Antigen-4 (CTLA-4) and inhibits CTLA-4 activity ("anti-CTLA-4 antibody").

E3. The method of embodiment E1 or E2, wherein the SCLC comprises a small cell carcinoma.

E4. The method of embodiment E1 or E2, wherein the SCLC comprises a combined small cell carcinoma.

E5. The method of any one of embodiments E1 to E4, wherein the SCLC is a recurrent SCLC.

E6. The method of any one of embodiments E1 to E5, wherein the subject received at least one, at least two, at least three, at least four, or at least five previous lines of therapy to treat the tumor.

E7. The method of embodiment E6, wherein the previous line of therapy comprises a chemotherapy.

E8. The method of embodiment E7, wherein the chemotherapy comprises a platinum-based therapy.

E9. The method of embodiment E8, wherein the platinum-based therapy comprises a platinum-based antineoplastic selected from the group consisting of cisplatin, carboplatin, oxaliplatin, nedaplatin, triplatin tetranitrate, phenanthriplatin, picoplatin, satraplatin, and any combination thereof.

E10. The method of embodiment E7 or E8, wherein the platinum-based therapy comprises cisplatin.

E11. The method of any one of embodiments E1 to E10, wherein the anti-PD-1 antibody cross-competes with nivolumab for binding to human PD-1.

E12. The method of any one of embodiments E1 to E11, wherein the anti-PD-1 antibody binds to the same epitope as nivolumab.

E13. The method of any one of embodiments E1 to E12, wherein the anti-PD-1 antibody is a chimeric, humanized or human monoclonal antibody or a portion thereof.

E14. The method of any one of embodiments E1 to E13, wherein the anti-PD-1 antibody comprises a heavy chain constant region which is of a human IgG1 or IgG4 isotype.

E15. The method of any one of embodiments E1 to E14, wherein the anti-PD-1 antibody is nivolumab.

E16. The method of any one of embodiments E1 to E14, wherein the anti-PD-1 antibody is pembrolizumab.

E17. The method of any one of embodiments E2 to E16, wherein the anti-CTLA-4 antibody is a chimeric, humanized or human monoclonal antibody or a portion thereof.

E18. The method of any one of embodiments E2 to E17, wherein the anti-CTLA-4 antibody comprises a heavy chain constant region which is of a human IgG1 isotype.

E19. The method of any one of embodiments E2 to E18, wherein the anti-CTLA-4 antibody is ipilimumab.

E20. The method of any one of embodiments E2 to E18, wherein the anti-CTLA-4 antibody is tremelimumab.

E21. The method of any one of embodiments E2 to E20, wherein the anti-CTLA-4 antibody cross-competes with ipilimumab for binding to human CTLA-4.

E22. The method of any one of embodiments E1 to E21, wherein the anti-PD-1 antibody is administered at a dose ranging from at least about 0.1 mg/kg to at least about 10.0 mg/kg body weight once about every 1, 2, 3, or 4 weeks.

E23. The method of any one of embodiments E1 to E22, wherein the anti-PD-1 antibody is administered at a dose of about 1 mg/kg or about 3 mg/kg body weight E24. The method of any one of embodiments E1 to E21, wherein the anti-PD-1 antibody or antigen-binding portion thereof is administered at a flat dose.

E25. The method of any one of embodiments E1 to E21 and E24, wherein the anti-PD-1 antibody or antigen-binding portion thereof is administered at a flat dose of at least about 200, at least about 220, at least about 240, at least about 260, at least about 280, at least about 300, at least about 320, at least about 340, at least about 360, at least about 380, at least about 400, at least about 420, at least about 440, at least about 460, at least about 480, at least about 500 or at least about 550 mg.

E26. The method of any one of embodiments E1 to E21, E24, and E25, wherein the anti-PD-1 antibody or antigen-binding portion thereof is administered at a flat dose about once every 1, 2, 3, or 4 weeks.

E27. The method of anyone of embodiments E1 to E26, wherein the anti-PD-1 antibody is administered once about every 2 weeks.

E28. The method of anyone of embodiments E1 to E26, wherein the anti-PD-1 antibody is administered once about every 3 weeks.

E29. The method of any one of embodiments E1 to E28, wherein the anti-PD-1 antibody is administered for as long as clinical benefit is observed or until unmanageable toxicity or disease progression occurs.

E30. The method of any one of embodiments E2 to E29, wherein the anti-CTLA-4 antibody is administered at a dose ranging from at least about 0.1 mg/kg to at least about 10.0 mg/kg body weight once about every 1, 2, 3, or 4 weeks.

E31. The method of any one of embodiments E2 to E30, wherein the anti-CTLA-4 is administered at a dose of about 1 mg/kg or about 3 mg/kg body weight.

E32. The method of any one of embodiments E2 to E31, wherein the anti-PD-1 antibody or antigen-binding portion thereof is administered at a flat dose.

E33. The method of anyone of embodiments E2 to E32, wherein the anti-CTLA-4 antibody is administered once about every 2 weeks.

E34. The method of anyone of embodiments E2 to E32, wherein the anti-CTLA-4 antibody is administered once about every 3 weeks.

E35. The method of any one of embodiments E2 to E34, wherein the anti-PD-1 antibody is administered at a dose of about 3 mg/kg body weight once about every 3 weeks and the anti-CTLA-4 antibody or antigen-binding portion thereof is administered at a dose of about 1 mg/kg body weight once about every 3 weeks.

E36. The method of any one of embodiments E2 to E34, wherein the anti-PD-1 antibody is administered at a dose of about 1 mg/kg body weight once about every 3 weeks and the anti-CTLA-4 antibody or antigen-binding portion thereof is administered at a dose of about 3 mg/kg body weight once about every 3 weeks.

E37. The method of any one of embodiments E1 to E36, wherein the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration.

E38. The method of any one of embodiments E1 to E37, wherein the subject has a tumor that has ≥1% PD-L1 expression.

E39. The method of any one of embodiments E1 to E38, wherein the subject has a tumor that has ≥5% PD-L1 expression.

E40. The method of any one of embodiments E2 to E39, wherein the combination is administered for as long as clinical benefit is observed or until disease progression or unmanageable toxicity occurs.

E41. The method of any one of embodiments E1 to E40, wherein the anti-PD-1 antibody is formulated for intravenous administration.

E42. The method of any one of embodiments E2 to E41, wherein the anti-CTLA-4 antibody is formulated for intravenous administration.

E43. The method of any one of embodiments E2 to E42, wherein the anti-PD-1 antibody and the anti-CTLA-4 antibody are administered sequentially to the subject.

E44. The method of any one of claims 2-43, wherein the anti-PD-1 and anti-CTLA-4 antibodies are administered within 30 minutes of each other.

E45. The method of any one of embodiments E2 to E44, wherein the anti-PD-1 antibody or antigen-binding portion thereof is administered before the anti-CTLA-4 antibody or antigen-binding portion thereof.

E46. The method of any one of embodiments E2 to E44, wherein the anti-CTLA-4 antibody or antigen-binding portion thereof is administered before the anti-PD-1 antibody or antigen-binding portion thereof.

E47. The method of any one of embodiments E2 to E42, wherein the anti-PD-1 antibody or antigen-binding portion thereof and the anti-CTLA-4 antibody or antigen-binding portion thereof are administered concurrently in separate compositions.

E48. The method of any one of embodiments E2 to E42, wherein the anti-PD-1 antibody or antigen-binding portion thereof and the anti-CTLA-4 antibody or antigen-binding portion thereof are administered concurrently as a single composition.

E49. The method of any one of embodiments E1 to E48, wherein the anti-PD-1 antibody or antigen-binding portion thereof is administered at a subtherapeutic dose.

E50. The method of any one of embodiments E2 to E49, wherein the anti-CTLA-4 antibody or antigen-binding portion thereof is administered at a subtherapeutic dose.

E51. The method of any one of embodiments E2 to E50, wherein the anti-PD-1 antibody or antigen-binding portion thereof and the anti-CTLA-4 antibody or antigen-binding portion thereof are each administered at a subtherapeutic dose.

E52. A kit for treating a subject afflicted with a tumor derived from an SCLC, the kit comprising:
(a) an amount ranging from about 4 mg to about 500 mg of an anti-PD-1 antibody or an antigen-binding portion thereof, and
(b) instructions for using the PD-1 antibody in the method of any of embodiments E1 to E51.

E53. A kit for treating a subject afflicted with a tumor derived from an SCLC, the kit comprising:
(a) an amount ranging from about 4 mg to about 500 mg of an anti-PD-1 antibody or an antigen-binding portion thereof,
(b) an amount ranging from about 4 mg to about 500 mg of a CTLA-4 antibody or an antigen-binding portion thereof, and
(c) instructions for using the PD-1 antibody and the CTLA-4 antibody in the method of any of embodiments E2 to E51.

BRIEF DESCRIPTION OF THE DRAWINGS

FIGS. 3A-3C provide graphical representations of the changes in tumor burden in individual patients receiving nivolumab 3 mg/kg (FIG. 3A), nivolumab 1 mg/kg plus ipilimumab 3 mg/kg (FIG. 3B), and nivolumab 3 mg/kg plus ipilimumab 1 mg/kg (FIG. 3C). Only patients with target lesions at baseline and with at least one on-treatment tumor assessment were included (nivolumab 3 mg/kg, n=80; nivolumab 1 mg/kg plus ipilimumab 3 mg/kg, n=46; nivolumab 3 mg/kg plus ipilimumab 1 mg/kg, n=47). Horizontal grey lines indicate the 30% reduction consistent with a Response Evaluation Criteria in Solid Tumors (RECIST; version 1.1) objective response. Subjects displaying a complete response (CR) or a partial response (PR) are marked by an inverted triangle at the point of PR or CR. A plus sign indicates the first occurrence of a new lesion, and an open circle indicates the point at which the subject went off treatment. Measurements in excess of 100% were truncated to 100%, and the data point is marked by an open square.

FIGS. 5A-5C provide graphical representations of the changes in tumor burden according to tumor PD-L1 expression status. The percent change from baseline for tumors with less than 1% PD-L1 expression are shown in grey and for tumors with ≥1% PD-L1 expression shown in black. The change in baseline for tumors where PD-L1 expression was not evaluable or missing are shown in light grey. Closed circles above a bar indicate a confirmed responder. Open boxes indicate that the % change was truncated to 100%.

DETAILED DESCRIPTION OF THE DISCLOSURE

Figure 1:
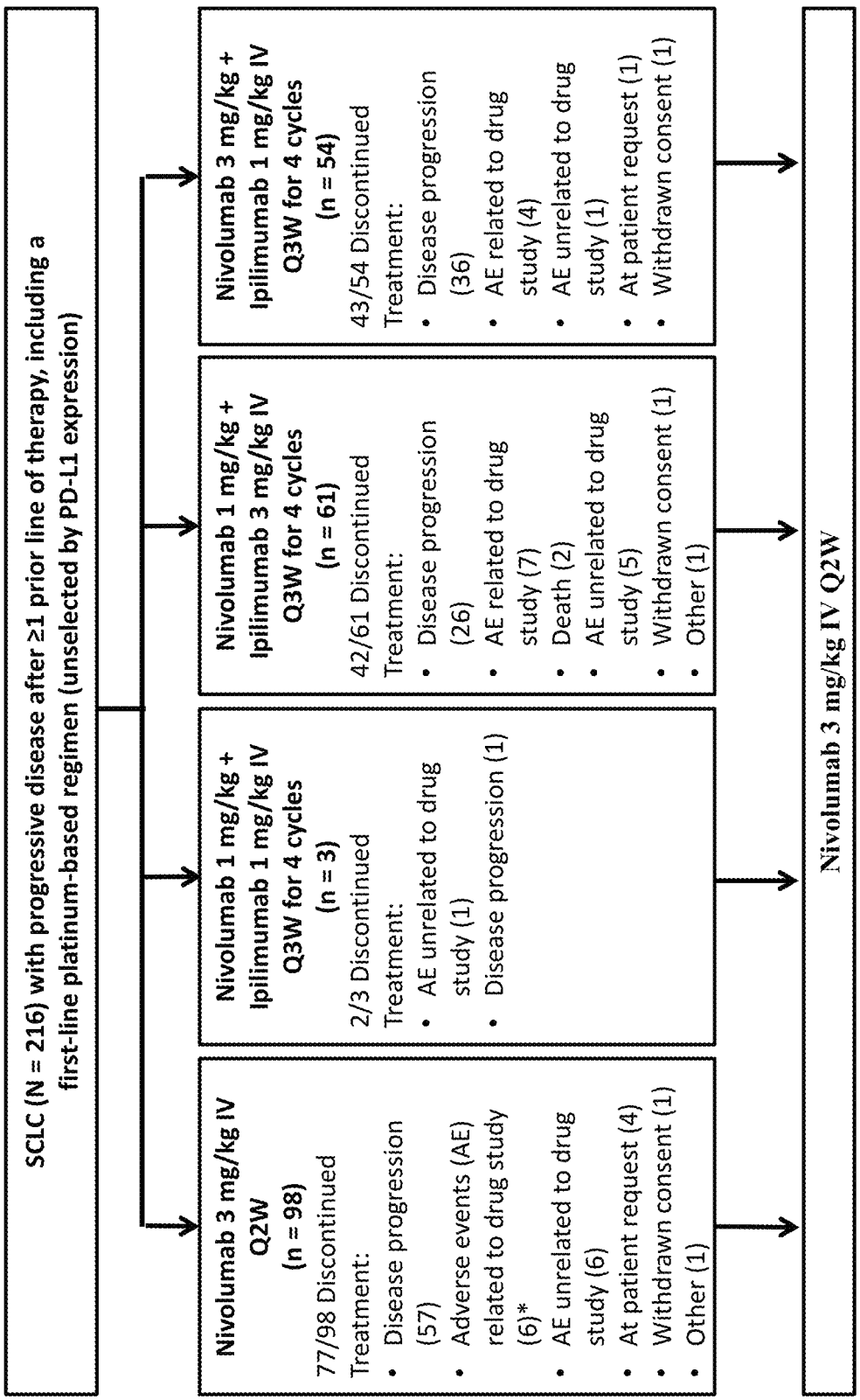
FIG. 1 shows a schematic representation of a study design for treatment of a tumor derived from an SCLC using an anti-PD-1 antibody or a combination of an anti-PD-1 antibody and an anti-CTLA-4 antibody.
Figure 2B:
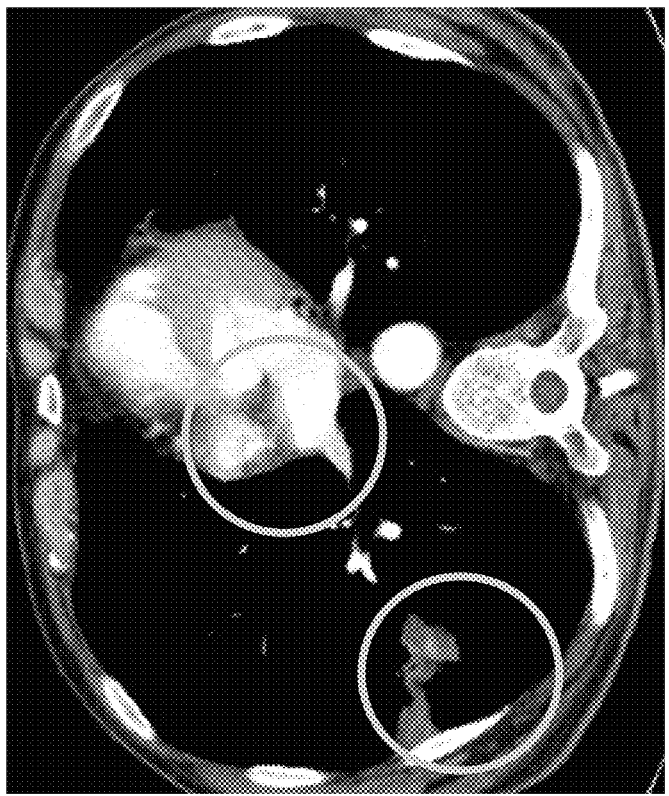
FIGS. 2A and 2B show images of a tumor derived from a SCLC found in a subject's lungs before (FIG. 2A) and after (FIG. 2B) treatment with a combination of nivolumab 1 mg/kg body weight and ipilimumab 3 mg/kg body weight. Tumor tissue is circled in both FIG. 2A and FIG. 2B.
Figure 2A:
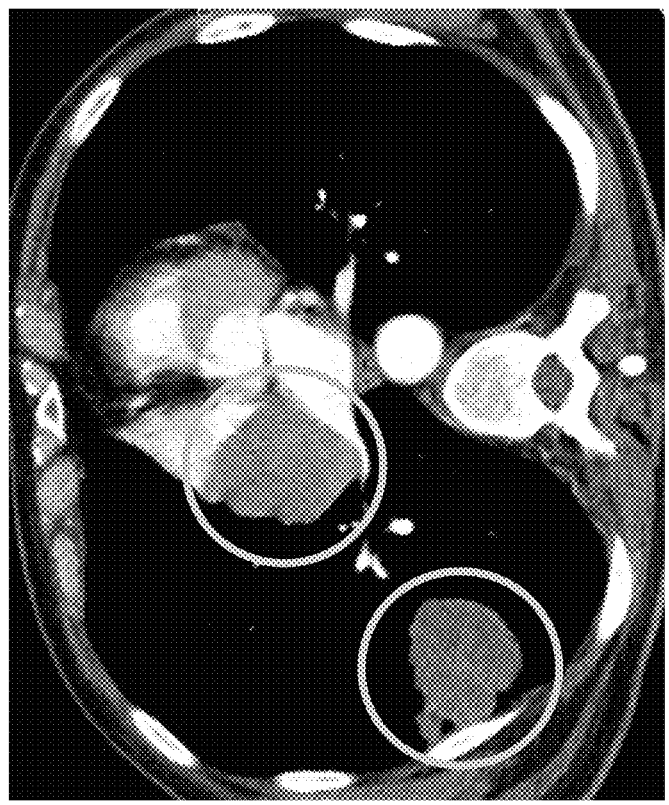

The present disclosure relates to methods for treating a tumor derived from an SCLC in a patient comprising administering to the patient an anti-PD-1 antibody or a combination of an anti-PD-1 antibody and an anti-CTLA-4 antibody.

Terms

In order that the present disclosure can be more readily understood, certain terms are first defined. As used in this application, except as otherwise expressly provided herein, each of the following terms shall have the meaning set forth below. Additional definitions are set forth throughout the application.

"Administering" refers to the physical introduction of a composition comprising a therapeutic agent to a subject, using any of the various methods and delivery systems known to those skilled in the art. Routes of administration for the anti-PD-1 antibody include intravenous, intramuscular, subcutaneous, intraperitoneal, spinal, or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the combination is administered via a non-parenteral route, in some embodiments, orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event can be associated with activation of the immune system or expansion of immune system cells (e.g., T cells) in response to a treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises at least three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FRs). Each $V_H$ and $V_L$ comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

An immunoglobulin can derive from any of the commonly known isotypes, including but not limited to IgA, secretory IgA, IgG, and IgM. IgG subclasses are also well known to those in the art and include but are not limited to human IgG1, IgG2, IgG3, and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or non-human antibodies; wholly synthetic antibodies; and single chain antibodies. A non-human antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 can, however, have cross-reactivity to other antigens, such as PD-1 molecules from different species. Moreover, an isolated antibody can be substantially free of other cellular material and/or chemicals.

The term "monoclonal antibody" (mAb) refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody. MAbs can be produced by hybridoma, recombinant, transgenic, or other techniques known to those skilled in the art.

A "human antibody" (HuMAb) refers to an antibody having variable regions in which both the FRs and CDRs are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibodies" and "fully human antibodies" are used synonymously.

A "humanized antibody" refers to an antibody in which some, most or all of the amino acids outside the CDRs of a non-human antibody are replaced with corresponding amino acids derived from human immunoglobulins. In one embodiment of a humanized form of an antibody, some, most or all of the amino acids outside the CDRs have been replaced with amino acids from human immunoglobulins, whereas some, most, or all amino acids within one or more CDRs are unchanged. Small additions, deletions, insertions, substitutions, or modifications of amino acids are permissible as long as they do not abrogate the ability of the antibody to bind to a particular antigen. A "humanized antibody" retains an antigenic specificity similar to that of the original antibody. In some embodiments, the CDRs of a humanized antibody contain CDRs from a non-human, mammalian antibody. In other embodiments, the CDRs of a humanized antibody contain CDRs from an engineered, synthetic antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen antibody" refers to an antibody that binds specifically to the antigen. For example, an anti-PD-1 antibody binds specifically to PD-1 and an anti-CTLA-4 antibody binds specifically to CTLA-4.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. A "cancer" or "cancer tissue" can include a tumor. Unregulated cell division and growth results in the formation of malignant tumors that invade neighboring tissues and may also metastasize to distant parts of the body through the lymphatic system or bloodstream. Following metastasis, the distal tumors can be said to be "derived from" the original, pre-metastasis tumor. For example, a "tumor derived from" an SCLC refers to a tumor that is the result of a metastasized SCLC. Because the distal tumor is derived from the pre-metastasis tumor, the "derived from" tumor can also comprise the pre-metastasis tumor, e.g., a tumor derived from an SCLC can comprise an SCLC.

"Cytotoxic T-Lymphocyte Antigen-4" (CTLA-4) refers to an immunoinhibitory receptor belonging to the CD28 family. CTLA-4 is expressed exclusively on T cells in vivo, and binds to two ligands, CD80 and CD86 (also called B7-1 and B7-2, respectively). The term "CTLA-4" as used herein includes human CTLA-4 (hCTLA-4), variants, isoforms, species homologs of hCTLA-4, and analogs having at least one common epitope with hCTLA-4. The complete hCTLA-4 sequence can be found under GenBank Accession No. AAB59385.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

"PD-L1 positive" as used herein can be interchangeably used with "PD-L1 expression of at least about 1%." In one embodiment, the PD-L1 expression can be used by any methods known in the art. In another embodiment, the PD-L1 expression is measured by an automated IHC. PD-L1 positive tumor can thus have at least about 1%, at least about 2%, at least about 5%, at least about 10%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100% of tumor cells expressing PD-L1 as measured by an automated IHC. In certain embodiments, "PD-L1 positive" means that there are at least 100 cells that express PD-L1 on the surface of the cells. In other embodiments, "PD-L2 positive" means that there are at least 100 cells that express PD-L2 on the surface of the cells.

"Programmed Death-1" (PD-1) refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1" (PD-L1) is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

A "subject" includes any human or non-human animal. The term "non-human animal" includes, but is not limited to, vertebrates such as non-human primates, sheep, dogs, and rodents such as mice, rats, and guinea pigs. In some embodiments, the subject is a human. The terms, "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, "subtherapeutic dose" means a dose of a therapeutic compound (e.g., an antibody) that is lower than the usual or typical dose of the therapeutic compound when administered alone for the treatment of a hyperproliferative disease (e.g., cancer).

By way of example, an "anti-cancer agent" promotes cancer regression in a subject or prevents further tumor growth. In certain embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent can inhibit cell growth or tumor growth by at least about 10%, by at least about 20%, by at least about 30%, by at least about 40%, by at least about 50%, by at least about 60%, by at least about 70%, by at least about 80%, by at least about 90%, by at least about 95%, or by at least about 100% relative to untreated subjects. In other embodiments of the disclosure, tumor regression can be observed and continue for a period of at least about 20 days, at least about 30 days, at least about 40 days, at least about 50 days, or at least about 60 days. Notwithstanding these ultimate measurements of therapeutic effectiveness, evaluation of immunotherapeutic drugs must also make allowance for "immune-related response patterns".

An "immune-related response pattern" refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

A therapeutically effective amount of a drug includes a "prophylactically effective amount," which is any amount of the drug that, when administered alone or in combination with an anti-neoplastic agent to a subject at risk of developing a cancer (e.g., a subject having a pre-malignant condition) or of suffering a recurrence of cancer, inhibits the development or recurrence of the cancer. In certain embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The term "weight based dose", as referred to herein, means that a dose administered to a patient is calculated based on the weight of the patient. For example, when a patient with 60 kg body weight requires 3 mg/kg of an anti-PD-1 antibody, one can calculate and use the appropriate amount of the anti-PD-1 antibody (i.e., 180 mg) for administration.

The use of the term "fixed dose" with regard to a method of the disclosure means that two or more different antibodies in a single composition (e.g., anti-PD-1 antibody and anti-CTLA-4 antibody) are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody (e.g., anti-PD-1 antibody) to mg second antibody (e.g., anti-CTLA-4 antibody). For example, the 3:1 ratio of an anti-PD-1 antibody and an anti-CTLA-4 antibody can mean that a vial can contain about 240 mg of the anti-PD-1 antibody and 80 mg of the anti-CTLA-4 antibody or about 3 mg/ml of the anti-PD-1 antibody and 1 mg/ml of the anti-CTLA-4 antibody.

The use of the term "flat dose" with regard to the methods and dosages of the disclosure means a dose that is administered to a patient without regard for the weight or body surface area (BSA) of the patient. The flat dose is therefore not provided as a mg/kg dose, but rather as an absolute amount of the agent (e.g., the anti-CTLA-4 antibody and/or anti-PD-1 antibody). For example, a 60 kg person and a 100 kg person would receive the same dose of an antibody (e.g., 240 mg of an anti-PD-1 antibody).

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days±one day, i.e., every six days to every eight days. "Once about every two weeks" can include every fourteen days±three days, i.e., every eleven days to every seventeen days. Similar approximations apply, for example, to once about every three weeks, once about every four weeks, once about every five weeks, once about every six weeks and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

Methods of the Disclosure

This disclosure provides a method of treating a subject afflicted with a tumor derived from an SCLC, which method comprises administering to the subject an antibody or an antigen-binding portion thereof that binds specifically to a Programmed Death-1 (PD-1) receptor and inhibits PD-1 activity ("anti-PD-1 antibody"). This disclosure further provides a method of treating a subject afflicted with a tumor derived from an SCLC, which method comprises administering to the subject a combination of (a) an antibody or an antigen-binding portion thereof that specifically binds to and a PD-1 receptor and inhibits PD-1 activity ("anti-PD-1 antibody"); and (b) an antibody or an antigen-binding portion thereof that binds specifically to Cytotoxic T-Lymphocyte Antigen-4 (CTLA-4) and inhibits CTLA-4 activity ("anti-CTLA-4 antibody"). In some embodiments, the subject is a human patient.

In certain embodiments, the subject is a chemotherapy-naïve patient (e.g., a patient who has not previously received any chemotherapy). In other embodiments, the subject has received another cancer therapy (e.g., a chemotherapy), but is resistant or refractory to such another cancer therapy. In one particular embodiment, the SCLC is a recurrent SCLC. In some embodiments, the subject received at least one, at least two, at least three, at least four, or at least five previous lines of therapy to treat the tumor. In one embodiment, the subject received one previous line of therapy to treat the tumor. In another embodiment, the subject received two previous lines of therapy to treat the tumor. In another embodiment, the subject received three previous lines of therapy to treat the tumor. In another embodiment, the subject received four previous lines of therapy to treat the tumor. In another embodiment, the subject received five previous lines of therapy to treat the tumor. In another embodiment, the subject received more than five previous lines of therapy to treat the tumor.

In certain embodiments, the previous line of therapy comprises a chemotherapy. In some embodiments, the chemotherapy comprises a platinum-based therapy. In certain embodiments, the platinum based therapy comprises a platinum-based antineoplastic selected from the group consisting of cisplatin, carboplatin, oxaliplatin, nedaplatin, triplatin tetranitrate, phenanthriplatin, picoplatin, satraplatin, and any combination thereof. In one particular embodiment, the platinum-based therapy comprises cisplatin (e.g., cisplatin in combination with etoposide). In some embodiments, the subject has received a previous radiotherapy. In other embodiments, the previous therapy comprises an antibody therapy.

In certain specific embodiments, the subject has cancer cells expressing mutated forms of the EGFR or KRAS gene. In certain embodiments, the subject has cancer cells that are PD-L1 positive. In certain embodiments, the subject has cancer cells that are PD-L1 negative. In some embodiments, the subject never smoked. In certain embodiments, the subject formerly smoked. In one embodiment, the subject currently smokes. In certain embodiments, the SCLC comprises a small cell carcinoma. In certain embodiments, the SCLC comprises a combined small cell carcinoma.

In some embodiments, the present methods comprise administering an effective amount of an anti-PD-1 antibody or administering an effective amount of an anti-PD-L1 antibody and an effective amount of an anti-CTLA-4 antibody. An effective amount of an anti-PD-1 antibody and/or an anti-CTLA-4 antibody can be a flat dose or a weight based dose.

In some embodiments, the disclosure includes a method of treating a cancer or a subject afflicted with cancer comprising administering an anti-PD-1 antagonist in combination with an anti-CD30 antibody to treat cancer. An "anti-PD-1 antagonist" as referred herein includes any molecule that inhibits interaction between PD-1 (receptor) and PD-L1 (ligand) such that the signal pathway of PD-1/PD-L1 is blocked. In other embodiments, an anti-PD-1 antagonist is a PD-1-Fc fusion protein. In certain embodiments, an anti-PD-1 antagonist includes an anti-PD-1 fusion protein, an antisense molecule, a small molecule, a ribozyme, or a nanobody that inhibits or prevents interaction between PD-1 and PD-L1.

In certain embodiments, the therapy of the present disclosure (e.g., administration of an anti-PD-1 antibody or administration of an anti-PD-1 antibody and an anti-CTLA-4 antibody) effectively increases the duration of survival of the subject. In some embodiments, the anti-PD-1 antibody or the anti-PD-1 antibody and anti-CTLA-4 antibody combination therapy of the present disclosure increases the progression-free survival of the subject. In certain embodiments, the anti-PD-1 antibody or the anti-PD-1 antibody and anti-CTLA-4 antibody combination therapy of the present disclosure increases the progression-free survival of the subject in comparison to standard-of-care therapies. In some embodiments, the anti-PD-1 antibody and anti-CTLA-4 antibody combination therapy of the present disclosure increases the progression-free survival of the subject in comparison to an anti-PD-1 antibody alone (i.e., anti-PD-1 antibody monotherapy). In some embodiments, the anti-PD-1 antibody and anti-CTLA-4 antibody combination therapy of the present disclosure increases the progression-free survival of the subject in comparison to other anti-PD-1 antibody combinations.

In some embodiments, after the administration of an anti-PD-1 antibody or administration of an anti-PD-1 antibody and an anti-CTLA-4 antibody, the subject having a tumor derived from an SCLC can exhibit an overall survival of at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months at least about 15 months, at least about 16 months, at least about 17 months, at least about 18 months, at least about 19 months, at least about 20 months, at least about 21 months, at least about 22 months, at least about 23 months, at least about 2 years, at least about 3 years, at least about 4 years, or at least about 5 years after the administration.

In other embodiments, after the administration of a therapy disclosed herein (e.g., an anti-PD-1 antibody therapy or an anti-PD-1 antibody and an anti-CTLA-4 antibody therapy), the duration of survival or the overall survival of the subject is increased by at least about 1 month, at least about 2 months, at least about 3 months, at least about 4 months, at least about 6 months, or at least about 1 year when compared to another subject treated with only a standard-of-care therapy (e.g., a platinum-based chemotherapy) or a different dosing schedule of the therapy. For example, the duration of survival or the overall survival of the subject treated with an anti-PD-1 antibody disclosed herein is increased by at least about 5%, at least about 10%, at least about 15%, at least about 20%, at least about 25%, at least about 30%, at least about 40%, at least about 50% or at least about 75% when compared to another subject treated with only a standard-of-care therapy (e.g., a platinum-based chemotherapy) or a different dosing schedule of the anti-PD-1 antibody therapy.

In other embodiments, after the administration of a combination therapy comprising an anti-PD-1 antibody and an anti-CTLA-4 antibody, the duration of survival or the overall survival of the subject is increased by at least about 1 month, at least about 2 months, at least about 3 months, at least about 4 months, at least about 6 months, or at least about 1 year when compared to another subject treated with only a standard-of-care therapy (e.g., a platinum-based chemotherapy), an anti-PD1 antibody alone, or a different dosing schedule of the combination therapy. For example, the duration of survival or the overall survival of the subject treated with an anti-PD-1 antibody and an anti-CTLA-4 antibody combination therapy disclosed herein is increased by at least about 5%, at least about 10%, at least about 15%, at least about 20%, at least about 25%, at least about 30%, at least about 40%, at least about 50% or at least about 75% when compared to another subject treated with only a standard-of-care therapy (e.g., a platinum-based chemotherapy), an anti-PD-1 antibody alone, or a different dosing schedule of the combination therapy.

In certain embodiments, the therapy of the present disclosure effectively increases the duration of progression free survival of the subject. In some embodiments, the subject exhibits a progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years.

In some embodiments, the anti-PD-1 and anti-CTLA-4 antibodies are formulated for intravenous administration. In certain embodiments, the anti-PD-1 and anti-CTLA-4 antibodies are administered sequentially. In embodiments, the anti-PD-1 and anti-CTLA-4 antibodies are administered within 30 minutes of each other. In one embodiment, the anti-PD-1 antibody is administered before the anti-CTLA-4 antibody. In another embodiment, the anti-CTLA-4 antibody is administered before the anti-PD-1 antibody. In another embodiment, the anti-PD-1 antibody and the anti-CTLA-4 antibody are administered concurrently in separate compositions. In a further embodiment, the anti-PD-1 antibody and the anti-CTLA-4 antibody are admixed as a single composition for concurrent administration.

In some embodiments, the anti-PD-1 antibody and anti-CTLA-4 antibody are administered in a fixed dose.

In some embodiments, the PD-L1 status of a tumor in a subject is measured prior to administering any composition or utilizing any method disclosed herein. In one embodiment, the PD-L1 expression level of a tumor is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, or greater than at least about 20%. In another embodiment, the PD-L1 status of a tumor is at least about 1%. In other embodiments, the PD-L1 status of the subject is at least about 5%. In a certain embodiment, the PD-L1 status of a tumor is at least about 10%.

In some embodiments, the median progression-free survival of a subject with a tumor that has ≥1% PD-L1 expression is at least about 1 week, at least about 2 weeks, at least about 3 weeks, at least about 4 weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 1 year longer than the median progression-free survival of a subject with a tumor with a <1% PD-L1 expression. In some embodiments, the progression-free survival of a subject with a tumor that has ≥1% PD-L1 expression is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 1 year, at least about eighteen months, at least about 2 years, at least about 3 years, at least about 4 years, or at least about 5 years.

In order to assess the PD-L1 expression, in one embodiment, a test tissue sample can be obtained from the patient who is in need of the therapy. In another embodiment, the assessment of PD-L1 expression can be achieved without obtaining a test tissue sample. In some embodiments, selecting a suitable patient includes (i) optionally providing a test tissue sample obtained from a patient with cancer of the tissue, the test tissue sample comprising tumor cells and/or tumor-infiltrating inflammatory cells; and (ii) assessing the proportion of cells in the test tissue sample that express PD-L1 on the surface of the cells based on an assessment that the proportion of cells in the test tissue sample that express PD-L1 on the cell surface is higher than a predetermined threshold level.

In any of the methods comprising the measurement of PD-L1 expression in a test tissue sample, however, it should be understood that the step comprising the provision of a test tissue sample obtained from a patient is an optional step. It should also be understood that in certain embodiments the "measuring" or "assessing" step to identify, or determine the number or proportion of, cells in the test tissue sample that express PD-L1 on the cell surface is performed by a transformative method of assaying for PD-L1 expression, for example by performing a reverse transcriptase-polymerase chain reaction (RT-PCR) assay or an IHC assay. In certain other embodiments, no transformative step is involved and PD-L1 expression is assessed by, for example, reviewing a report of test results from a laboratory. In certain embodiments, the steps of the methods up to, and including, assessing PD-L1 expression provides an intermediate result that may be provided to a physician or other healthcare provider for use in selecting a suitable candidate for the anti-PD-1 antibody or anti-PD-L1 antibody therapy. In certain embodiments, the steps that provide the intermediate result is performed by a medical practitioner or someone acting under the direction of a medical practitioner. In other embodiments, these steps are performed by an independent laboratory or by an independent person such as a laboratory technician.

In certain embodiments of any of the present methods, the proportion of cells that express PD-L1 is assessed by performing an assay to determine the presence of PD-L1 RNA. In further embodiments, the presence of PD-L1 RNA is determined by RT-PCR, in situ hybridization or RNase protection. In other embodiments, the proportion of cells that express PD-L1 is assessed by performing an assay to determine the presence of PD-L1 polypeptide. In further embodiments, the presence of PD-L1 polypeptide is determined by immunohistochemistry (IHC), enzyme-linked immunosorbent assay (ELISA), in vivo imaging, or flow cytometry. In some embodiments, PD-L1 expression is assayed by IHC. In other embodiments of all of these methods, cell surface expression of PD-L1 is assayed using, e.g., TIC or in vivo imaging.

Imaging techniques have provided important tools in cancer research and treatment. Recent developments in molecular imaging systems, including positron emission tomography (PET), single-photon emission computed tomography (SPECT), fluorescence reflectance imaging (FRI), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis and Weissleder, "In vivo imaging in cancer," *Cold Spring Harb. Perspect. Biol.* 2(12):a003848 (2010)). Antibody specificity, coupled with the sensitivity and resolution of PET, makes immunoPET imaging particularly attractive for monitoring and assaying expression of antigens in tissue samples (McCabe and Wu, "Positive progress in immunoPET—not just a coincidence," *Cancer Biother. Radiopharm.* 25(3):253-61 (2010); Olafsen et al., "ImmunoPET imaging of B-cell lymphoma using 124I-anti-CD20 scFv dimers (diabodies)," *Protein Eng. Des. Sel.* 23(4):243-9 (2010)). In certain embodiments of any of the present methods, PD-L1 expression is assayed by immuno-PET imaging. In certain embodiments of any of the present methods, the proportion of cells in a test tissue sample that express PD-L1 is assessed by performing an assay to determine the presence of PD-L1 polypeptide on the surface of cells in the test tissue sample. In certain embodiments, the test tissue sample is a FFPE tissue sample. In other embodiments, the presence of PD-L1 polypeptide is determined by IHC assay. In further embodiments, the IHC assay is performed using an automated process. In some embodiments, the IHC assay is performed using an anti-PD-L1 monoclonal antibody to bind to the PD-L1 polypeptide.

In one embodiment of the present methods, an automated IHC method is used to assay the expression of PD-L1 on the surface of cells in FFPE tissue specimens. This disclosure provides methods for detecting the presence of human PD-L1 antigen in a test tissue sample, or quantifying the level of human PD-L1 antigen or the proportion of cells in the sample that express the antigen, which methods comprise contacting the test sample, and a negative control sample, with a monoclonal antibody that specifically binds to human PD-L1, under conditions that allow for formation of a complex between the antibody or portion thereof and human PD-L1. In certain embodiments, the test and control tissue samples are FFPE samples. The formation of a complex is then detected, wherein a difference in complex formation between the test sample and the negative control sample is indicative of the presence of human PD-L1 antigen in the sample. Various methods are used to quantify PD-L1 expression.

In a particular embodiment, the automated IHC method comprises: (a) deparaffinizing and rehydrating mounted tissue sections in an autostainer; (b) retrieving antigen using a decloaking chamber and pH 6 buffer, heated to 110° C. for 10 min; (c) setting up reagents on an autostainer; and (d) running the autostainer to include steps of neutralizing endogenous peroxidase in the tissue specimen; blocking non-specific protein-binding sites on the slides; incubating the slides with primary antibody; incubating with a post-primary blocking agent; incubating with NovoLink Polymer; adding a chromogen substrate and developing; and counterstaining with hematoxylin.

For assessing PD-L1 expression in tumor tissue samples, a pathologist examines the number of membrane PD-L1$^+$ tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+ buckets, and then the intermediate 1+ and 2+ intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%. In one embodiment, the threshold number of cells that needs to be PD-L1 positive is at least about 100, at least about 125, at least about 150, at least about 175, or at least about 200 cells. In certain embodiments, the threshold number or cells that needs to be PD-L1 positive is at least about 100 cells.

Staining is also assessed in tumor-infiltrating inflammatory cells such as macrophages and lymphocytes. In most cases macrophages serve as an internal positive control since staining is observed in a large proportion of macrophages. While not required to stain with 3+ intensity, an absence of staining of macrophages should be taken into account to rule out any technical failure. Macrophages and lymphocytes are assessed for plasma membrane staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain embodiments of these scoring methods, the samples are scored by two pathologists operating independently, and the scores are subsequently consolidated. In certain other embodiments, the identification of positive and negative cells is scored using appropriate software.

A histoscore is used as a more quantitative measure of the IHC data. The histoscore is calculated as follows:

$$\text{Histoscore} = [(\% \text{ tumor} \times 1(\text{low intensity})) + (\% \text{ tumor} \times 2(\text{medium intensity})) + (\% \text{ tumor} \times 3(\text{high intensity}))]$$

To determine the histoscore, the pathologist estimates the percentage of stained cells in each intensity category within a specimen. Because expression of most biomarkers is heterogeneous the histoscore is a truer representation of the overall expression. The final histoscore range is 0 (no expression) to 300 (maximum expression).

An alternative means of quantifying PD-L1 expression in a test tissue sample IHC is to determine the adjusted inflammation score (AIS) score defined as the density of inflammation multiplied by the percent PD-L1 expression by tumor-infiltrating inflammatory cells (Taube et al., "Colocalization of inflammatory response with B7-h1 expression in human melanocytic lesions supports an adaptive resistance mechanism of immune escape," *Sci. Transl. Med.* 4(127):127ra37 (2012)).

The present methods can treat a tumor derived from an SCLC of any stages. There are at least nine stages used for SCLC: occult (hidden; TX, N0, and M0) stage, Stage 0 (carcinoma in situ; Tis, N0, and M0), Stage IA (T1a/T1b, N0, and M0), Stage IB (T2a, N0, M0), Stage IIA (T1a/T1b, N1, and M0; T2a, N1, and M0; or T2b, N0, and M0), Stage IIB (T2b, N1, and M0; or T3, N0, M0), Stage IIIA (T1-T3, N2, and M0; T3, N1, and M0; or T4, N0-N1, and M0), Stage IIIB (Any T, N3, M0; or T4, N2, and M0), and Stage IV (any T, any N, and M1a; or any T, any N, and M1b) (see, e.g., www.cancer.org/cancer/lungcancer-smallcell/detailedguide/small-cell-lung-cancer-staging, last visited Jun. 2, 2016). In the occult stage, the cancer cannot be seen by imaging or bronchoscopy. In Stage 0, cancer cells are found in the lining of the airways.

In one embodiment, the present methods treat a Stage I SCLC. Stage I SCLC is divided in Stage IA and IB. In Stage IA, the tumor is no larger than 3 cm across, has not reached the membranes that surround the lungs, does not affect the main branches of the bronchi, and has not spread to lymph nodes or distant sites. In Stage IB, one or more of the following is true: 1) the tumor is larger than 3 centimeters but not larger than 5 centimeters; 2) the cancer has spread to the main bronchus but is not within 2 cm of the carina; 3) the tumor has grown into the visceral pleura (the membranes surrounding the lungs) and is not larger than 5 cm; or 4) the tumor is partially clogging the airways (and is not larger than 5 cm).

In another embodiment, the methods of the present disclosure treat a Stage II SCLC. Stage II SCLC is divided into Stage IIA and IIB. In Stage IIA, the cancer has either spread to the lymph nodes within the lung and/or around the area where the bronchus enters the lung (hilar lymph nodes). If the cancer has spread to the lymph nodes, then the cancer can only have spread to the lymph nodes on the same side of the chest as the tumor. If the cancer has not spread to the lymph nodes, the cancer is Stage IIA if the cancer has spread to the area where the bronchus enters the lung and one or more of the following is true: 1) the tumor is larger than 3 centimeters and not larger than 5 centimeters; 2) the tumor has grown into a main bronchus, but is not within 2 cm of the carina (and it is not larger than 5 cm); 3) the tumor has grown into the visceral pleura (the membranes surrounding the lungs) and is not larger than 5 cm; or 4) the tumor is partially clogging the airways (and is not larger than 5 cm). The tumor is also considered Stage IIA if the cancer has not spread to the lymph nodes and one or more of the following is true: 1) the tumor is larger than 5 centimeters but not larger than 7 centimeters; 2) the cancer has spread to a main bronchus and is at least 2 centimeters away from where the carina; 3) the tumor has spread to the visceral pleura (the membranes surrounding the lungs); or 4) the tumor is partially clogging the airways (and is between 5 and 7 cm across). In stage IIB, the cancer has either spread to the lymph nodes or not. If the cancer has spread to the lymph nodes, then the cancer can only have spread to the lymph nodes on the same side of the chest as the tumor, the lymph nodes with cancer are within the lung or near the bronchus and one or more of the following is true: 1) the tumor is larger than 5 centimeters but not larger than 7 centimeters; 2) the tumor has spread to a main bronchus and is at least 2 centimeters away from where the carina; 3) the tumor has spread into the visceral pleura (the membranes surrounding the lungs) and is between 5 and 7 cm across; or 4) the cancer is partially clogging the airways (and is between 5 and 7 cm across). The tumor is also considered Stage IIB if the cancer has not spread to the lymph nodes and one or more of the following is true: 1) the tumor is larger than 7 centimeters; 2) the cancer has grown into the chest wall, the breathing muscle that separates the chest from the abdomen (diaphragm), the membranes surrounding the space between the lungs (mediastinal pleura), or membranes of the sac surrounding the heart (parietal pericardium); 3) the cancer invades a main bronchus and is closer than 2 cm (about ¾ inch) to the carina, but it does not involve the carina itself, 4) the cancer has grown into the airways enough to cause an entire lung to collapse or to cause pneumonia in the entire lung; or 5) two or more separate tumor nodules are present in the same lobe of a lung.

In other embodiments, any methods of the present disclosure treat Stage III SCLC, including Stage IIIA and/or Stage IIIB. Stage IIIA is divided into 3 sections. These 3 sections are based on 1) the size of the tumor; 2) where the tumor is found and 3) which (if any) lymph nodes have cancer. In the first type of Stage IIIA SCLC, the main tumor can be any size, and it has not grown into the space between the lungs (mediastinum), the heart, the large blood vessels near the heart (such as the aorta), the windpipe (trachea), the tube connecting the throat to the stomach (esophagus), the backbone, or the carina, nor has it spread to different lobes of the same lung. Further, the cancer has spread to lymph nodes around the carina (the point where the windpipe splits into the left and right bronchi) or in the space between the lungs (mediastinum), and these lymph nodes are on the same side as the main lung tumor, but the cancer has not spread to distant sites. In the second type of Stage IIIA SCLC, the cancer has spread to the lymph nodes on the same side of the chest as the tumor, and the lymph nodes with the cancer are within the lung or near the bronchus. Additionally: 1) the tumor is larger than 7 cm across; 2) the cancer has grown into the chest wall, the breathing muscle that separates the chest from the abdomen (diaphragm), the membranes surrounding the space between the lungs (mediastinal pleura), or membranes of the sac surrounding the heart (parietal pericardium); 3) the cancer invades a main bronchus and is closer than 2 cm to the carina, but it does not involve the carina itself, 4) two or more separate tumor nodules are present in the same lobe of a lung; and 5) the cancer has grown into the airways enough to cause an entire lung to collapse or to cause pneumonia in the entire lung. In the third type of Stage IIIA SCLC, the cancer may or may not have spread to lymph nodes within the lung and/or around the area where the bronchus enters the lung (hilar lymph nodes) and one or more of the following is true: 1) a tumor of any size has grown into the space between the lungs (mediastinum), the heart, the large blood vessels near the heart (such as the aorta), the windpipe (trachea), the tube connecting the throat to the stomach (esophagus), the backbone, or the carina; and/or 2) two or more separate tumor nodules are present in different lobes of the same lung.

Stage IIIB is divided into 2 sections depending on 1) the size of the tumor, 2) where the tumor is found, and 3) which lymph nodes have cancer. In the first type of Stage IIIB SCLC, the cancer can be of any size; it may or may not have grown into nearby structures or caused pneumonia or lung collapse; and it has spread to lymph nodes near the collarbone on either side, and/or has spread to hilar or mediastinal lymph nodes on the side opposite the primary tumor. But, the cancer has not spread to distant sites. In the second type of Stage IIIB SCLC, the cancer has also spread to lymph nodes around the carina (the point where the windpipe splits into the left and right bronchi) or in the space between the lungs (mediastinum). Affected lymph nodes are on the same side as the main lung tumor. It has not spread to distant sites. In addition, one or more of the following is true: 1) a tumor of any size has grown into the space between the lungs (mediastinum), the heart, the large blood vessels near the heart (such as the aorta), the windpipe (trachea), the tube connecting the throat to the stomach (esophagus), the backbone, or the carina; and/or 2) two or more separate tumor nodules are present in different lobes of the same lung In some embodiments, the methods of the disclosure treat a Stage IV SCLC. Stage IV SCLC is divided into 2 types. In the first type of Stage IV SCLC, the tumor may be any size and one or more of the following is true: 1) there are one or more tumors in both lungs; 2) cancer is found in the fluid around the lungs or heart. In the second type of Stave IV SCLC, the cancer can be any size and may or may not have grown into nearby structures or reached nearby lymph nodes, and it has spread to distant lymph nodes or to other organs such as the liver, bones, or brain.

Anti-PD-1 Antibodies or Anti-PD-L1 Antibodies

Anti-PD-1 antibodies suitable for use in the disclosed methods are antibodies that bind to PD-1 with high specificity and affinity, block the binding of PD-L1, and inhibit the immunosuppressive effect of the PD-1 signaling pathway. In any of the therapeutic methods disclosed herein, an anti-PD-1 or anti-PD-L1 "antibody" includes an antigen-binding portion that binds to the PD-1 or PD-L1 receptor, respectively, and exhibits the functional properties similar to those of whole antibodies in inhibiting ligand binding and upregulating the immune system. In certain embodiments, the anti-PD-1 antibody or antigen-binding portion thereof cross-competes with nivolumab for binding to human PD-1. In other embodiments, the anti-PD-L1 antibody or antigen-binding fragment thereof competes for binding with BMS-936559, MPDL3280A, MEDI4736, or MSB0010718C for binding to human PD-L1.

In other embodiments, the anti-PD-1 antibody, or anti-PD-L1 antibody, or antigen-binding portions thereof is a chimeric, humanized, or human monoclonal antibody or a portion thereof. In certain embodiments for treating a human subject, the antibody is a humanized antibody In other embodiments for treating a human subject, the antibody is a human antibody. Antibodies of an IgG1, IgG2, IgG3, or IgG4 isotype can be used.

In certain embodiments, the anti-PD-1 antibody, or anti-PD-L1 antibody, or antigen-binding portions thereof comprises a heavy chain constant region which is of a human IgG1 or IgG4 isotype. In certain other embodiments, the sequence of the IgG4 heavy chain constant region of the anti-PD-1 antibody, or anti-PD-L1 antibody, or antigen-binding portions thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al. In vitro characterization of the anti-PD-1 antibody nivolumab, BMS-936558, and in vivo toxicology in non-human primates, Cancer Imm Res, 2(9):846-56 (2014)). In yet other embodiments, the antibody comprises a light chain constant region which is a human kappa or lambda constant region. In other embodiments, the anti-PD-1 antibody, anti-PD-L1 antibody, or antigen-binding portions thereof is a monoclonal antibody or an antigen-binding portion thereof.

Human antibodies that bind specifically to PD-1 with high affinity have been disclosed in U.S. Pat. No. 8,008,449. Other anti-PD-1 monoclonal antibodies have been described in, for example, U.S. Pat. Nos. 6,808,710, 7,488,802, 8,168,757 and 8,354,509, and PCT Publication No. WO 2012/145493. Each of the anti-PD-1 human antibodies disclosed in U.S. Pat. No. 8,008,449 has been demonstrated to exhibit one or more of the following characteristics: (a) binds to human PD-1 with a $K_D$ of $1\times10^7$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and (j) inhibits tumor cell growth in vivo. Anti-PD-1 antibodies usable in the present disclosure include monoclonal antibodies that bind specifically to human PD-1 and exhibit at least one, in some embodiments, at least five, of the preceding characteristics. In some embodiments, the anti-PD-1 antibody is nivolumab. In one embodiment, the anti-PD-1 antibody is pembrolizumab.

In one embodiment, the anti-PD-1 antibody is nivolumab. Nivolumab (also known as "OPDIVO©"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al. In vitro characterization of the anti-PD-1 antibody nivolumab, BMS-936558, and in vivo toxicology in non-human primates, Cancer Imm Res, 2(9): 846-56 (2014)). In another embodiment, the anti-PD-1 antibody or fragment thereof cross-competes with nivolumab. In other embodiments, the anti-PD-1 antibody or fragment thereof binds to the same epitope as nivolumab. In certain embodiments, the anti-PD-1 antibody has the same CDRs as nivolumab.

In another embodiment, the anti-PD-1 antibody (or antigen-binding portion thereof) cross-competes with pembrolizumab. In some embodiments, the anti-PD-1 antibody or fragment thereof binds to the same epitope as pembrolizumab. In certain embodiments, the anti-PD-1 antibody has the same CDRs as pembrolizumab. In another embodiment, the anti-PD-1 antibody is pembrolizumab. Pembrolizumab (also known as "KEYTRUDA©", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also www.cancer.gov/drugdictionary?cdrid=695789 (last accessed: Dec. 14, 2014). Pembrolizumab has been approved by the FDA for the treatment of relapsed or refractory melanoma.

In other embodiments, the anti-PD-1 antibody (or antigen-binding portion thereof) cross-competes with MEDI0680. In still other embodiments, the anti-PD-1 antibody or fragment thereof binds to the same epitope as MEDI0680. In certain embodiments, the anti-PD-1 antibody has the same CDRs as MEDI0680. In other embodiments, the anti-PD-1 antibody is MEDI0680 (formerly AMP-514), which is a monoclonal antibody. MEDI0680 is described, for example, in U.S. Pat. No. 8,609,089B2 or in www.cancer.gov/drugdictionary?cdrid=756047 (last accessed Dec. 14, 2014).

In certain embodiments, the first antibody is an anti-PD-1 antagonist. One example of the anti-PD-1 antagonist is AMP-224, which is a B7-DC Fc fusion protein. AMP-224 is discussed in U.S. Publ. No. 2013/0017199 or in www.cancer.gov/publications/dictionaries/cancer-drug?cdrid=700595 (last accessed Jul. 8, 2015).

In other embodiments, the anti-PD-1 antibody (or antigen-binding portion thereof) cross-competes with BGB-A317. In some embodiments, the anti-PD-1 antibody or fragment thereof binds the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

In other embodiments, the anti-PD-1 antibody (or antigen-binding portion thereof) cross-competes with INCSHR1210 (SHR-1210). In some embodiments, the anti-PD-1 antibody binds to the same epitope as INCSHR1210 (SHR-1210). In certain embodiments, the anti-PD-1 antibody has the same CDRs as INCSHR1210 (SHR-1210). In certain embodiments, the anti-PD-1 antibody is INCSHR1210 (SHR-1210), which is a human monoclonal antibody. INCSHR1210 (SHR-1210) is described in WO2015/085847.

In other embodiments, the anti-PD-1 antibody (or antigen-binding portion thereof) cross-competes with REGN-2810. In some embodiments, the anti-PD-1 antibody binds to the same epitope as REGN-2810. In certain embodiments, the anti-PD-1 antibody has the same CDRs as REGN-2810. In certain embodiments, the anti-PD-1 antibody is REGN-2810, which is a human monoclonal antibody. REGN-2810 is described in WO2015/112800.

In other embodiments, the anti-PD-1 antibody (or antigen-binding portion thereof) cross-competes with PDR001. In some embodiments, the anti-PD-1 antibody binds to the same epitope as PDR001. In certain embodiments, the anti-PD-1 antibody has the same CDRs as PDR001. In certain embodiments, the anti-PD-1 antibody is PDR001, which is a humanized monoclonal antibody. PDR001 is described in WO2015/112900.

In other embodiments, the anti-PD-1 antibody (or antigen-binding portion thereof) cross-competes with TSR-042 (ANB 011). In some embodiments, the anti-PD-1 antibody binds to the same epitope as TSR-042 (ANB 011). In certain embodiments, the anti-PD-1 antibody has the same CDRs as TSR-042 (ANB 011). In certain embodiments, the anti-PD-1 antibody is TSR-042 (ANB 011), which is a humanized monoclonal antibody. TSR-042 (ANB 011) is described in WO2014/179664.

In other embodiments, the anti-PD-1 antibody (or antigen-binding portion thereof) cross-competes with STI-1110. In some embodiments, the anti-PD-1 antibody binds to the same epitope as STI-1110. In certain embodiments, the anti-PD-1 antibody has the same CDRs as STI-1110. In certain embodiments, the anti-PD-1 antibody is STI-1110, which is a human monoclonal antibody. STI-1110 is described in WO2014/194302.

Anti-PD-1 antibodies usable in the disclosed methods also include isolated antibodies that bind specifically to human PD-1 and cross-compete for binding to human PD-1 with nivolumab (see, e.g., U.S. Pat. Nos. 8,008,449 and 8,779,105; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 as, nivolumab are monoclonal antibodies. For administration to human subjects, these cross-competing antibodies are chimeric antibodies, or humanized or human antibodies. Such chimeric, humanized or human monoclonal antibodies can be prepared and isolated by methods well known in the art.

Anti-PD-1 antibodies usable in the methods of the disclosed disclosure also include antigen-binding portions of the above antibodies. It has been amply demonstrated that the antigen-binding function of an antibody can be performed by fragments of a full-length antibody Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab")$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, or any combination thereof.

Anti-PD-1 antibodies suitable for use in the disclosed compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and upregulating the immune system. In certain embodiments, the anti-PD-1 antibody or antigen-binding portion thereof cross-competes with nivolumab for binding to human PD-1. In other embodiments, the anti-PD-1 antibody or antigen-binding portion thereof is a chimeric, humanized, or human monoclonal antibody or a portion thereof. In certain embodiments, the antibody is a humanized antibody. In other embodiments, the antibody is a human antibody. Antibodies of an IgG1, IgG2, IgG3, or IgG4 isotype can be used.

In certain embodiments, the anti-PD-1 antibody or antigen-binding portion thereof comprises a heavy chain constant region which is of a human IgG1 or IgG4 isotype. In certain other embodiments, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al. (2014)). In yet other embodiments, the antibody comprises a light chain constant region which is a human kappa or lambda constant region. In other embodiments, the anti-PD-1 antibody or antigen-binding portion thereof is a monoclonal antibody or an antigen-binding portion thereof. In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0680 (formerly AMP-514), AMP-224, or BGB-A31

In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3, and 5F4 described in U.S. Pat. No. 8,008,449. In still other embodiments, the anti-PD-1 antibody is MEDI0680 (formerly AMP-514), or AMP-224.

In certain embodiments, an anti-PD-1 antibody used in the methods can be replaced with another PD-1 or anti-PD-L1 antagonist. For example, because an anti-PD-L1 antibody prevents interaction between PD-1 and PD-L1, thereby exerting similar effects to the signaling pathway of PD-1, an anti-PD-L1 antibody can replace the use of an anti-PD-1 antibody in the methods disclosed herein. Therefore, in one embodiment, the present disclosure is directed to a method for treating a subject afflicted with a tumor derived from an SCLC (e.g., a recurrent SCLC) comprising administering to the subject a therapeutically effective amount an anti-PD-L1 antibody. In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446 and atezolizumab) (see, e.g., Herbst et al. (2013) *J Clin Oncol* 31(suppl):3000. Abstract; U.S. Pat. No. 8,217,149), MEDI4736 (also called Durvalumab; Khleif (2013) In: Proceedings from the European Cancer Congress 2013; Sep. 27-Oct. 1, 2013; Amsterdam, The Netherlands. Abstract 802, See U.S. Pat. No. 8,779,108 or US 2014/0356353, filed May 6, 2014), or MSB0010718C (also called Avelumab; See US 2014/0341917). In other embodiments, the anti-PD-L1 antibody is CX-072 (also called CytomX; See WO2016/149201).

Combination Therapies with Anti-PD-1 or Anti-PD-L1 Antibodies

In certain embodiments, an anti-PD-1 antibody or anti-PD-L1 antibody is administered in combination with one or more other anti-cancer agents. In certain embodiments, the one or more anti-cancer agents have been administered to the subject prior to the administration of the anti-PD-1 or anti-PD-L1 antibodies or prior to the combination with the anti-PD-1 or anti-PD-L1 antibodies. In certain embodiments, the one or more anti-cancer agents were not effective in treating the cancer. In some embodiments, the other anti-cancer agent is any anti-cancer agent described herein or known in the art. In certain embodiments, the other anti-cancer agent is an anti-CTLA-4 antibody. In one embodiment, the other anti-cancer agent is a chemotherapy or a platinum-based doublet chemotherapy (PT-DC). In certain embodiments, the other anti-cancer agent is an EGFR-targeted tyrosine kinase inhibitor (TKI). In one embodiment, the other anti-cancer agent is an anti-VEGF antibody. In other embodiments, the anti-cancer agent is a platinum agent (e.g., cisplatin, carboplatin), a mitotic inhibitor (e.g., paclitaxel, albumin-bound paclitaxel, docetaxel, taxotere, docecad), a fluorinated Vinca alkaloid (e.g., vinflunine, javlor), vinorelbine, vinblastine, etoposide, or pemetrexed gemcitabin. In one embodiment, the other anticancer agent is 5-flurouracil (5-FU). In certain embodiments, the other anti-cancer agent is any other anti-cancer agent known in the art. In some embodiments, two or more additional anti-cancer agents are administered in combination with the anti-PD-1 or anti-PD-L1 antibody. In some embodiments, the PD-1 or PD-L1 antibody is combined with surgical resection and/or radiation therapy.

Anti-CTLA-4 Antibodies

Anti-CTLA-4 antibodies of the instant disclosure bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing, or prolonging an immune response.

Human antibodies that bind specifically to CTLA-4 with high affinity have been disclosed in U.S. Pat. Nos. 6,984,720 and 7,605,238. Other anti-CTLA-4 monoclonal antibodies have been described in, for example, U.S. Pat. Nos. 5,977,318, 6,051,227, 6,682,736, and 7,034,121. The anti-CTLA-4 human antibodies disclosed in U.S. Patent Nos. 6,984,720 and 7,605,238 have been demonstrated to exhibit one or more of the following characteristics: (a) binds specifically to human CTLA-4 with a binding affinity reflected by an equilibrium association constant ($K_a$) of at least about $10^7$ $M^{-1}$, or about $10^9$ $M^{-1}$, or about $10^{10}$ $M^{-1}$ to $10^{11}$ $M^{-1}$ or higher, as determined by Biacore analysis; (b) a kinetic association constant ($k_a$) of at least about $10^3$, about $10^4$, or about $10^5$ $m^{-1}$ $s^{-1}$; (c) a kinetic disassociation constant ($k_d$) of at least about $10^3$, about $10^4$, or about $10^5$ $m^{-1}$ $s^{-1}$; and (d) inhibits the binding of CTLA-4 to B7-1 (CD80) and B7-2 (CD86). Anti-CTLA-4 antibodies usable in the present disclosure include monoclonal antibodies that bind specifically to human CTLA-4 and exhibit at least one, at least two or, in one embodiment, at least three of the preceding characteristics. An exemplary clinical anti-CTLA-4 antibody is the human monoclonal antibody 10D1 (now known as ipilimumab and marketed as YERVOY©) as disclosed in U.S. Pat. No. 6,984,720. Ipilimumab is an anti-CTLA-4 antibody for use in the methods disclosed herein. Another anti-CTLA-4 antibody usable in the present methods is tremelimumab.

An exemplary clinical anti-CTLA-4 antibody is the human monoclonal antibody 10D1 (now known as ipilimumab and marketed as YERVOY©) as disclosed in U.S. Pat. No. 6,984,720. Ipilimumab is an anti-CTLA-4 antibody for use in the methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

Another anti-CTLA-4 antibody useful for the present methods is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

Anti-CTLA-4 antibodies usable in the disclosed methods also include isolated antibodies that bind specifically to human PD-1 and cross-compete for binding to human CTLA-4 with ipilimumab or tremelimumab or bind to the same epitope region of human CTLA-4 as ipilimumab or tremelimumab. In certain embodiments, the antibodies that cross-compete for binding to human CTLA-4 with, or bind to the same epitope region of human PD-1 as does ipilimumab or tremelimumab, are antibodies comprising a heavy chain of the human IgG1 isotype. For administration to human subjects, these cross-competing antibodies are chimeric antibodies, humanized antibodies, or human antibodies. Usable anti-CTLA-4 antibodies also include antigen-binding portions of the above antibodies such as Fab, F(ab")$_2$, Fd, or Fv fragments.

Ipilimumab (YERVOY©) is a fully human, IgG1 monoclonal antibody that blocks the binding of CTLA-4 to its B7 ligands, thereby stimulating T cell activation and improving overall survival (OS) in patients with advanced melanoma (Hodi et al. (2010) *N Engl J Med* 363:711-23). Concurrent therapy with nivolumab and ipilimumab in a Phase 1 clinical trial produced rapid and deep tumor regression in a substantial proportion of patients with advanced melanoma, and was significantly more effective than either antibody alone (Wolchok et al. (2013) *N Engl J Med* 369(2):122-33; WO 2013/173223). However, it was hitherto not known whether this combination of immunoregulatory antibodies would be similarly effective in other tumor types.

Combination of an Anti-PD-1 Antibody with an Anti-CTLA-4 Antibody for Treating SCLC This disclosure provides combination therapy methods for treating a tumor derived from an SCLC wherein an anti-PD-1 antibody is combined with another anti-cancer agent that is an antibody or an antigen-binding portion thereof that binds specifically to CTLA-4 and inhibits CTLA-4 activity. The combination of the anti-PD-1 antibody, nivolumab, and the anti-CTLA-4 antibody, ipilimumab, has been demonstrated herein (see Example 1) to produce early, durable antitumor activity in SCLC patients, particularly with specific dosing schedules. Accordingly, in certain embodiments, the anti-CTLA-4 antibody that is used in combination with the anti-PD-1 antibody is ipilimumab. In embodiments, the anti-CTLA-4 antibody is tremelimumab. In other embodiments, the anti-CTLA-4 antibody or antigen-binding portion thereof is an antibody or portion thereof that cross-competes with ipilimumab for binding to human CTLA-4. In certain other embodiments, the anti-CTLA-4 antibody or antigen-binding portion thereof is a chimeric, humanized or human monoclonal antibody or a portion thereof. In yet other embodiments, the anti-CTLA-4 antibody or antigen-binding portion thereof comprises a heavy chain constant region that is of a human IgG1 or IgG4 isotype. In some embodiments, the anti-CTLA-4 antibody comprises a heavy chain constant region that is of a human IgG1 isotype.

Because of durability of the clinical effect previously demonstrated with immunotherapy by inhibition of immune checkpoints (see, e.g., WO 2013/173223), the combination treatment can include, in alternative embodiments, a finite number of doses, e.g., about 1-10 doses, or can involve dosing at long intervals, e.g., once about every 3-6 months or once about every 1-2 years or longer intervals.

In certain embodiments of the present methods, the anti-PD-1 antibody is nivolumab. In other embodiments, it is pembrolizumab. In yet other embodiments, the anti-CTLA-4 antibody is ipilimumab. In further embodiments, the anti-CTLA-4 antibody is tremelimumab. Typically, the anti-PD-1 and anti-CTLA-4 antibodies are formulated for intravenous administration. In certain embodiments, when the anti-PD-1 and anti-CTLA-4 antibodies are administered in combination, they are administered within 30 minutes of each other. Either antibody can be administered first, that is, in certain embodiments, the anti-PD-1 antibody is administered before the anti-CTLA-4 antibody, whereas in other embodiments, the anti-CTLA-4 antibody is administered before the anti-PD-1 antibody. Typically, each antibody is administered by intravenous infusion over a period of 60 minutes. In certain embodiments, the anti-PD-1 and anti-CTLA-4 antibodies are administered concurrently, either admixed as a single composition in a pharmaceutically acceptable formulation for concurrent administration, or concurrently as separate compositions with each antibody in a pharmaceutically acceptable formulation.

In some embodiments, the anti-PD-1 antibody is administered at a dose of 1 mg/kg once every three weeks, and the anti-CTLA-4 antibody is administered at a dose of 3 mg/kg once every three weeks. In other embodiments, the 1 mg/kg dose of the anti-PD-1 antibody and the 3 mg/kg dose of the anti-CTLA-4 antibody are administered one dose for each, two doses for each, three doses for each, four doses for each, five doses for each, six doses for each, seven doses for each, eight doses for each, nine doses for each, or ten doses for each. In further embodiments, the combination therapy of the anti-PD-1 antibody and the anti-CTLA-4 antibody is followed by a monotherapy of an anti-PD-1 antibody, e.g., at a dose of 3 mg/kg once every two weeks.

In certain embodiments, the anti-PD-1 antibody or antigen-binding portion thereof is administered at a subtherapeutic dose. In certain other embodiments, the anti-CTLA-4 antibody or antigen-binding portion thereof is administered at a subtherapeutic dose. In further embodiments, both the anti-PD-1 antibody or antigen-binding portion thereof and the anti-CTLA-4 antibody or antigen-binding portion thereof are each administered at a subtherapeutic dose.

Standard-of-Care Therapies for SCLC

Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES® (2014), available at: www.nccn.org/professionals/physician_gls/f_guidelines.asp, last accessed Jun. 2, 2016).

Surgery, radiation therapy (RT), and chemotherapy are the three modalities commonly used to treat SCLC patients. The most commonly used initial chemotherapy regimen is etoposide (TOPOSAR® or VEPESID®) plus cisplatin (PLATINOL®), known as EP. For people with extensive-stage small cell lung cancer, chemotherapy alone using the EP regimen is the standard treatment. However, another regimen that may be used is carboplatin (PARAPLATIN®) plus irinotecan (CAMPTOSAR®).

Although SCLC is highly sensitive to initial treatments, including chemotherapy and/or radiotherapy, most patients ultimately die due to recurrence of the SCLC. Therefore, there is a particular unmet need among patients who have recurrent SCLC as there is a lack of an effective treatment after first line therapy.

Pharmaceutical Compositions and Dosages

Therapeutic agents of the present disclosure can be constituted in a composition, e.g., a pharmaceutical composition containing an antibody and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In one embodiment, the carrier for a composition containing an antibody is suitable for intravenous, intramuscular, subcutaneous, parenteral, spinal or epidermal administration (e.g., by injection or infusion). A pharmaceutical composition of the disclosure can include one or more pharmaceutically acceptable salts, anti-oxidant, aqueous and non-aqueous carriers, and/or adjuvants such as preservatives, wetting agents, emulsifying agents, and dispersing agents.

Dosage regimens are adjusted to provide the optimum desired response, e.g., a maximal therapeutic response and/or minimal adverse effects. For administration of an anti-PD-1 antibody, as a monotherapy or in combination with another anti-cancer agent (e.g., in combination with an anti-CTLA-4 antibody), the dosage can range from about 0.01 to about 20 mg/kg, about 0.1 to about 10 mg/kg, about 0.1 to about 5 mg/kg, about 1 to about 5 mg/kg, about 2 to about 5 mg/kg, about 7.5 to about 12.5 mg/kg, or about 0.1 to about 30 mg/kg of the subject's body weight. For example, dosages can be about 0.1, about 0.3, about 1, about 2, about 3, about 5 or about 10 mg/kg body weight, or about 0.3, about 1, about 2, about 3, or about 5 mg/kg body weight. The dosing schedule is typically designed to achieve exposures that result in sustained receptor occupancy (RO) based on typical pharmacokinetic properties of an antibody An exemplary treatment regime entails administration about once per week, once about every 2 weeks, once about every 3 weeks, once about every 4 weeks, once about a month, once about every 3-6 months or longer. In certain embodiments, an anti-PD-1 antibody such as nivolumab is administered to the subject once about every 2 weeks. In other embodiments, the antibody is administered once about every 3 weeks. The dosage and scheduling can change during a course of treatment. For example, a dosing schedule for anti-PD-1 monotherapy can comprise administering the antibody: (i) about every 2 weeks in about 6-week cycles; (ii) about every 4 weeks for about six dosages, then about every three months; (iii) about every 3 weeks; (iv) about 3 mg/kg to about 10 mg/kg once followed by about 1 mg/kg every about 2-3 weeks. Considering that an IgG4 antibody typically has a half-life of 2-3 weeks, a dosage regimen for an anti-PD-1 antibody of the disclosure comprises at least about 0.3 mg/kg to at least about 10 mg/kg body weight, at least about 1 mg/kg to at least about 5 mg/kg body weight, or at least about 1 mg/kg to at least about 3 mg/kg body weight via intravenous administration, with the antibody being given every about 14-21 days in up to about 6-week or about 12-week cycles until complete response or confirmed progressive disease. In certain embodiments, an anti-PD-1 monotherapy is administered at 3 mg/kg every 2 weeks until progressive disease or unacceptable toxicity. In some embodiments, the antibody treatment, or any combination treatment disclosed herein, is continued for at least about 1 month, at least about 3 months, at least about 6 months, at least about 9 months, at least about 1 year, at least about 18 months, at least about 24 months, at least about 3 years, at least about 5 years, or at least about 10 years.

When used in combinations with other cancer agents (e.g., in combination with an anti-CTLA-4 antibody), the dosage of an anti-PD-1 antibody can be lowered compared to the monotherapy dose. Dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some embodiments, a subtherapeutic dose is about 0.001 mg/kg to about 1 mg/kg, about 0.01 mg/kg to about 1 mg/kg, about 0.1 mg/kg to about 1 mg/kg, or about 0.001 mg/kg to about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%). In some embodiments, 0.3 mg/kg dosing can allow for sufficient exposure to lead to maximal biologic activity. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%) (Brahmer et al. (2010) *J Clin Oncol* 28:3167-75). Thus, 0.3 mg/kg dosing can allow for sufficient exposure to lead to maximal biologic activity.

Although higher nivolumab monotherapy dosing up to about 10 mg/kg every two weeks has been achieved without reaching the maximum tolerated does (MTD), the significant toxicities reported in other trials of checkpoint inhibitors plus anti-angiogenic therapy (see, e.g., Johnson et al. (2013) *Cancer Immunol Res* 1:373-77; Rini et al. (2011) *Cancer* 117:758-67) support the selection of a nivolumab dose lower than 10 mg/kg.

In certain embodiments, the dose of an anti-PD-1 antibody (or an anti-PD-L1 antibody) is a fixed dose in a pharmaceutical composition. In other embodiments, the method of the present disclosure can be used with a flat dose (a dose given to a patient irrespective of the body weight of the patient). For example, a flat dose of a nivolumab can be about 240 mg. For example, a flat dose of pembrolizumab can be about 200 mg. In embodiments, the anti-PD-1 antibody or antigen-binding portion thereof is administered at a dose of about 240 mg. In embodiments, the anti-PD-1 antibody or antigen-binding portion thereof is administered at a dose of about 360 mg. In embodiments, the anti-PD-1 antibody or antigen-binding portion thereof is administered at a dose of about 480 mg. In one embodiment, 360 mg of the anti-PD-1 antibody or antigen binding fragment is administered once every 3 weeks. In another embodiment, 480 mg of the anti-PD-1 antibody or antigen binding fragment is administered once every 4 weeks.

Ipilimumab (YERVOY®) is approved for the treatment of melanoma at 3 mg/kg given intravenously once every 3 weeks for 4 doses. Thus, in some embodiments, about 3 mg/kg is the highest dosage of ipilimumab used in combination with the anti-PD-1 antibody though, in certain embodiments, an anti-CTLA-4 antibody such as ipilimumab can be dosed within the range of about 0.3 to about 10 mg/kg, about 0.5 to about 10 mg/kg, about 0.5 to about 5 mg/kg, or about 1 to about 5 mg/kg body weight about every two or three weeks when combined with nivolumab. In other embodiments, ipilimumab is administered on a different dosage schedule from nivolumab. In some embodiments, ipilimumab is administered about every week, about every two weeks, about every three weeks, about every 4 weeks, about every five weeks, about every six weeks, about every seven weeks, about every eight weeks, about every nine weeks, about every ten weeks, about every eleven weeks, about every twelve weeks or about every fifteen weeks. Dosages of ipilimumab that are lower than the typical 3 mg/kg every 3 weeks, but not less than 0.001 mg/kg, are subtherapeutic dosages. The subtherapeutic doses of an anti-CTLA-4 antibody used in the methods herein are higher than 0.001 mg/kg and lower than 3 mg/kg. In some embodiments, a subtherapeutic dose is about 0.001 mg/kg to about 1 mg/kg, about 0.01 mg/kg to about 1 mg/kg, about 0.1 mg/kg to about 1 mg/kg, or about 0.001 mg/kg to about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. It has been shown that combination dosing of nivolumab at 3 mg/kg and ipilimumab at 3 mg/kg exceeded the MTD in a melanoma population, whereas a combination of nivolumab at 1 mg/kg plus ipilimumab at 3 mg/kg or nivolumab at 3 mg/kg plus ipilimumab at 1 mg/kg was found to be tolerable in melanoma patients (Wolchok et al., *N Engl J Med* 369(2):122-33(2013)). Accordingly, although nivolumab is tolerated up to 10 mg/kg given intravenously every 2 weeks, in certain embodiments doses of the anti-PD-1 antibody do not exceed about 3 mg/kg when combined with ipilimumab. In certain embodiments, based on risk-benefit and PK-PD assessments, the dosage used comprises a combination of nivolumab at about 1 mg/kg plus ipilimumab at about 3 mg/kg, nivolumab at about 3 mg/kg plus ipilimumab at about 1 mg/kg, or nivolumab at about 3 mg/kg plus ipilimumab at about 3 mg/kg is used, each administered at a dosing frequency of once about every 2-4 weeks, in certain embodiments, once about every 2 weeks or once about every 3 weeks. In certain other embodiments, nivolumab is administered at a dosage of about 0.1 mg/kg, about 0.3 mg/kg, about 1 mg/kg, about 2 mg/kg, about 3 mg/kg, or about 5 mg/kg in combination with ipilimumab administered at a dosage of about 0.1 mg/kg, about 0.3 mg/kg, about 1 mg/kg, about 2 mg/kg, about 3 mg/kg, or about 5 mg/kg, once about every 2 weeks, once about every 3 weeks, or once about every 4 weeks.

In certain embodiments, the combination of an anti-PD-1 antibody and an anti-CTLA-4 antibody is administered intravenously to the subject in an induction phase about every 2 or 3 weeks for 1, 2, 3 or 4 administrations. In certain embodiments, the combination of nivolumab and ipilimumab is administered intravenously in the induction phase about every 2 weeks or about every 3 weeks for about 4 administrations. The induction phase is followed by a maintenance phase during which only the anti-PD-1 antibody is administered to the subject at a dosage of about 0.1 mg/kg, about 0.3 mg/kg, about 1 mg/kg, about 2 mg/kg, about 3 mg/kg, about 5 mg/kg, or about 10 mg/kg about every two or three weeks for as long as the treatment proves efficacious or until unmanageable toxicity or disease progression occurs. In certain embodiments, nivolumab is administered during the maintenance phase at a dose of about 3 mg/kg body about every 2 weeks.

The antibodies disclosed herein can be administered according to a "treatment cycle" or a "cycle" (which terms are used interchangeably herein). As used herein, the term "cycle" refers to a course of treatment that is repeated on a regular schedule with periods of rest in between. For example, treatment given for one week followed by three weeks of rest is a treatment cycle. In one embodiment, the anti-PD-1 antibody and/or anti-CTLA-4 antibody is administered for at least 1, 2, 3, 4, 5, 6, 7, 8, 9, or 10 cycles. In a particular embodiment, the administration of the anti-PD-1 antibody and the anti-CTLA-4 antibody was repeated four times (4 cycles).

In certain embodiments, the anti-PD-1 antibody and the anti-CTLA-4 antibody is formulated as a single composition, wherein the dose of the anti-PD1 antibody and the dose of the anti-CTLA-4 antibody are combined at a ratio of 1:50, 1:40, 1:30, 1:20, 1:10. 1:5, 1:3, 1:1, 3:1, 5:1, 10:1, 20:1, 30:1, 40:1, or 50:1. In other embodiments, the dose of the anti-CTLA-4 antibody is a fixed dose. In certain embodiments, the dose of the anti-CTLA-4 antibody is a flat dose, which is given to a patient irrespective of the body weight. In a specific embodiment, the flat dose of the anti-CTLA-4 antibody is about 80 mg.

For combination of nivolumab with other anti-cancer agents, these agents are administered at their approved dosages. Treatment is continued as long as clinical benefit is observed or until unacceptable toxicity or disease progression occurs. Nevertheless, in certain embodiments, the dosages of these anti-cancer agents administered are significantly lower than the approved dosage, i.e., a subtherapeutic dosage, of the agent is administered in combination with the anti-PD-1 antibody The anti-PD-1 antibody can be administered at the dosage that has been shown to produce the highest efficacy as monotherapy in clinical trials, e.g., about 3 mg/kg of nivolumab administered once about every three weeks (Topalian et al., *N Engl J Med* 366:2443-54 (2012a); Topalian et al., *Curr Opin Immunol* 24:207-12 (2012b)), or at a significantly lower dose, i.e., at a subtherapeutic dose. In certain embodiments, the anti-PD-1 antibody is administered at about 3 mg/kg once about every three weeks.

Dosage and frequency vary depending on the half-life of the antibody in the subject. In general, human antibodies show the longest half-life, followed by humanized antibodies, chimeric antibodies, and non-human antibodies. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, or until the patient shows partial or complete amelioration of symptoms of disease. Thereafter, the patient can be administered a prophylactic regime.

Actual dosage levels of the active ingredient or ingredients in the pharmaceutical compositions of the present disclosure can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health, and prior medical history of the patient being treated, and like factors well known in the medical arts. A composition of the present disclosure can be administered via one or more routes of administration using one or more of a variety of methods well known in the art. As will be appreciated by the skilled artisan, the route and/or mode of administration will vary depending upon the desired results.

In one embodiment, a subject treated with an anti-PD-1 antibody and an anti-CTLA-4 antibody in combination can be further treated with an anti-PD-1 antibody monotherapy.

Because anti-PD-1 and anti-PD-L1 target the same signaling pathway and have been shown in clinical trials to exhibit similar levels of efficacy in a variety of cancers, including renal cell carcinoma (see Brahmer et al. (2012) *N Engl J Med* 366:2455-65; Topalian et al. (2012a) *N Engl J Med* 366:2443-54; WO 2013/173223), an anti-PD-L1 antibody may be substituted for the anti-PD-1 antibody in any of the therapeutic methods disclosed herein. In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446 and atezolizumab) (see, e.g., Herbst et al. (2013) *J Clin Oncol* 31(suppl):3000. Abstract; U.S. Pat. No. 8,217, 149) or MEDI4736 (Khleif (2013) In: Proceedings from the European Cancer Congress 2013; Sep. 27-Oct. 1, 2013; Amsterdam, The Netherlands. Abstract 802). In certain embodiments, the antibodies that cross-compete for binding to human PD-L1 with, or bind to the same epitope region of human PD-L1 as the above-references PD-L1 antibodies are monoclonal antibodies. For administration to human subjects, these cross-competing antibodies can be chimeric antibodies, or can be humanized or human antibodies. Such chimeric, humanized or human monoclonal antibodies can be prepared and isolated by methods well known in the art.

Kits

Also within the scope of the present disclosure are kits comprising an anti-PD-1 antibody and another anti-cancer agent for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a tumor derived from an SCLC, the kit comprising: (a) an amount ranging from about 4 mg to about 500 mg of a PD-1 antibody or an antigen-binding portion thereof, and (b) instructions for using the PD-1 antibody or an antigen-binding portion thereof in any method disclosed herein. This disclosure further provides a kit for treating a subject afflicted with a tumor derived from an SCLC, the kit comprising: (a) an amount ranging from about 4 mg to about 500 mg of a PD-1 antibody or an antigen-binding portion thereof, (b) an amount ranging from about 4 mg to about 500 mg of a CTLA-4 antibody or an antigen-binding portion thereof, and (c) instructions for using the PD-1 antibody or an antigen-binding portion thereof and the CTLA-4 antibody or an antigen-binding portion thereof in any method disclosed herein. In some embodiments, the kit contains the PD-1 antibody or an antigen-binding portion thereof and the CTLA-4 antibody or an antigen-binding portion thereof as separation compositions. In some embodiments, the kit contains the PD-1 antibody or an antigen-binding portion thereof and the CTLA-4 antibody or an antigen-binding portion thereof as a single composition. In certain embodiments, the anti-PD-1, and the anti-CTLA-4 antibody can be co-packaged in unit dosage form. In certain embodiments for treating human patients, the kit comprises an anti-human PD-1 antibody disclosed herein, e.g., nivolumab or pembrolizumab. In other embodiments, the kit comprises an anti-human CTLA-4 antibody disclosed herein, e.g., ipilimumab or tremelimumab.

The present disclosure is further illustrated by the following example that should not be construed as further limiting. The contents of all references cited throughout this application are expressly incorporated herein by reference.

Example 1

Small-cell lung cancer (SCLC), which accounts for approximately 14% of all lung cancers, is strongly associated with tobacco use and has high mutation rates without known oncogenic drivers. Most patients present with extensive-stage disease characterized by widespread metastases and poor survival. Although 35% to 86% of patients respond to first-line chemotherapy, disease progresses rapidly, and outcomes with second-line treatment are poor.

Standard first-line chemotherapy for SCLC is a platinum-etoposide doublet, with topotecan as second-line therapy in the United States (US) and European Union (EU) and amrubicin as second-line therapy in Japan. Though response rates with topotecan are 23% and 9% for platinum-sensitive and platinum-resistant/refractory patients, respectively, they are not durable.

Nivolumab, a fully human IgG4 programmed death 1 (PD-1) immune-checkpoint-inhibitor antibody, significantly improved overall survival and had a favorable safety profile compared with docetaxel in two phase 3 studies of patients with non-SCLC (NSCLC) who progressed after first-line platinum-based doublet chemotherapy, leading to its approval in the US for treatment of patients with metastatic NSCLC and in the EU for treatment of patients with locally advanced or metastatic squamous NSCLC. Ipilimumab, a fully human IgG1 cytotoxic T-lymphocyte antigen 4 (CTLA-4) immune-checkpoint inhibitor, significantly improved overall survival in two phase 3 studies in patients with advanced melanoma, leading to approval in the US and the EU for this indication.

Preclinical data indicate that the combination of PD-1 and CTLA-4 receptor blockade may improve antitumor activity, and the combination of nivolumab plus ipilimumab has demonstrated deep and durable responses in several tumor types. The combination of nivolumab plus ipilimumab is approved in the US for treatment of advanced melanoma. Based on the efficacy of combination treatment in melanoma, a clinical trial was designed as a phase 1/2 trial to investigate the activity and safety of nivolumab as monotherapy or in combination with ipilimumab in several advanced or metastatic tumor types. The evaluation of nivolumab monotherapy and the combination of nivolumab and ipilimumab in patients with advanced or metastatic solid tumors for which no standard of care in advanced lines of treatment exists will potentially generate evidence of antitumor activity as a basis for further clinical development in these tumor types. Here, we report activity, safety, and biomarker analyses for the SCLC cohort.

Methods

Study Design and Participants

This was an international phase 1/2, two-stage, open-label multi-arm trial. Patients with SCLC were enrolled at 23 sites in six countries (Finland, Germany, Italy, Spain, UK, and US). Eligible patients had histologically or cytologically-confirmed limited or extensive-stage SCLC, with progressive disease after at least one platinum-based chemotherapy regimen. Patients with platinum-sensitive or platinum-resistant disease (relapse ≥ or <90 days after, or during, chemotherapy, respectively) were eligible regardless of programmed death-ligand 1 (PD-L1) expression. Patients were ≥18 years of age, with an Eastern Cooperative Oncology Group (ECOG) performance status of 0 or 1 (0 to 5 scale: 0, no symptoms; 1, mild; higher numbers, greater tumor-related disability) and had adequate organ function. Patients were required to have measurable disease per the Response Evaluation Criteria in Solid Tumors (RECIST), version 1.1, and baseline tumor biopsy or archival tumor material available for biomarker analyses. Tumor material was acceptable from biopsies performed before the screening period if the biopsy was done up to 3 months prior to start of treatment and no other systemic cancer therapy was administered in that time. Baseline laboratory tests required to assess eligibility included white blood cell counts, neutrophils, platelets, haemoglobin, serum creatinine, alanine aminotransferase (ALT), aspartate aminotransferase (AST), total bilirubin, albumin, lipase, and amylase. Key exclusion criteria included active brain or leptomeningeal metastases, a history of autoimmune disease (except for vitiligo, type I diabetes mellitus, residual hypothyroidism due to autoimmune thyroiditis only requiring hormone replacement, or conditions not expected to recur in the absence of an external trigger), the need for immunosuppressive doses of systemic corticosteroids (>10 mg per day prednisone equivalents) 2 weeks prior to study drug administration, and prior treatment with antibodies that modulate T-cell function or checkpoint pathways. Patients were also excluded if they tested positive for hepatitis B virus or human immunodeficiency virus, and had unresolved toxicities from prior anticancer therapies.

Patient selection was not based on estimated survival. Median survival for patients with relapsed SCLC has been reported as approximately 3.5-12 months.

The study protocol was approved by an institutional review board or ethics committee at each participating center. The study was conducted in accordance with the Declaration of Helsinki and Good Clinical Practice guidelines, as defined by the International Conference on Harmonisation. Prior to performing any study-specific procedures, written informed consent was obtained from all patients.

Procedures

Considerations for the dosing in the combination cohorts were as follows: the 1 mg/kg nivolumab plus 3 mg/kg ipilimumab regimen is the approved dose for the treatment of advanced melanoma; the 3 mg/kg nivolumab plus 1 mg/kg ipilimumab regimen was chosen to maximize the nivolumab dose based on nivolumab exposure response data (1 mg/kg vs. 3 mg/kg); and to ensure that nivolumab plus ipilimumab is tolerable in patients with SCLC, an initial dose-escalating safety evaluation step was performed (starting with 1 mg/kg nivolumab plus 1 mg/kg ipilimumab). The safety of the 1 mg/kg nivolumab plus 3 mg/kg ipilimumab and the 3 mg/kg nivolumab plus 1 mg/kg ipilimumab regimens have been previously assessed in studies of other tumor types.

Patients with SCLC were assigned to one of the following treatment cohorts: nivolumab as monotherapy at 3 mg per kilogram of body weight (nivolumab-3) administered intravenously every 2 weeks or combination treatment of nivolumab plus ipilimumab administered intravenously every 3 weeks for 4 cycles, at dose level 1 (nivolumab 1 mg/kg+ipilimumab 1 mg/kg [nivolumab-1/ipilimumab-1]), dose level 2 (nivolumab 1 mg/kg+ipilimumab 3 mg/kg [nivolumab-1/ipilimumab-3]), or dose level 2b (nivolumab 3 mg/kg+ipilimumab 1 mg/kg [nivolumab-3/ipilimumab-1]), followed by 3 mg/kg of nivolumab every 2 weeks. See FIG. 1. To ensure that the planned combination regimens would be tolerable in patients with SCLC, an initial dose-escalating safety evaluation for the combination arms was conducted. The first dose cohort was level 1. If this was deemed tolerable, then level 2 was initiated. If dose level 2 was deemed not tolerable, dose level 2b was investigated. Once the highest dose level for further investigation was confirmed in the dose-escalating safety evaluation phase, the combination arms continued enrolling patients. Patients on active treatment needed to be followed up for at least 6 weeks after the start of study treatment before tolerability of a dose level was determined based on prespecified tolerability assessment criteria. However, tolerability beyond 6 weeks was also taken into consideration. For combination treatment, nivolumab was administered first (60-minute infusion), followed by ipilimumab (90-minute infusion), as per previous studies evaluating nivolumab plus ipilimumab. Patients received open-label treatment until disease progression or occurrence of unacceptable toxicity (FIG. 1). Treatment beyond RECIST, version 1.1-defined progression was permitted if the patient was tolerating and benefiting from treatment, based on investigator assessment. Using an interactive voice response system, patients were enrolled in one of the four cohorts in a sequential manner, or assigned if more than one cohort was open for enrollment. Patients progressing on nivolumab-3 could cross over to combination cohorts.

No dose reductions or modifications were permitted for nivolumab or ipilimumab. Criteria for dose delays (which were required for protocol-defined reasons) and treatment discontinuation are detailed in the appendix.

Tumor assessments by radiographic imaging were done at baseline, every 6 weeks for the first 24 weeks, and every 12 weeks thereafter until disease progression (investigator-assessed per RECIST, version 1.1-defined progression) or treatment discontinuation. Survival was monitored continuously while patients were on treatment and every 3 months after treatment discontinuation. Safety was evaluated throughout the study (Table 1), and adverse events were graded according to the National Cancer Institute's Common Terminology Criteria for Adverse Events, version 4.0.

TABLE 1

On-study safety assessment schedules in nivolumab and nivolumab/ipilimumab cohorts*

| Safety assessment | Timing Considerations | Nivolumab Monotherapy Day 1 Week 1, 3, 5, 7, 9, etc. | Nivolumab/Ipilimumab Week 1 to Week 12 Day 1 Week 1, 4, 7, 10 | Nivolumab/Ipilimumab Week 13 Onward Day 1 Week 13, 15, 17, 19, 21, etc. |
|---|---|---|---|---|
| Targeted physical examination | 72 hours prior to dosing | X | X (+ day 4, week 2, 5) | X |
| Vital signs and oxygen saturation | 72 hours prior to dosing | X | X (+ day 4, week 2, 5) | X |
| Physical measurements | Weight prior to dosing | X | X (+ day 4, week 2, 5) | X |
| Adverse events assessment | | continuously | continuously | continuously |
| Review of concomitant medications | | continuously | continuously | continuously |
| Laboratory tests* | 72 hours prior to dosing | X | X (+ day 4, week 2, 5) | X |
| Pregnancy test | 24 hours prior to dosing, for WOCBP only | X (baseline and every 4 weeks) | X (baseline and every 3 weeks) | X (baseline and every 4 weeks) |

*Complete blood count with differential, liver function tests, blood urea nitrogen or serum urea level, creatinine, albumin, calcium, magnesium, sodium, potassium, chloride, lactic acid dehydrogenase, glucose, amylase, lipase, and thyroid stimulating hormone.
WOCBP = women of child-bearing potential.
X = assessment to be performed.

Tumor PD-L1 protein expression was assessed retrospectively in pretreatment (archival or fresh) tumor biopsy specimens with the use of a validated, automated immunohistochemical assay (Dako North America, Carpinteria, Calif., USA) using a rabbit antihuman PD-L1 antibody (clone 28-8, Epitomics Inc, Burlingame, Calif., USA). Tumor PD-L1 expression was categorized as positive when staining of tumor-cell membranes (at any intensity) was observed at prespecified expression levels of $\geq 1\%$ or $\geq 5\%$ of tumor cells in a section that included $\geq 100$ evaluable tumor cells. In the initial study protocol, analysis of the specimen was not required in advance of patient randomization; the protocol was later revised and this was made a requirement via a study amendment (for all cohorts of the study).

Outcomes

The primary endpoint of this study was the proportion of patients with a confirmed objective response (defined as the number of patients with a best overall response of complete response or partial response [as per investigator-assessed RECIST, version 1.1 criteria] divided by the number of assigned patients). The objective response rate was the primary endpoint as the trial objective was to evaluate antitumor activity of nivolumab monotherapy or in combination with ipilimumab.

The secondary endpoints included overall survival, progression-free survival, duration of response, and the rate of treatment-related adverse events leading to treatment discontinuation. Overall survival was defined as the time between the date of treatment assignment and the date of death due to any cause. Progression-free survival was defined as the time from treatment assignment to the date of the first documented tumor progression, as determined by the investigator (per RECIST, version 1.1), or death due to any cause, whichever occurred first. Duration of response was defined as the time from a best overall response of partial or complete response until the date progressive disease was documented (using RECIST version 1.1) or death due to any cause. The correlation between PD-L1 expression by tumor cells and antitumor activity was a prespecified exploratory endpoint.

All activity analyses were performed on the basis of the original treatment assignment, not by crossover status.

Statistical Analysis

In parallel to the safety evaluation phase for the combination arms (as described in Procedures), enrollment of patients followed a Simon two-stage design (see Simon R., Control *Clin. Trials* 10:1-10 (1989)). This design was used to test whether nivolumab and/or the combination of nivolumab and ipilimumab yields an objective response rate that is of clinical interest in each of the tumor types; it also limits the expected number of patients who receive treatment when the true response rate is not of clinical value. The two-stage test was conducted independently in each cohort.

For each cohort, the Simon design requires 18 treated patients for the first stage and calls for termination of a cohort at stage 1 if there is less than one responder among the 18 treated patients within the cohort. Otherwise, if two or more responders are identified in up to 18 patients in a cohort, additional patients will be assigned, to a total of 40 treated patients in that cohort. The treatment will be considered of clinical interest if, at the end of the second stage, there are eight or greater responders among 40 treated patients in any single cohort.

Only treatment arms that met an objective response rate threshold proceeded from stage 1 to stage 2. Enrollment in stage 2 in a given treatment arm could continue even if the other treatment arm was still in stage 1.

For stage 2, upon completion of enrollment for the initial 40 patients, additional patients were assigned into the nivolumab monotherapy arm and the combination arms up to a total of 100 patients (including those assigned in stage 1) in each treatment arm. When nivolumab monotherapy or nivolumab-1/ipilimumab-3 proceeded to stage 2, assessment of dose level 2b in stage 2 (nivolumab-3/ipilimumab-1) was initiated.

All analyses included treated patients who were enrolled at least 90 days prior to database lock. All activity analyses were performed on the basis of the original treatment assignment, not by crossover status.

Objective response rates were summarized by a binomial response rate and corresponding two-sided 95% exact confidence interval (CI) using the Clopper-Pearson method. Progression-free survival and overall survival were summarized descriptively using Kaplan-Meier methodology; median values were estimated with two-sided 95% CIs, calculated using the Brookmeyer-Crowley method. Only treatment cohorts with more than six patients are represented in Kaplan-Meier plots. Patient with less than 12 weeks follow-up were excluded from Kaplan-Meier plots. Progression-free survival and overall survival rates were also estimated with two-sided 95% CIs, calculated using the Greenwood formula. Duration of response was summarized using the Kaplan-Meier product-limit method. For PD-L1 biomarker analysis, best overall response was summarized for each cohort by baseline PD-L1 expression and objective response rates, with exact 95% CIs computed using the Clopper-Pearson method. All statistical analyses were performed using SAS software (version 9.02).

Results

We enrolled and treated 216 patients with SCLC: 98 patients in the nivolumab 3 mg/kg cohort, three patients in the nivolumab 1 mg/kg plus ipilimumab 1 mg/kg cohort, 61 patients in the nivolumab 1 mg/kg plus ipilimumab 3 mg/kg cohort, and 54 in the nivolumab 3 mg/kg plus ipilimumab 1 mg/kg cohort (FIG. 1). Three patients in the nivolumab 3 mg/kg group, two patients in the nivolumab 1 mg/kg plus ipilimumab 3 mg/kg group, and four patients in the nivolumab 3 mg/kg plus ipilimumab 1 mg/kg group did not receive first-line platinum therapy and did not meet eligibility criteria, but received treatment. None of the three patients in the nivolumab 1 mg/kg plus ipilimumab 1 mg/kg cohort permanently discontinued due to treatment-related adverse events within the first 6 weeks, allowing for enrollment in the other two combination cohorts: nivolumab 1 mg/kg plus ipilimumab 3 mg/kg, and nivolumab 3 mg/kg plus ipilimumab 1 mg/kg. At database lock, all patients had at least 12 weeks of follow-up; median follow-up for patients continuing in the study (including those who had died or discontinued treatment) was 198.5 days (IQR 163.0-464.0) in the nivolumab 3 mg/kg cohort, 302 days (IQR not calculable) in the nivolumab 1 mg/kg plus ipilimumab 1 mg/kg cohort, 361.0 days (273.0-470.0) in the nivolumab 1 mg/kg plus ipilimumab 3 mg/kg cohort, and 260.5 days (248.0-288.0) in the nivolumab 3 mg/kg plus ipilimumab 1 mg/kg cohort (Table 2). Median follow-up for the overall survival data is shown in the appendix (Table 2). Baseline characteristics are shown in Table 3; roughly half of patients had been treated with two or more previous regimens, and about a third had platinum-resistant disease.

TABLE 2

| Treatment exposure and patient disposition | | | |
|---|---|---|---|
| | Nivolumab-3 (n = 98) | Nivolumab-1/ Ipilimumab-3 (n = 61) | Nivolumab-3/ Ipilimumab-1 (n = 54) |
| Median number of infusions | | | |
| Nivolumab | 3.5 (2.0-6.0) | 3.0 (2.0-14.0) | 2.0 (2.0-6.0) |
| Ipilimumab | NA | 3.0 (2.0-4.0) | 2.0 (2.0-4.0) |
| Median follow-up, days* | 198.5 (163.0-464.0) | 361.0 (273.0-470.0) | 260.5 (248.0-288.0) |
| Median follow-up for overall survival, days** | 338.5 (303.0-604.0) | 501.0 (413.0-610.0) | 400.0 (387.0-428.0) |
| Pts Continuing Treatment | 21 (21%) | 19 (31%) | 11 (20%) |
| Pts not Continuing Treatment | 77 (79%)† | 42 (69%) | 43 (80%) |
| Progressive disease | 57 (58%) | 26 (43%) | 36 (67%) |
| AE related to study drug | 4 (4%) | 7 (11%) | 4 (7%) |
| AE unrelated to study drug | 10 (10%) | 5 (8%) | 1 (2%) |

TABLE 2-continued

| Treatment exposure and patient disposition | | | |
|---|---|---|---|
| | Nivolumab-3 (n = 98) | Nivolumab-1/ Ipilimumab-3 (n = 61) | Nivolumab-3/ Ipilimumab-1 (n = 54) |
| Death | 0 | 2 (3%) | 0 |
| Patient request/ withdrew consent | 5 (5%) | 1 (2%) | 2 (4%) |
| Other | 1 (1%) | 1 (2%) | 0 |
| Patients continuing to be followed‡ | 66 (67%) | 48 (79%) | 44 (82%) |
| Deaths | 48 (49%) | 30 (49%) | 25 (46%) |

Data presented as n, n (%) or median (IQR) unless otherwise stated. All patients were enrolled at least 90 days prior to database lock. AE = adverse event. IQR = interquartile range NA = not applicable.
*Patients continuing in the study at the time of the Nov. 6, 2015 database lock.
**Patients continuing in the study at the time of the Mar. 24, 2016 database lock (n = 98, nivolumab-3; n = 61, nivolumab-1/ipilimumab-3; n = 55, nivolumab-3/ipilimumab-1).
†One patient with disease progression and one patient who requested to discontinue treatment had treatment-related adverse events that contributed to discontinuation from treatment in the nivolumab-3 cohort.
‡Includes patients still on treatment and patients off treatment continuing in the follow-up period.

TABLE 3

| Baseline patient characteristics | | | | |
|---|---|---|---|---|
| Baseline Characteristics | Nivolumab-3 (n = 98) | Nivolumab-1/ Ipilimumab-1 (N = 3) | Nivolumab-1/ Iipilimumab-3 (n = 61) | Nivolumab-3/ Ipilimumab-1 (n = 54) |
| Median age (IQR), years | 63 (57-68) | 61(52-65) | 66 (58-71) | 61 (56-65) |
| Age ≥75 | 9 (9%) | 0 | 7 (11%) | 0 |
| Sex | | | | |
| Male | 61 (62%) | 2 (67%) | 35 (57%) | 32 (59%) |
| Female | 37 (38%) | | 26 (43%) | 22 (41%) |
| Race | | | | |
| White | 91 (93%) | 2 (67%) | 60 (98%) | 52 (96%) |
| Black/African American | 3 (3%) | 1 (33%) | 1 (2%) | 0 |
| Other | 4 (4%) | 0 | 0 | 1 (2%) |
| Not reported | 0 | 0 | 0 | 1 (2%) |
| Prior treatment regimens | | | | |
| 1 | 40 (41%) | 1 (33%) | 32 (52%) | 23 (43%) |
| 2-3 | 55 (56%) | 2 (67%) | 23 (38%) | 28 (52%) |
| >3 | 3 (3%) | 0 | 6 (10%) | 3 (6%) |
| First-line platinum-treated patients* | | | | |
| Platinum sensitive | 55 (56%) | 1 (33%) | 25 (41%) | 21 (39%) |
| Platinum resistant | 30 (31%) | 0 | 23 (38%) | 21 (39%) |
| Unknown | 10 (10%) | 2 (67%) | 11 (18%) | 8 (15%) |
| Smoking Status | | | | |
| Current or former smoker | 95 (97%) | 3 (100%) | 57 (93%) | 48 (89%) |
| Never smoked | 3 (3%) | | 4 (7%) | 5 (9%) |
| Unknown | 0 | | 0 | 1 (2%) |
| PD-L1 expression level‡ | | | | |
| ≥1% | 10 (14%) | 1 (50%) | 9 (24%) | 5 (13%) |
| <1% | 59 (86%) | 1 (50%) | 28 (76%) | 35 (88%) |
| ≥5% | 4 (6%) | 0 | 2 (5%) | 1 (3%) |
| <5% | 65 (94%) | 2 (100%) | 35 (95%) | 39 (98%) |
| Indeterminate/ not evaluable/missing | 29 (30%) | 1 (33%) | 24 (39%) | 14 (26%) |

Data presented as n (%) or median (IQR) unless otherwise stated.
*Three patients in the nivolumab 3 mg/kg group, two patients in the nivolumab 1 mg/kg plus ipilimumab 3 mg/kg group, and four patients in the nivolumab 3 mg/kg plus ipilimumab 1 mg/kg group did not receive first-line platinum therapy and did not meet eligibility criteria, although they were treated and included in the analysis.
†Defined as a patient who relapsed <90 days after chemotherapy.
‡Percentage of PD-L1 evaluable patients; may exceed 100% due to rounding.

Patients received a median of 3 to 5 infusions of nivolumab (IQR 2.0-6.0) in the nivolumab 3 mg/kg cohort, 9.0 infusions of nivolumab (IQR not calculable) and 4.0 infusions of ipilimumab (IQR not calculable) in the nivolumab 1 mg/kg plus ipilimumab 1 mg/kg cohort, 3•0 infusions each of nivolumab (2.0-14.0) and ipilimumab (2.0-4.0) in the nivolumab 1 mg/kg plus ipilimumab 3 mg/kg cohort, and 2.0 infusions each of nivolumab (2.0-6.0) and ipilimumab (2.0-4.0) in the nivolumab 3 mg/kg plus ipilimumab 1 mg/kg cohort. At the time of analysis, 77 (79%) patients had discontinued nivolumab 3 mg/kg, 42 (69%) had discontinued nivolumab 1 mg/kg plus ipilimumab 3 mg/kg, and 43 (80%) had discontinued nivolumab 3 mg/kg plus ipilimumab 1 mg/kg; the most common reason was disease progression (FIG. 1; Table 4). Two patients discontinued nivolumab 1 mg/kg plus ipilimumab 1 mg/kg (one due to disease progression, and one due to adverse event not related to study drug).

plus ipilimumab 3 mg/kg cohort, five patients died before disease assessment, one patient discontinued early due to clinical progression, one patient was not evaluable because the first assessment was not performed, and one patient withdrew consent for scans and follow-up visits; and in the nivolumab 3 mg/kg plus ipilimumab 1 mg/kg cohort, two patients died before disease assessment, three patients discontinued early (two due to clinical progression and one due to toxicity), and a CT scan was not performed on one patient. The median duration of response was not reached (95% CI 4.4—not reached) with nivolumab 3 mg/kg, 7.7 months (4.0—not reached) with nivolumab 1 mg/kg plus ipilimumab 3 mg/kg, and 4.4 months (3.7—not reached) with nivolumab 3 mg/kg plus ipilimumab 1 mg/kg. 16 patients had a duration of response longer than 6 months: six patients in the nivolumab 3 mg/kg group, one patient in the nivolumab 1 mg/kg plus ipilimumab 1 mg/kg group, eight patients in the nivolumab 1 mg/kg plus ipilimumab 3 mg/kg

TABLE 4

Treatment exposure and patient disposition.

|  | Nivolumab-3 (n = 98) | Nivolumab-1/ Ipilimumab-3 (n = 61) | Nivolumab-3/ Ipilimumab-1 (n = 54) |
| --- | --- | --- | --- |
| Median number of infusions |  |  |  |
| Nivolumab | 3.5 (2.0-6.0) | 3.0 (2.0-14.0) | 2.0 (2.0-6.0) |
| Ipilimumab | NA | 3.0 (2.0-4.0) | 2.0 (2.0-4.0) |
| Median follow-up, days* | 198.5 (163.0-464.0) | 361.0 (273.0-470.0) | 260.5 (248.0-288.0) |
| Median follow-up for OS, days** | 338.5 (303.0-604.0) | 501.0 (413.0-610.0) | 400.0 (387.0-428.0) |
| Patients continuing treatment | 21 (21%) | 19 (31%) | 11 (20%) |
| Patients not continuing treatment | 77 (79%)† | 42 (69%) | 43 (80%) |
| Progressive disease | 57 (58%) | 26 (43%) | 36 (67%) |
| AE related to study drug | 4 (4%) | 7 (11%) | 4 (7%) |
| AE unrelated to study drug | 10 (10%) | 5 (8%) | 1 (2%) |
| Death | 0 | 2 (3%) | 0 |
| Patient request/ withdrew consent | 5 (5%) | 1 (2%) | 2 (4%) |
| Other | 1 (1%) | 1 (2%) | 0 |
| Patients continuing to be followed‡ | 66 (67%) | 48 (79%) | 44 (82%) |
| Deaths | 48 (49%) | 30 (49%) | 25 (46%) |

Data presented as n, n (%) or median (IQR) unless otherwise stated. All patients were enrolled at least 90 days prior to database lock. AE = adverse event. IQR = interquartile range NA = not applicable.
*Patients continuing in the study at the time of the Nov. 6, 2015 database lock.
**Patients continuing in the study at the time of the Mar. 24, 2016 database lock (n = 98, nivolumab-3; n = 61, nivolumab-1/ipilimumab-3; n = 55, nivolumab-3/ipilimumab-1).
†One patient with disease progression and one patient who requested to discontinue treatment had treatment-related adverse events that contributed to discontinuation from treatment in the nivolumab-3 cohort.
‡Includes patients still on treatment and patients off treatment continuing in the follow-up period.

Figure 3A:
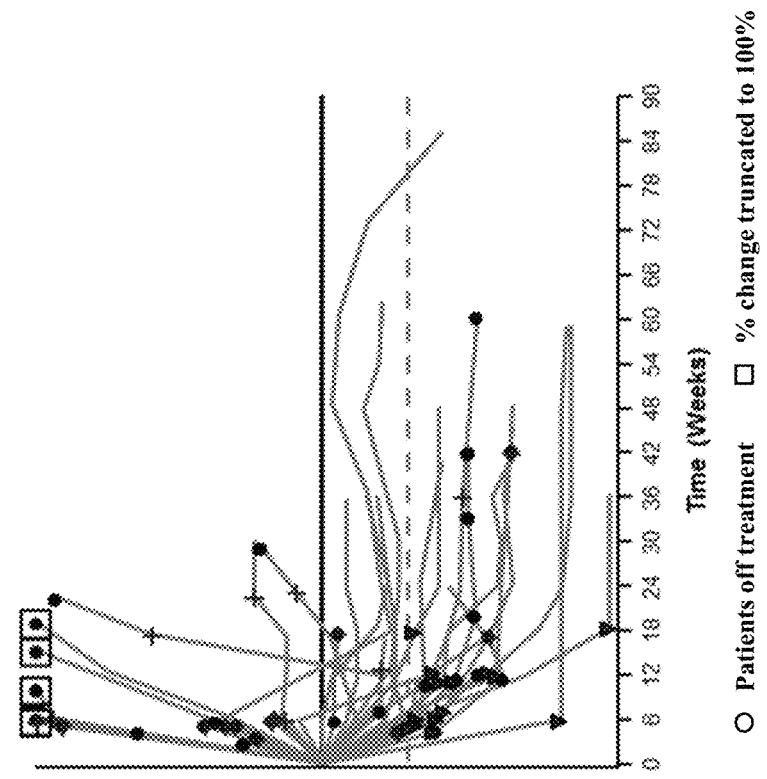
Figure 3B:
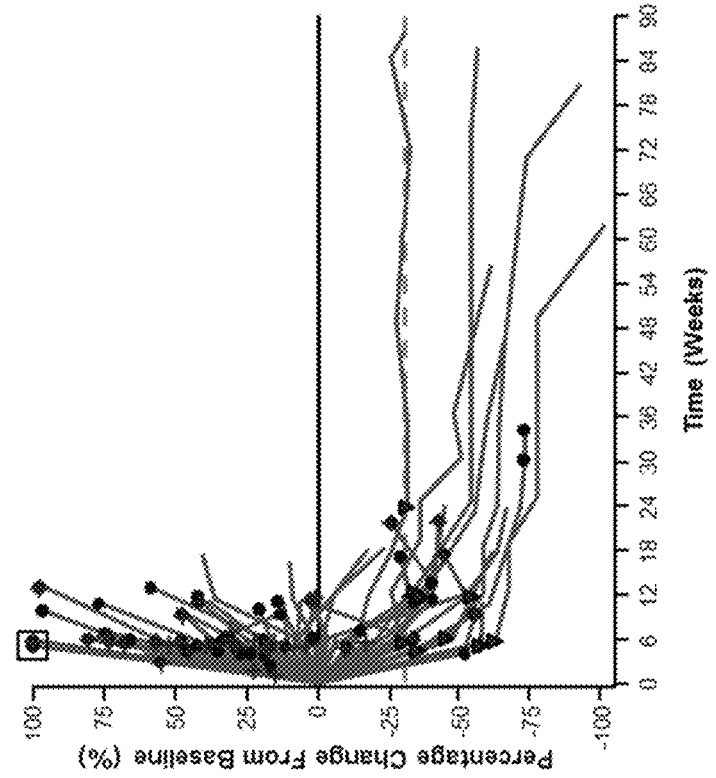

By blinded independent central review, ten (10% [95% CI 5-18]) of 98 patients achieved a confirmed objective response with nivolumab 3 mg/kg, 14 (23% [13-36]) of 61 with nivolumab 1 mg/kg plus ipilimumab 3 mg/kg, and ten (19% [9-31]) of 54 with nivolumab 3 mg/kg plus ipilimumab 1 mg/kg (Table 5; FIGS. 3A-3C). One (33%) of three patients receiving nivolumab 1 mg/kg plus ipilimumab 1 mg/kg achieved an objective response (complete response; data not shown). The predefined threshold that two or more of 18 patients in a particular group must have confirmed partial or complete response before continued enrollment for that group in stage 2 was met. In the nivolumab 3 mg/kg cohort, seven patients died before disease assessment, four patients discontinued early (one due to toxicity, three due to clinical progression), and one patient withdrew consent before completing the protocol; in the nivolumab 1 mg/kg group, and one patient in the nivolumab 3 mg/kg plus ipilimumab 1 mg/kg group (median 9.6 months [IQR 7.1-14.3]). Median time to response is shown in Table 5. At the time of database lock, eight (80%) of ten responses in the nivolumab 3 mg/kg group, one of three responses in the nivolumab 1 mg/kg plus ipilimumab 1 mg/kg group, seven (50%) of 14 responses in the nivolumab 1 mg/kg plus ipilimumab 3 mg/kg group, and seven (70%) of ten responses in the nivolumab 3 mg/kg plus ipilimumab 1 mg/kg group were ongoing. 30 patients in the nivolumab 3 mg/kg cohort, 15 in the nivolumab 1 mg/kg plus ipilimumab 3 mg/kg cohort, and six in the nivolumab 3 mg/kg plus ipilimumab 1 mg/kg cohort continued treatment beyond progression.

TABLE 5

Tumor Response.

|  | Nivolumab-3 (n = 98) | Nivolumab-1/ Ipilimumab-3 (n = 61) | Nivolumab-3/ Ipilimumab-1 (n = 54) |
|---|---|---|---|
| Objective response; 95% CI | 10 (10%; 5-18) | 14 (23%; 13-36) | 10 (19%; 9-31) |
| Best overall response |  |  |  |
| Complete response | 0 | 1 (2%) | 0 |
| Partial response | 10 (10%) | 13 (21%) | 10 (19%) |
| Stable disease | 22 (22%) | 13 (21%) | 9 (17%) |
| Progressive disease | 52 (53%) | 23 (38%) | 29 (54%) |
| Unable to determine | 12 (12%) | 8 (13%) | 6 (11%) |
| Not reported | 2 (2%) | 3 (5%) | 0 |
| Time to objective response (IQR), months | 2.0 (1.3-2.8) | 2.1 (1.4-2.8) | 1.4 (1.3-2.7) |

Data are n (%) unless otherwise stated. All patients were enrolled at least 90 days prior to database lock.

Figure 4A:
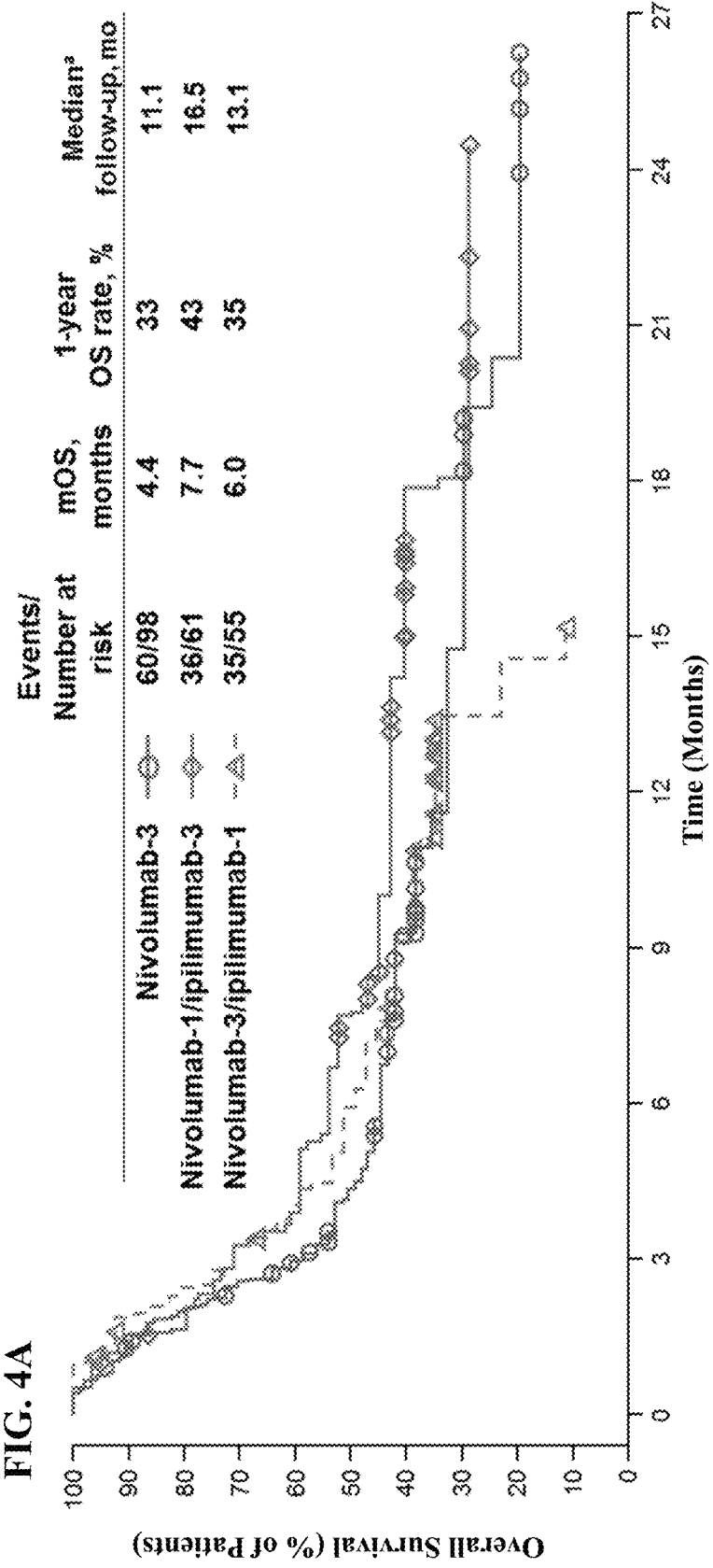
FIGS. 4A and 4B provide Kaplan-Meier curves of overall survival (FIG. 4A) and progression-free survival (FIG. 4B) for subjects treated with nivolumab 3 mg/kg (circles), nivolumab 1 mg/kg plus ipilimumab 3 mg/kg (diamonds), and nivolumab 3 mg/kg plus ipilimumab 1 mg/kg (triangles). The numbers of subjects at risk and the numbers of censored patients are shown for each treatment below the y-axes (FIGS. 4A and 4B).

As of the database lock on Mar. 24, 2016, 60 (61%) of 98 patients in the nivolumab 3 mg/kg cohort, 36 (59%) of 61 in the nivolumab 1 mg/kg plus ipilimumab 3 mg/kg, and 35 (64%) of 55 in the nivolumab 3 mg/kg plus ipilimumab 1 mg/kg had died. Median overall survival was 4.4 months (95% CI 3.0-9.3) in the nivolumab 3 mg/kg cohort, 7.7 months (3.6-18.0) in the nivolumab 1 mg/kg plus ipilimumab 3 mg/kg cohort, and 6.0 months (3.6-11.0) in the nivolumab 3 mg/kg plus ipilimumab 1 mg/kg cohort. 1-year overall survival was 33% (95% CI 22-45) for the nivolumab 3 mg/kg cohort, 43% (30-56) for the nivolumab 1 mg/kg plus ipilimumab 3 mg/kg cohort, and 35% (22-48) for the nivolumab 3 mg/g plus ipilimumab 1 mg/kg cohort (FIG. 4A).

Figure 4B:
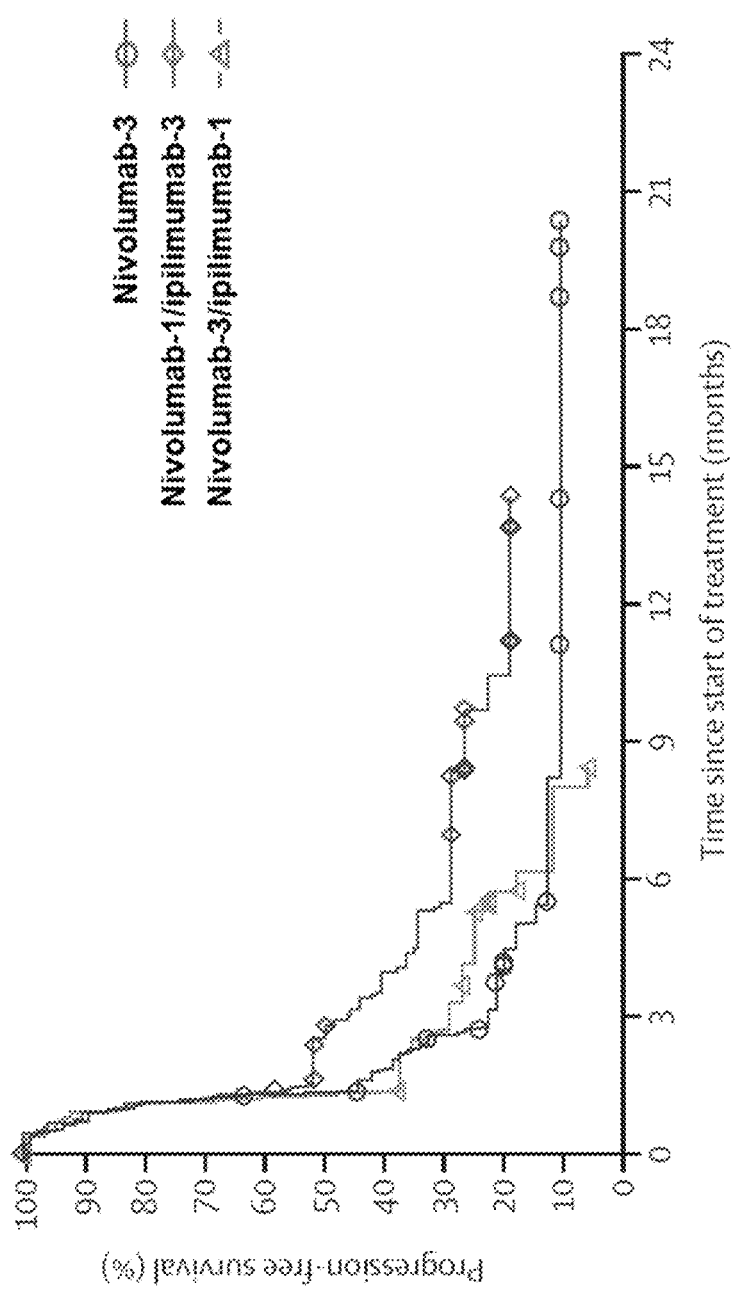

76 (78%) patients in the nivolumab 3 mg/kg cohort, 44 (72%) in the nivolumab 1 mg/kg plus ipilimumab 3 mg/kg cohort, and 42 (78%) in the nivolumab 3 mg/kg plus ipilimumab 1 mg/kg cohort had disease progression or died; median progression-free survival was 1.4 months (95% CI 1.4-1.9), 2•6 months (1.4-4.1), and 1.4 months (1.3-2.2), respectively. 1-year progression-free survival was 11% (95% CI 5-19) in the nivolumab 3 mg/kg cohort and 19% (9-32) for the nivolumab 1 mg/kg plus ipilimumab 3 mg/kg cohort (FIG. 4B). The nivolumab 3 mg/kg plus ipilimumab 1 mg/kg cohort had not met the 1-year milestone for progression-free survival at the time of database lock. Two (67%) of three patients in the nivolumab 1 mg/kg plus ipilimumab 1 mg/kg cohort had died and one (33%) had a progression event. Nine patients crossed over from the nivolumab 3 mg/kg cohort to the combination cohorts after progression (one to nivolumab 1 mg/kg plus ipilimumab 3 mg/kg and eight to nivolumab 3 mg/kg plus ipilimumab 1 mg/kg); eight of these patients had further disease progression and one patient in the nivolumab 3 mg/kg plus ipilimumab 1 mg/kg cohort withdrew consent and therefore response could not be determined.

Figures 5A, 5B:
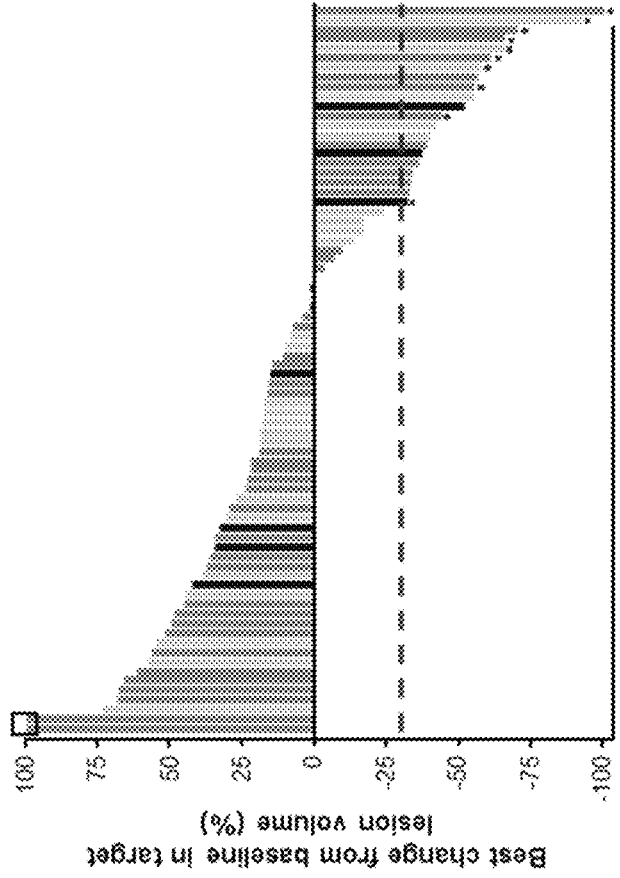
Figure 6A:
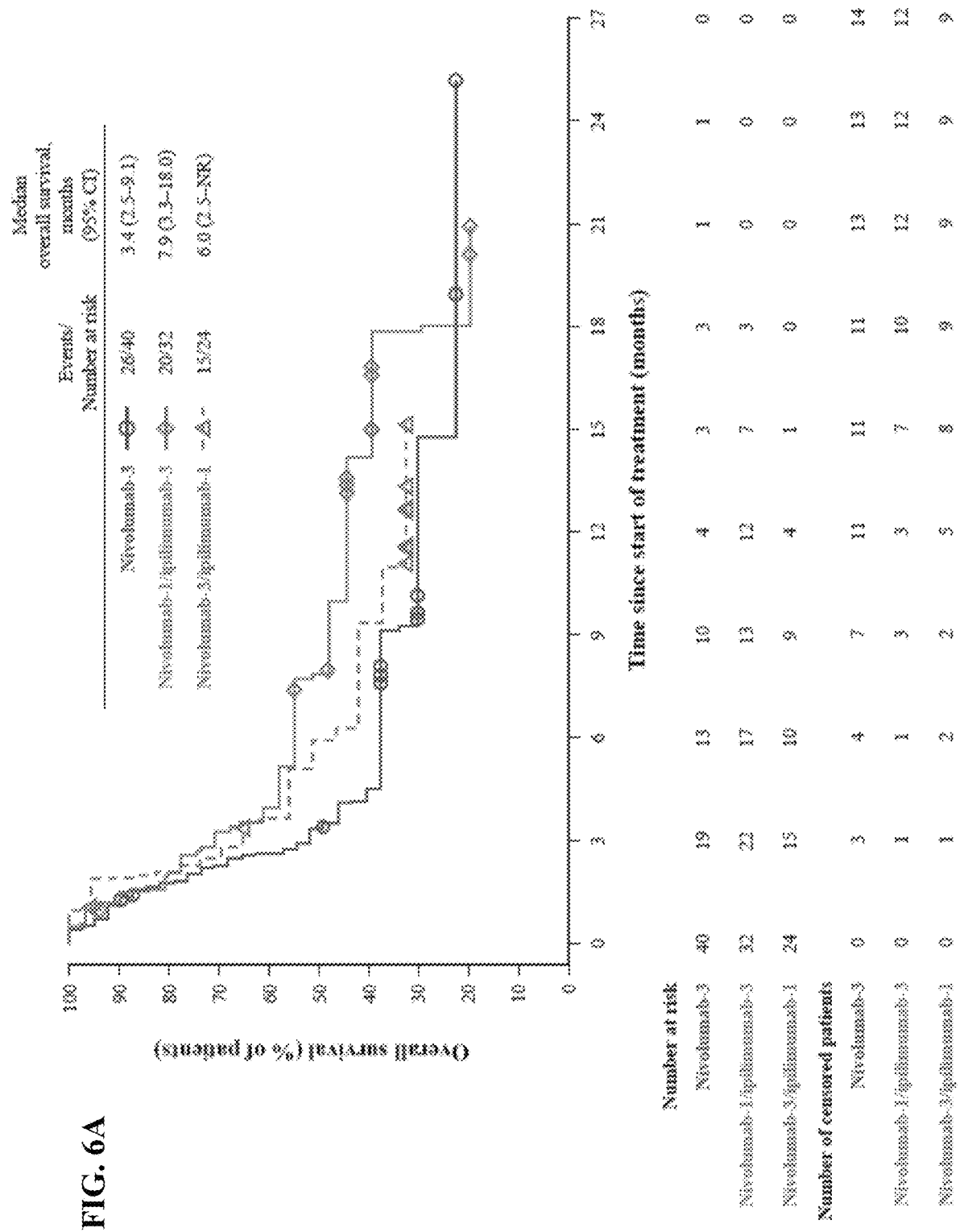
FIGS. 6A-6D provide Kaplan-Meier curves of overall survival (FIGS. 6A and 6B) and progression-free survival (FIGS. 6C and 6D) for subjects with one prior therapy (FIG. 6A and FIG. 6C) and two or more prior therapies (FIG. 6B and FIG. 6D). Subjects were treated with nivolumab 3 mg/kg (circles), nivolumab 1 mg/kg plus ipilimumab 3 mg/kg (diamonds), or nivolumab 3 mg/kg plus ipilimumab 1 mg/kg (triangles). The numbers of subjects at risk and the numbers of censored patients are shown for each treatment below the y-axes (FIGS. 6A-6D).
Figure 6B:
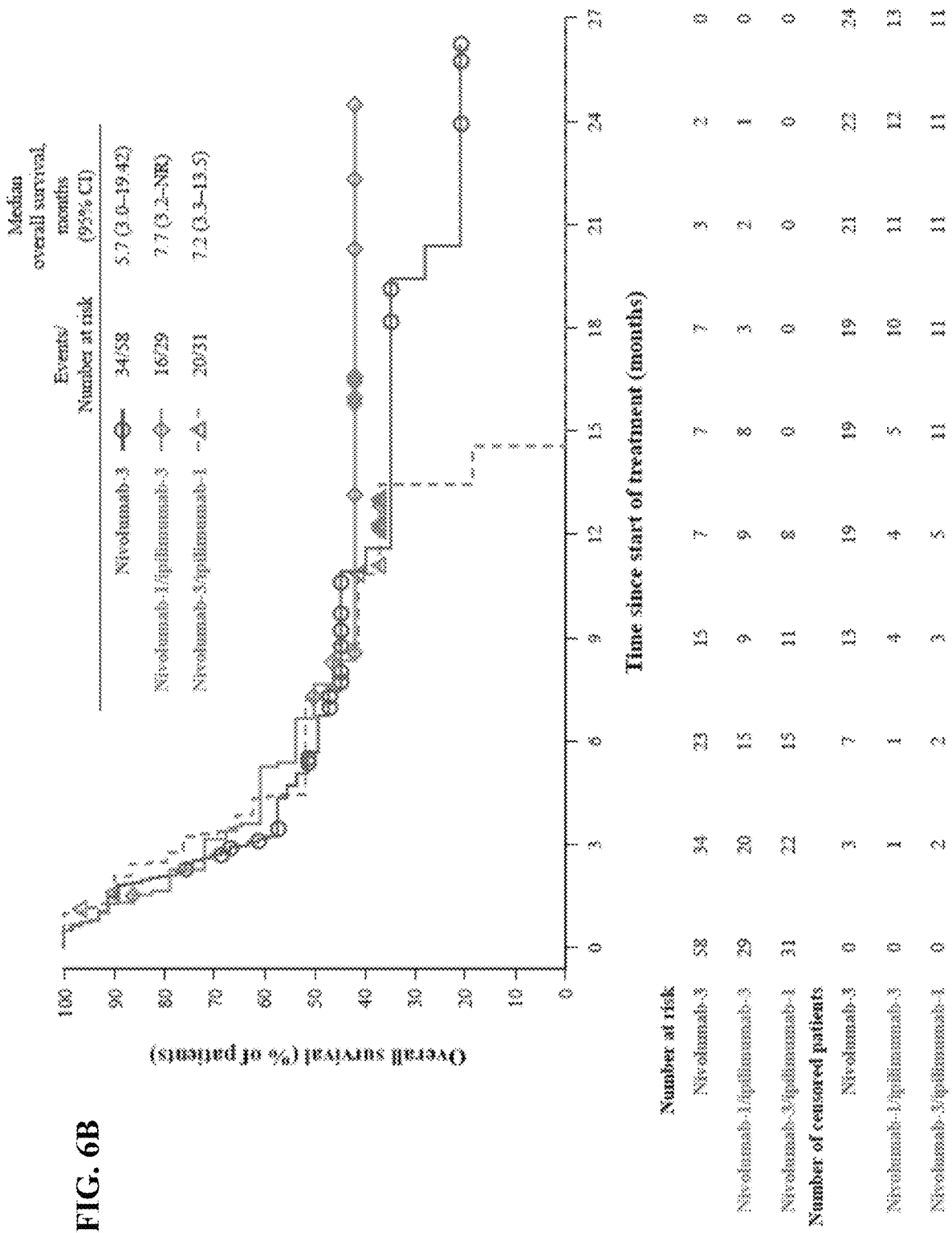
Figure 6C:
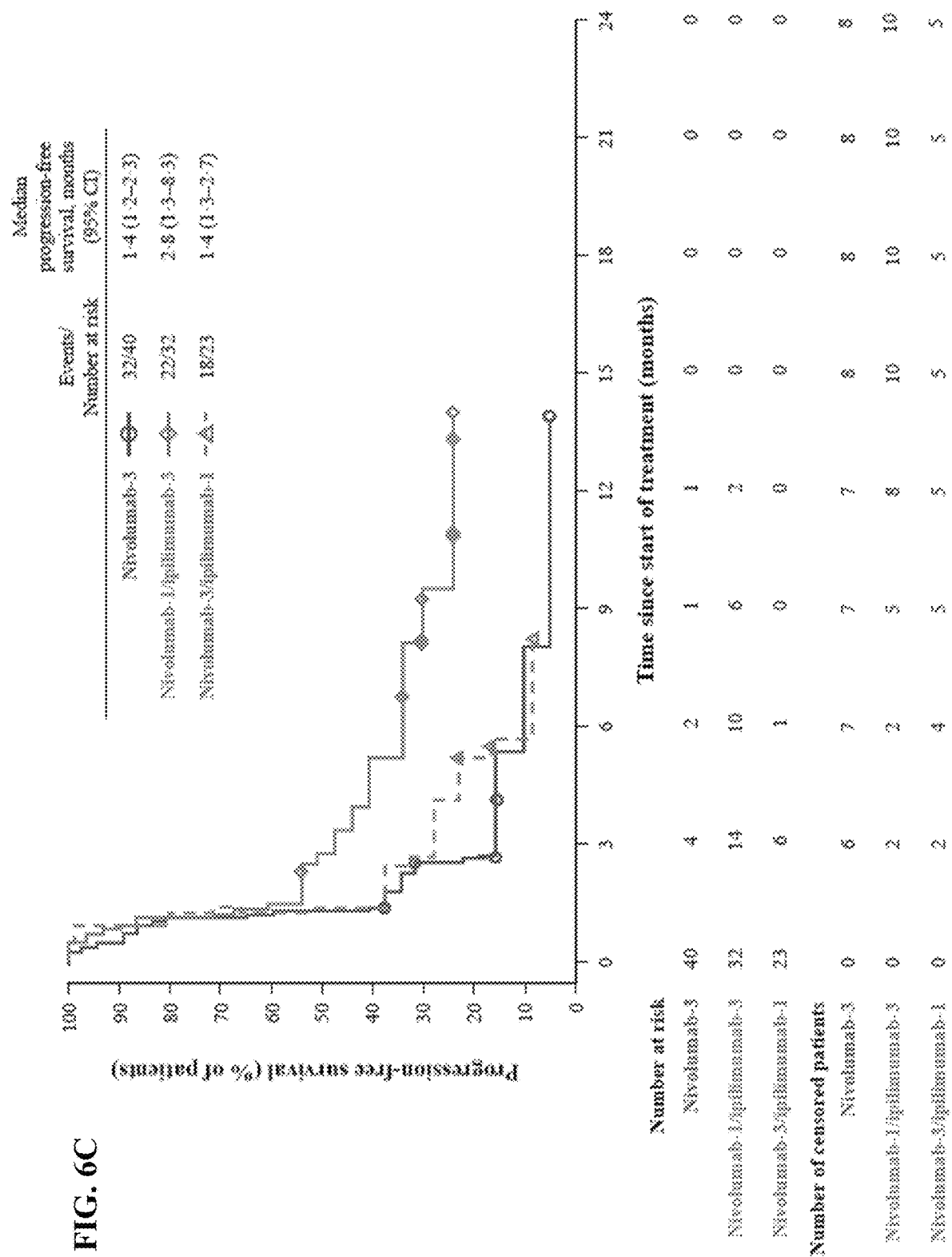
Figure 6D:
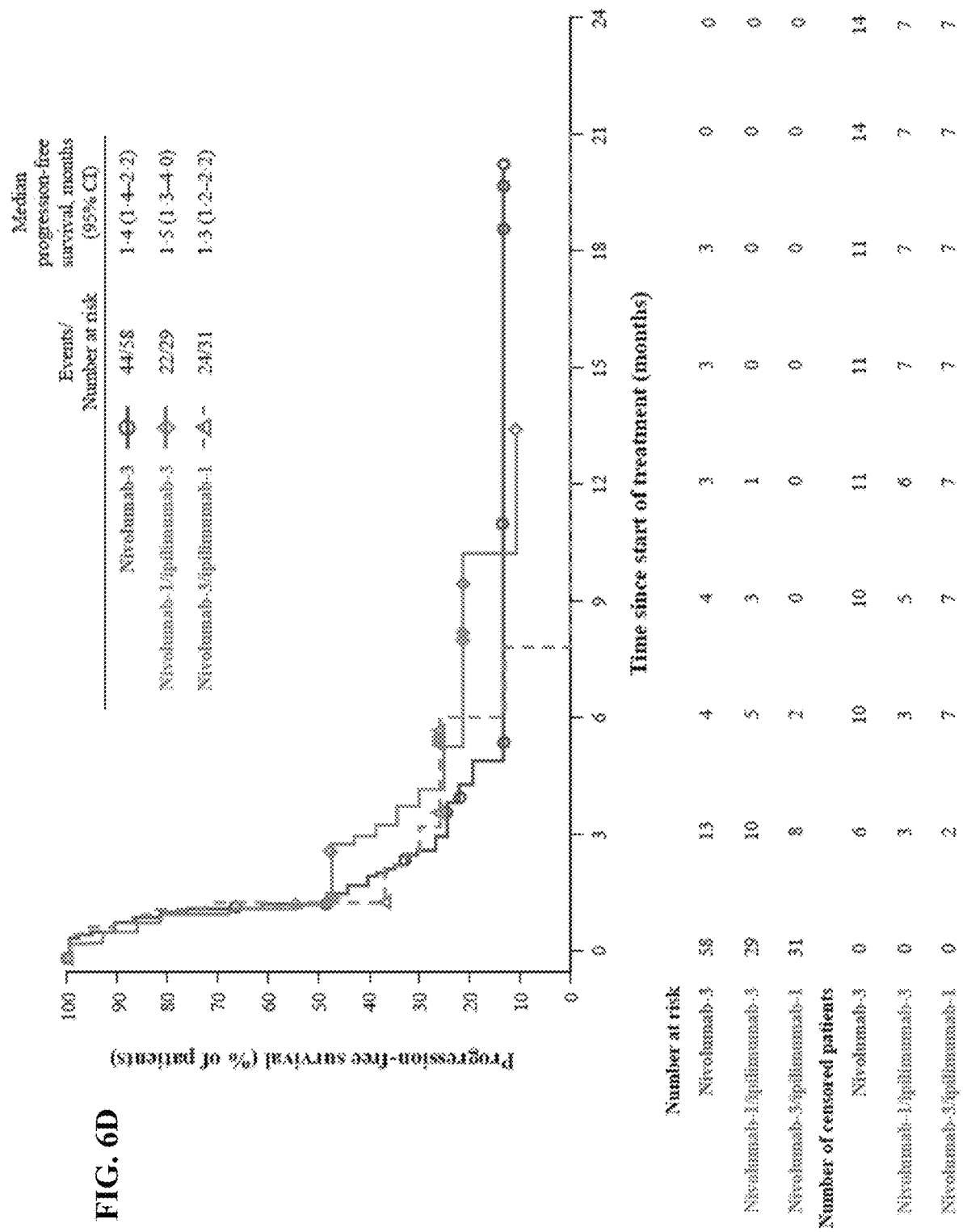

PD-L1 expression was assessable in 148 (69%) of 216 patient samples, of which 39 (27%) were provided as fresh biopsies and 109 (74%) were archived specimens. 25 (17%) had 1% or greater PD-L1 expression, and seven (5%) had 5% or greater PD-L1 expression (Table 3). In a pre-planned exploratory analysis of the nivolumab 3 mg/kg, nivolumab 1 mg/kg plus ipilimumab 3 mg/kg, and nivolumab 3 mg/kg plus ipilimumab 1 mg/kg cohorts, tumor responses occurred in patients irrespective of PD-L1 expression (FIGS. 5A-5C, respectively).

Grade 3 or 4 treatment-related adverse events occurred in 13 (13%) of 98 patients in the nivolumab 3 mg/kg cohort, 18 (30%) of 61 patients in the nivolumab 1 mg/kg plus ipilimumab 3 mg/kg cohort, and ten (19%) of 54 patients in the nivolumab 3 mg/kg plus ipilimumab 1 mg/kg cohort (Table 6); no patients in the nivolumab 1 mg/kg plus ipilimumab 1 mg/kg cohort had a grade 3 or 4 treatment-related adverse event (data not shown). The most commonly reported grade 3 or 4 treatment-related adverse events were increased lipase (none vs. 5 [8%] vs. none) and diarrhea (none vs. 3 [5%] vs. 1 [2%]). Four (4%) patients in the nivolumab 3 mg/kg cohort, two (67%) in the nivolumab 1 mg/kg plus ipilimumab 1 mg/kg cohort, 18 (30%) in the nivolumab 1 mg/kg plus ipilimumab 3 mg/kg cohort, and eight (15%) in the nivolumab 3 mg/kg plus ipilimumab 1 mg/kg cohort had dose delays due to treatment-related adverse events. Excluding malignant neoplasm, the most frequent serious adverse events were dyspnoea, experienced by five (5%) patients in the nivolumab 3 mg/kg cohort, two (3%) in the nivolumab 1 mg/kg plus ipilimumab 3 mg/kg cohort, and four (7%) in the nivolumab 3 mg/kg plus ipilimumab 1 mg/kg cohort, and diarrhea, experienced by two (2%) patients in the nivolumab 3 mg/kg cohort, four (7%) in the nivolumab 1 mg/kg plus ipilimumab 3 mg/kg cohort, and four (7%) patients in the nivolumab 3 mg/kg plus ipilimumab 1 mg/kg cohort. 17 patients discontinued treatment because of treatment-related adverse events: six (6%) patients in the nivolumab 3 mg/kg cohort (one patient each with limbic encephalitis, hyperglycaemia, stomatitis, increased alanine aninotransferase, increased gamma glutamyltransferase, and pneumonitis), seven (11%) in the nivolumab 1 mg/kg plus ipilimumab 3 mg/kg cohort (one patient each with colitis, myasthenia gravis, pneumonitis, and cardiomyopathy, and uveitis; one patient with hypothyroidism, hyperglycaemia and increased alanine aminotransferase; one patient with diarrhea and renal failure), and four (7%) in the nivolumab 3 mg/kg plus ipilimumab 1 mg/kg cohort (one patient each with colitis, pneumonitis, and peripheral neuropathy; one patient with dyspnoea and pneumonitis; Table 6). Two patients who received nivolumab 1 mg/kg plus ipilimumab 3 mg/kg died from treatment-related events of myasthenia gravis and worsening of renal failure, respectively, and one patient who received nivolumab 3 mg/kg plus ipilimumab 1 mg/kg died from treatment-related pneumonitis. Other than because of disease progression and study drug toxicity, the following deaths were reported: in the nivolumab 3 mg/kg group, three (3%) due to unknown causes, one (1%) due to sepsis and multi-organ failure, and one (1%) due to respiratory insufficiency not related to treatment; in the nivolumab 1 mg/kg plus ipilimumab 3 mg/kg group, three (5%) due to unknown causes, one (2%) due to subdural hematoma unrelated to study drug, one (2%) due to sedation, one (2%) due to hypovolemic septic shock and septic shock from candidaemia, and one (2%) due to abdominal sepsis and secondary intravascular disseminated coagulation; and in the nivolumab 3 mg/kg plus ipilimumab 1 mg/kg group, three (6%) due to unknown causes, and one (2%) due to adverse events not related to study drug.

TABLE 6

Treatment-related adverse events

| | Nivolumab-3 (n = 98) | | | Nivolumab-1/ Ipilimumab-3 (n = 61) | | | Nivolumab-3/ Ipilimumab-1 (n = 54) | | |
|---|---|---|---|---|---|---|---|---|---|
| | Grade 1-2 | Grade 3 | Grade 4 | Grade 1-2 | Grade 3 | Grade 4 | Grade 1-2 | Grade 3 | Grade 4 |
| Any event | 39 (40%) | 9 (9%) | 4 (4%) | 30 (49%) | 14 (23%) | 4 (7%) | 30 (56%) | 8 (15%) | 2 (4%) |
| Fatigue | 10 (10%) | 1 (1%) | 0 | 16 (26%) | 0 | 0 | 12 (22%) | 0 | 0 |
| Pruritus | 11 (11%) | 0 | 0 | 11 (18%) | 1 (2%) | 0 | 5 (9%) | 0 | 0 |
| Diarrhea | 7 (7%) | 0 | 0 | 10 (16%) | 3 (5%) | 0 | 8 (15%) | 1 (2%) | 0 |
| Nausea | 7 (7%) | 0 | 0 | 6 (10%) | 1 (2%) | 0 | 4 (7%) | 0 | 0 |
| Decreased appetite | 6 (6%) | 0 | 0 | 4 (7%) | 0 | 0 | 6 (11%) | 0 | 0 |
| Pneumonitis | 2 (2%) | 1 (1%) | 0 | 1 (2%) | 1 (2%) | 0 | 2 (4%) | 0 | 1 (2%) |
| Vomiting | 2 (2%) | 1 (1%) | 0 | 2 (3%) | 1 (2%) | 0 | 5 (9%) | 0 | 0 |
| Hypo-thyroidism | 3 (3%) | 0 | 0 | 9 (15%) | 1 (2%) | 0 | 4 (7%) | 0 | 0 |
| Increased aspartate aminotransferase | 3 (3%) | 0 | 0 | 3 (5%) | 0 | 0 | 0 | 1 (2%) | 0 |
| Hyper-thyroidism | 2 (2%) | 0 | 0 | 7 (11%) | 0 | 0 | 3 (6%) | 0 | 0 |
| Hyponatraemia | 2 (2%) | 0 | 0 | 0 | 1 (2%) | 0 | 0 | 0 | 0 |
| Increased alanine aminotransferase | 2 (2%) | 1 (1%) | 0 | 2 (3%) | 0 | 0 | 0 | 1 (2%) | 0 |
| Increased transaminases | 2 (2%) | 0 | 0 | 0 | 0 | 0 | 1 (2%) | 1 (2%) | 0 |
| Rash | 2 (2%) | 0 | 0 | 10 (16%) | 2 (3%) | 0 | 4 (7%) | 0 | 0 |
| Anaemia | 1 (1%) | 0 | 0 | 4 (7%) | 0 | 0 | 3 (6%) | 1 (2%) | 0 |
| Dyspnoea | 1 (1%) | 0 | 0 | 0 | 1 (2%) | 0 | 1 (2%) | 2 (4%) | 0 |
| Rash, maculopapular | 1 (1%) | 0 | 0 | 6 (10%) | 2 (3%) | 0 | 2 (4%) | 0 | 0 |
| Adrenal insufficiency | 0 | 0 | 0 | 1 (2%) | 0 | 0 | 1 (2%) | 1 (2%) | 0 |
| Aseptic meningitis | 0 | 0 | 0 | 0 | 0 | 0 | 0 | 0 | 1 (2%) |
| Cardio-myopathy | 0 | 0 | 0 | 0 | 0 | 1 (2%) | 0 | 0 | 0 |
| Colitis | 0 | 0 | 0 | 1 (2%) | 1 (2%) | 0 | 0 | 1 (2%) | 0 |
| Decreased neutrophil count | 0 | 0 | 0 | 0 | 1 (2%) | 0 | 0 | 0 | 0 |
| Drug-induced liver injury | 0 | 1 (1%) | 0 | 0 | 0 | 0 | 0 | 0 | 0 |
| Encephalitis | 0 | 0 | 1 (1%) | 1 (2%) | 0 | 0 | 0 | 0 | 0 |
| Eyelid ptosis | 0 | 0 | 0 | 0 | 1 (2%) | 0 | 0 | 0 | 0 |
| Haemonhagic-gastritis | 0 | 0 | 0 | 0 | 1 (2%) | 0 | 0 | 0 | 0 |
| Hyper-glycaemia | 0 | 0 | 1 (1%) | 2 (3%) | 0 | 1 (2%) | 0 | 0 | 0 |
| Hypertrans-aminasaemia | 0 | 0 | 0 | 0 | 1 (2%) | 0 | 0 | 0 | 0 |
| Hypoxia | 0 | 1 (1%) | 0 | 0 | 0 | 0 | 0 | 0 | 0 |
| Ileus | 0 | 0 | 0 | 0 | 0 | 0 | 0 | 1 (2%) | 0 |
| Increased amylase | 0 | 0 | 1 (1%) | 3 (5%) | 1 (2%) | 0 | 2 (4%) | 0 | 0 |
| Increased gamma glutamyltransferase | 0 | 0 | 1 (1%) | 0 | 0 | 0 | 0 | 1 (2%) | 0 |
| Increased lipase | 0 | 0 | 0 | 2 (3%) | 4 (7%) | 1 (2%) | 0 | 0 | 0 |
| Large intestine perforation | 0 | 0 | 0 | 0 | 0 | 0 | 0 | 1 (2%) | 0 |
| Myasthenia gravis | 0 | 0 | 0 | 0 | 1 (2%) | 0 | 0 | 0 | 0 |
| Non-cardiac chest pain | 0 | 1 (1%) | 0 | 0 | 0 | 0 | 0 | 0 | 0 |
| Pericardial effusion | 0 | 1 (1%) | 0 | 0 | 0 | 0 | 0 | 0 | 0 |
| Peripheral neuropathy | 0 | 0 | 0 | 0 | 0 | 0 | 0 | 1 (2%) | 0 |

TABLE 6-continued

Treatment-related adverse events

|  | Nivolumab-3 (n = 98) | | | Nivolumab-1/ Ipilimumab-3 (n = 61) | | | Nivolumab-3/ Ipilimumab-1 (n = 54) | | |
| --- | --- | --- | --- | --- | --- | --- | --- | --- | --- |
|  | Grade 1-2 | Grade 3 | Grade 4 | Grade 1-2 | Grade 3 | Grade 4 | Grade 1-2 | Grade 3 | Grade 4 |
| Renal failure | 0 | 0 | 0 | 0 | 0 | 1 (2%) | 0 | 0 | 0 |
| Stomatitis | 0 | 1 (1%) | 0 | 1 (2%) | 0 | 0 | 0 | 0 | 0 |
| Thrombocytopenia | 0 | 0 | 0 | 0 | 0 | 0 | 3 (6%) | 1 (2%) | 0 |
| Tumor lysis syndrome | 0 | 0 | 0 | 0 | 0 | 0 | 0 | 1 (2%) | 0 |

Data presented as n (%). This table reports grade 1-2 treatment-related events in ≥10% of patients in any treatment cohort and all grade 3-4 events. Safety analyses included all patients who were enrolled at least 90 days prior to database lock; patients with adverse events after crossover from nivolumab 3 mg/kg to combination treatment are excluded. Some patients had more than one adverse event. Two patients in the nivolumab 1 mg/kg plus ipilimumab 3 mg/kg group died from myasthenia gravis and worsening of renal failure, respectively; both events were regarded to be treatment related. One patient in the nivolumab 3 mg/kg plus ipilimumab 1 mg/kg cohort died from pneumonitis, regarded as treatment related.

Two patients had grade 2 limbic encephalitis: one in the nivolumab 3 mg/kg cohort (reported as not treatment-related by investigator) and one in the nivolumab 1 mg/kg plus ipilimumab 3 mg/kg cohort (reported as treatment-related by investigator); both events resolved with immunosuppressive treatment. One patient in the nivolumab 3 mg/kg cohort had grade 4 limbic encephalitis (reported as treatment-related by investigator) that did not resolve with intravenous immunoglobulin and corticosteroid treatment. Treatment-related pneumonitis occurred in eight patients and resolved in six of eight patients with treatment. The outcome was unknown for one patient, and one patient died.

One patient who crossed over from nivolumab 3 mg/kg to nivolumab 1 mg/kg plus ipilimumab 3 mg/kg had treatment-related grade 3 elevations in alanine aminotransferase levels. Five (8%) patients in the nivolumab 1 mg/kg plus ipilimumab 3 mg/kg cohort had grade 3 or 4 asymptomatic lipase elevations without clinical signs of pancreatitis (Table 6).

Objective responses were observed in patients with one previous line of therapy, and in patients with two or more previous therapies (Table 7). Median overall survival and progression-free survival were not substantially different for patients with one versus two or more previous treatments, with the possible exception of longer progression-free survival in patients with one previous therapy receiving nivolumab 1 mg/kg plus ipilimumab 3 mg/kg (FIGS. 6A-6D).

TABLE 7

Best overall tumor response by lines of therapy.
One Prior Therapy

|  | Nivolumab-3 (n = 40) | Nivolumab-1/ Ipilimumab-3 (n = 32) | Nivolumab-3/ Ipilimumab-1 (n = 23) |
| --- | --- | --- | --- |
| Objective Response Rate (95% CI) | 4 (10%) (3-24) | 9 (28%) (14-47) | 5 (22%) (8-44) |
| Best overall response |  |  |  |
| Complete response | 0 | 1 (3%) | 0 |
| Partial response | 4 (10%) | 8 (25%) | 5 (22%) |
| Stable disease | 8 (20%) | 6 (19%) | 3 (13%) |
| Progressive disease | 22 (55%) | 10 (31%) | 12 (52%) |
| Unable to determine | 5 (13%) | 6 (19%) | 3 (13%) |
| Not reported | 1 (3%) | 1 (3%) | 0 |

TABLE 7-continued

Two or More Prior Therapies

|  | Nivolumab-3 (n = 58) | Nivolumab-1/ Ipilimumab-3 (n = 29) | Nivolumab-3/ Ipilimumab-1 (n = 31) |
| --- | --- | --- | --- |
| Objective Response Rate (95% CI) | 6 (10%) (4-21) | 5 (17%) (6-36) | 5 (16%) (6-34) |
| Best overall response |  |  |  |
| Complete response | 0 | 0 | 0 |
| Partial response | 6 (10%) | 5 (17%) | 5 (16%) |
| Stable disease | 14 (24%) | 7 (24%) | 6 (19%) |
| Progressive disease | 30 (52%) | 13 (45%) | 17 (55%) |
| Unable to determine | 7 (12%) | 2 (7%) | 3 (10%) |
| Not reported | 1 (2%) | 2 (7%) | 0 |

Data presented as n or n (%) unless otherwise stated. All patients were enrolled at least 90 days prior to database lock.

Figure 7A:
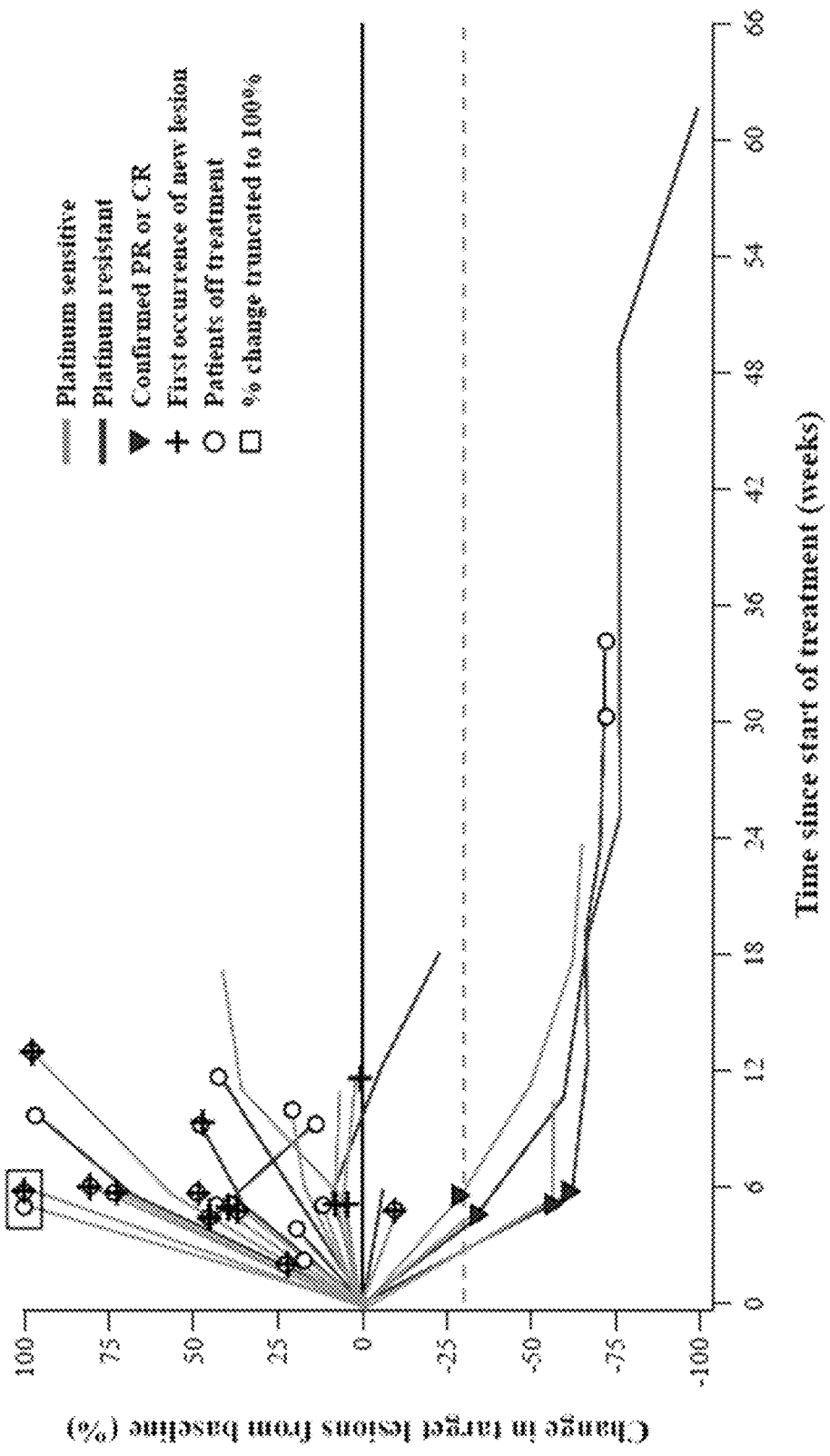
FIGS. 7A-7C provide graphical representations of the changes in tumor burden according to platinum sensitivity in individual patients receiving nivolumab 3 mg/kg (FIG. 7A), nivolumab 1 mg/kg plus ipilimumab 3 mg/kg (FIG. 7B), and nivolumab 3 mg/kg plus ipilimumab 1 mg/kg (FIG. 7C) (platinum sensitive tumors are indicated by grey lines and platinum resistant tumors are indicated by black lines). Only patients with target lesions at baseline and with ≥1 on-treatment tumor assessment were included (nivolumab-3, n=31; nivolumab-1/ipilimumab-3, n=21; nivolumab-3/ipilimumab-1, n=17). Panels show the tumor burden (assessed as the longest linear dimension) over time in patients receiving second-line nivolumab-3 (FIG. 7A), nivolumab-1/ipilimumab-3 (FIG. 7B), and nivolumab-3/ipilimumab-1 (FIG. 7C). Horizontal reference line indicates the 30% reduction consistent with a RECIST (version 1.1) objective response. Subjects displaying a complete response (CR) or a partial response (PR) are marked by an inverted triangle at the point of PR or CR. A plus sign indicates the first occurrence of a new lesion, and an open circle indicates the point at which the subject went off treatment. Measurements in excess of 100% were truncated to 100%, and the data point is marked by an open square.
Figure 7B:
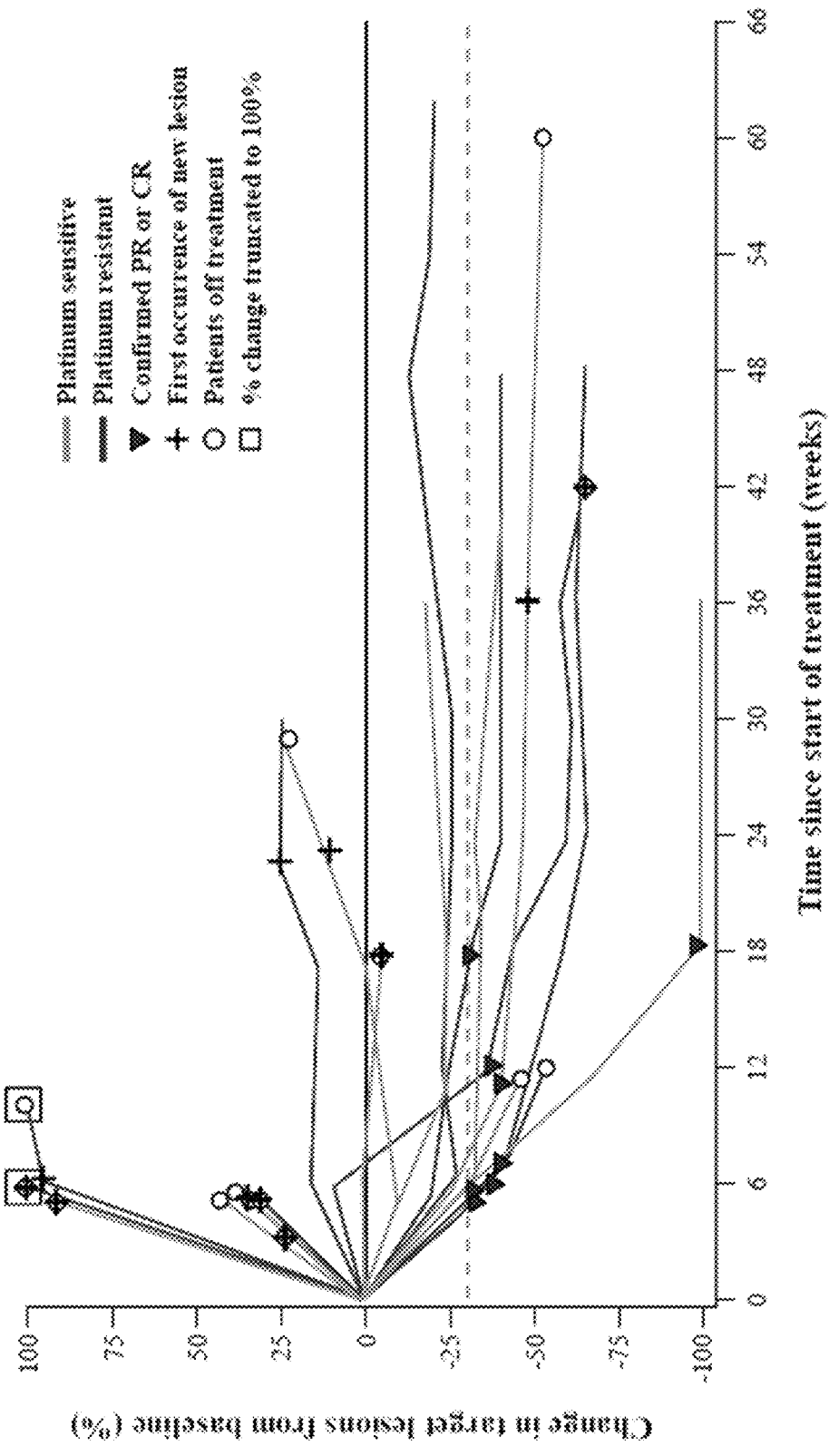
Figure 7C:
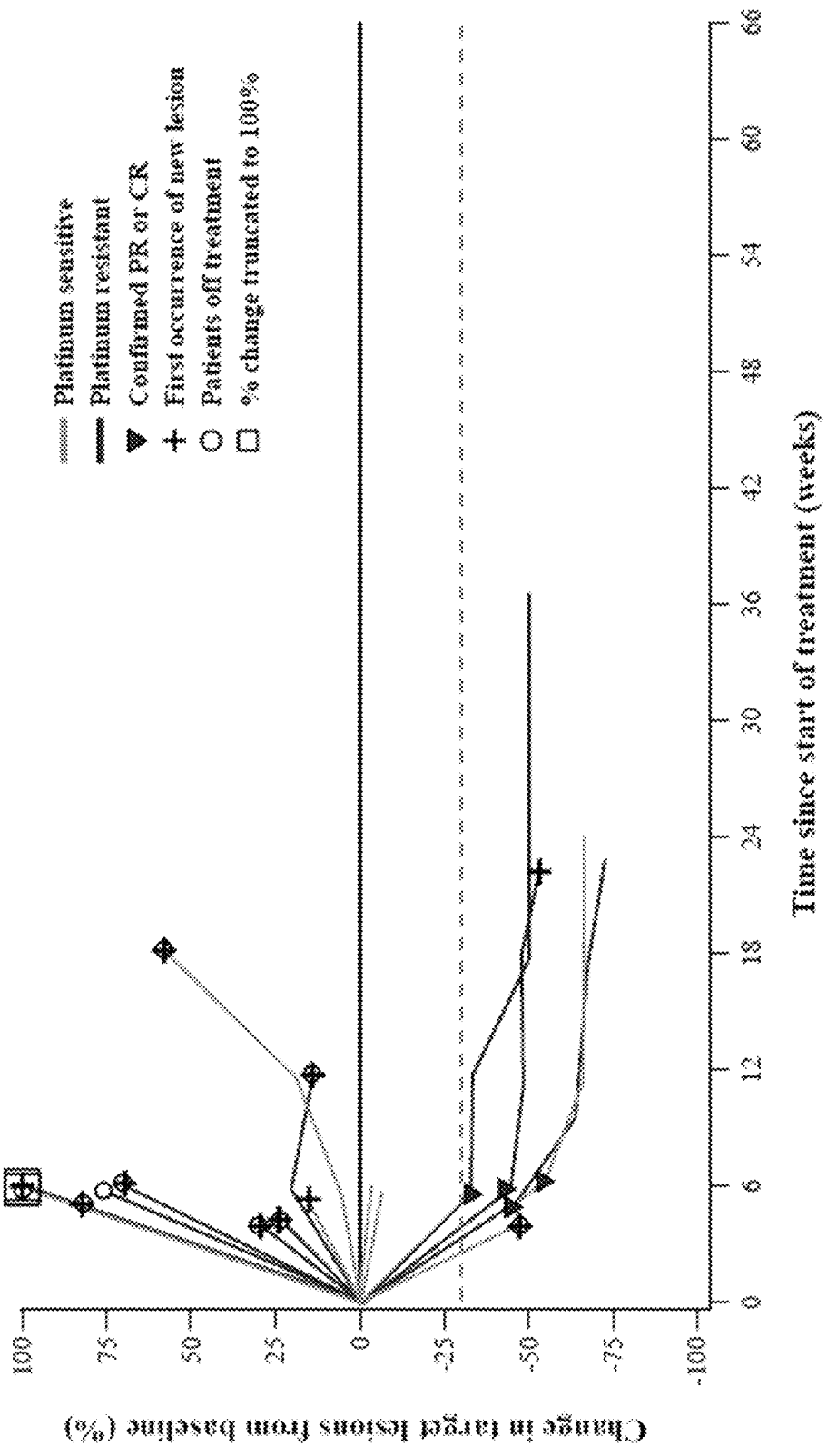

In a post-hoc analysis in patients treated with a platinum agent as a first-line treatment, objective responses were achieved in patients with both platinum-sensitive and platinum-resistant disease (FIGS. 7A-7C; Table 8). Among patients with platinum-sensitive disease, two (4%) of 55 in the nivolumab 3 mg/kg cohort and two (8%) of 25 in the nivolumab 1 mg/kg plus ipilimumab 3 mg/kg cohort received subsequent platinum-based cancer therapy. No patients with platinum-sensitive disease in the nivolumab 3 mg/kg plus ipilimumab 1 mg/kg arm received subsequent platinum-based cancer therapy.

TABLE 8

Best overall tumor response by sensitivity
to first-line platinum-based treatment.
Platinum Sensitive*

|  | Nivolumab-3 (n = 55) | Nivolumab-1/ Ipilimumab-3 (n = 25) | Nivolumab-3/ Ipilimumab-1 (n = 21) |
| --- | --- | --- | --- |
| Objective Response Rate (95% CI) | 6 (11%) (4-22) | 7 (28%) (12-49) | 4 (19%) (5-42) |
| Best overall response |  |  |  |
| Complete response | 0 | 0 | 0 |
| Partial response | 6 (11%) | 7 (28%) | 4 (19%) |
| Stable disease | 14 (25%) | 7 (28%) | 5 (24%) |
| Progressive disease | 29 (53%) | 8 (32%) | 11 (52%) |
| Unable to determine | 5 (9%) | 3 (12%) | 1 (5%) |
| Not reported | 1 (2%) | 0 | 0 |

TABLE 8-continued

Platinum Resistant†

|  | Nivolumab-3 (n = 30) | Nivolumab-1/ Ipilimumab-3 (n = 23) | Nivolumab-3/ Ipilimumab-1 (n = 21) |
|---|---|---|---|
| Objective response rate | 3 (10%) | 4 (17%) | 2 (10%) |
| (95% CI) | (2-27) | (5-39) | (1-30) |
| Best overall response |  |  |  |
| Complete response | 0 | 1 (4%) | 0 |
| Partial response | 3 (10%) | 3 (13%) | 2 (10%) |
| Stable disease | 5 (17%) | 2 (9%) | 1 (5%) |
| Progressive disease | 16 (53%) | 10 (44%) | 13 (62%) |
| Unable to determine | 5 (17%) | 5 (22%) | 5 (24%) |
| Not reported | 1 (3%) | 2 (9%) | 0 |

Data presented as n (%) unless otherwise stated. All patients were enrolled at least 90 days prior to database lock. For patients with known response to platinum-based therapy, platinum sensitivity was unknown for 29 patients as follows: nivolumab-3, n = 10; nivolumab-1/ipilimumab-3, n = 11; nivolumab-3/ipilimumab-1, n = 8.
*Patient relapsed ≥90 days after platinum-based chemotherapy.
†Patient failed to respond to, or relapsed <90 days after, platinum-based chemotherapy.

As of the database lock on Mar. 30, 2017, by blinded independent central review, 11% of patients in the nivolumab 3 mg/kg group and 23% of patients in the nivolumab 1 mg/kg plus ipilimumab 3 mg/kg group had an objective response to treatment. See Table 9. Median time to response was 1.4 months (1.1-4.1 months, range) in the nivolumab 3 mg/kg group and 2 months (1-4.1 months, range) in the nivolumab 3 mg/kg plus ipilimumab 1 mg/kg group. Median duration of response was 17.9 months (2.8-34.6, range) in the nivolumab 3 mg/kg group and 14.2 months (1.5-26.5, range) in the nivolumab 3 mg/kg plus ipilimumab 1 mg/kg group. 45% of responders in the nivolumab 3 mg/kg group and 36% of responders in the nivolumab 3 mg/kg plus ipilimumab 1 mg/kg group had an ongoing response after 2 years.

TABLE 9

Summary of response.

|  | Nivolumab (n = 98) | Nivolumab + Ipilimumab (n = 61) |
|---|---|---|
| ORR, % (95% CI) | 11 (6, 19) | 23 (13, 36) |
| Median time to response, mo (range) | 1.4 (1.1-4.1) | 2.0 (1.0-4.1) |
| Median DOR, mo (range) | 17.9 (2.8-34.6+) | 14.2 (1.5-26.5+) |
| Patients with ongoing responses at 2 yr,$^a$ % | 45 | 36 |

$^a$Percentage of responders (nivolumab, n = 11; nivolumab + ipilimumab, n = 14)

Figure 9:
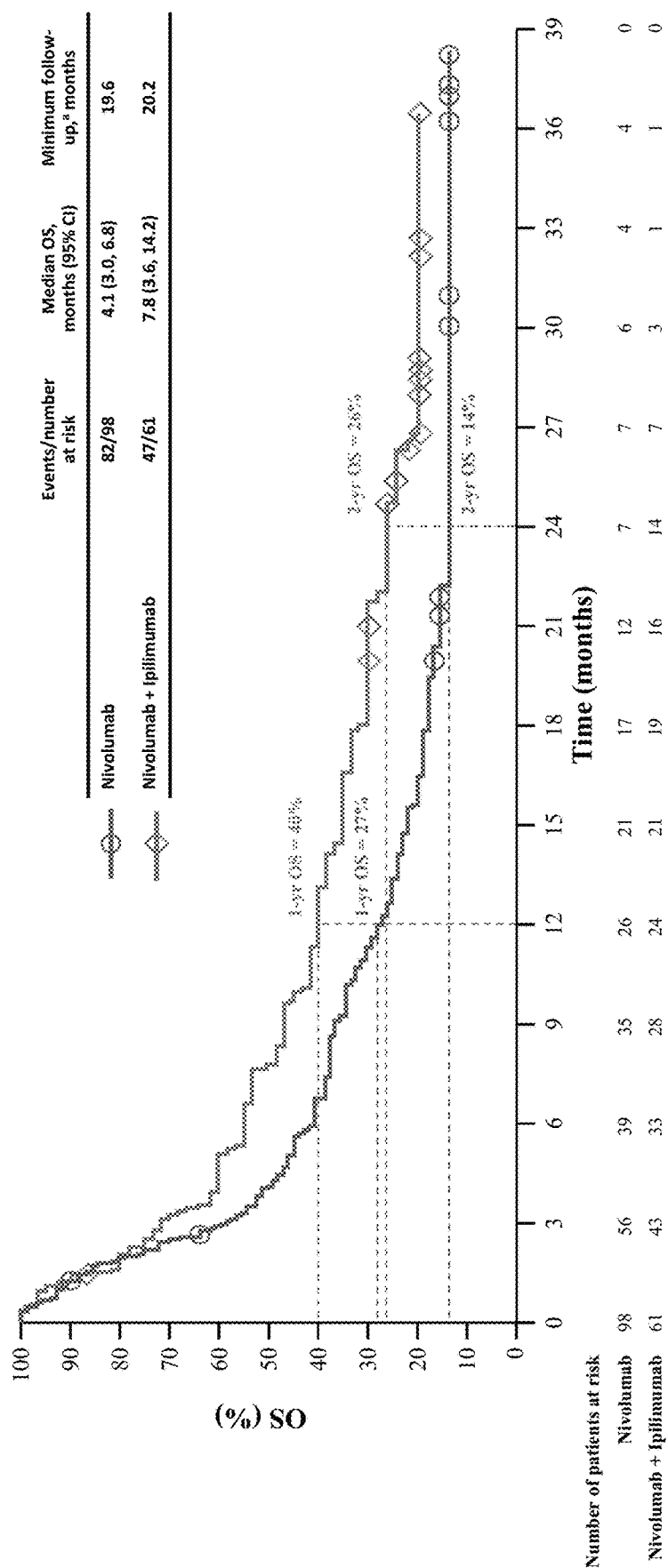
FIG. 9 provides a Kaplan-Meier cufrve of overall survival for subjects treated with nivolumab 3 mg/kg (circles) or nivolumab 1 mg/kg plus ipilimumab 3 mg/kg (diamonds). The numbers of subjects at risk are shown for each treatment below the y-axis.

Tumor PD-L1 expression was examined in patients who had an objective response to treatment. See Table 10. Within the non-randomized cohort, PD-L1 expression was not evaluable in 43 patients (27%). Of those patients with quantifiable PD-L1 expression (159 patients), 82% had a tumor expressing less than 1% PD-L1 and 18% had a tumor expressing at least 1% PD-L1. See FIG. 9. For those patients a tumor expressing at least 1% PD-L1, there was a 9% ORR in the nivolumab 3 mg/kg group and a 10% ORR in the nivolumab 1 mg/kg plus ipilimumab group 3 mg/kg. For patients with a tumor expressing less than 1% PD—L1, there was a 14% ORR in the nivolumab 3 mg/kg group and a 32% ORR in the nivolumab 1 mg/kg plus ipilimumab 3 mg/kg group.

TABLE 10

Objective response rate (ORR) by tumor PD-L1 expression

| | ORR, % (n/N) | |
|---|---|---|
| PD-L1 expression | Nivolumab (n = 98) | Nivolumab + Ipilimumab (n = 61) |
| ≥1% | 9 (1/11) | 10 (1/10) |
| <1% | 14 (9/64) | 32 (10/31) |

Overall survival (OS) was improved by treatment with nivolumab in combination with ipilimumab. See FIG. 9. Median overall survival was 4.1 months (95% CI 3.0-6.8) in the nivolumab 3 mg/kg group, and 7.8 months (3.6-14.2) in the nivolumab 3 mg/kg plus ipilimumab 1 mg/kg group. 1-year overall survival was 27% for the nivolumab 3 mg/kg group, and 40% for the nivolumab 1 mg/kg plus ipilimumab 3 mg/kg group. 2-year overall survival was 14% for the nivolumab 3 mg/kg group, and 26% for the nivolumab 1 mg/kg plus ipilimumab 3 mg/kg group. Minimum follow-ups occurred at 19.6 months (median=23.3 months) for patients in the nivolumab 3 mg/kg group, and at 20.2 months (median=28.6 months) for patients in the nivolumab 3 mg/kg plus ipilimumab 1 mg/kg group. Follow-up was calculated as time from first dose to database lock. In some instances, follow-ups were more frequent, e.g., for patients who died prior to the Mar. 30, 2017 database lock.

Discussion

Our findings show that nivolumab monotherapy and nivolumab plus ipilimumab provide clinically meaningful activity and an acceptable safety profile for patients with limited or extensive-stage SCLC and disease progression after at least one prior regimen. The prognosis for patients with progression after prior treatment with platinum-based chemotherapy is poor. Patients with advanced SCLC frequently respond to first-line therapy; however, recurrence is inevitable, and effective options at the time of progression and in patients with platinum-resistant disease are limited. Patients with extensive-stage SCLC have a 2-year survival rate of less than 5%.

Our trial enrolled a heterogeneous patient population with platinum-sensitive or platinum-resistant disease and a range of previous lines of therapy, making comparisons with other second-line trials difficult. Responses and stable disease were seen in all treatment cohorts. Tumor regression followed both conventional and immune-related patterns of response (prolonged reduction in tumor burden in the presence of new lesions). Although the numbers of patients in subgroups were small, preliminary analysis showed similar responses between platinum-sensitive and platinum-resistant subgroups, and similar activity in patients with one previous regimen and those with two or more previous regimens. Across treatment groups, responses were durable.

One phase 2 study evaluated temozolomide in a similar population of patients with disease progression after one or two previous chemotherapy regimens. Although the proportions of patients achieving an objective response were similar to those shown in our study—11 (23%) of 48 patients with platinum-sensitive disease and two (13%) of 16 patients with platinum-refractory disease—the median duration of response to temozolomide was lower: 3•5 months (range 1•4-14•7) for all treated patients. Rova-T, a DLL3-targeted antibody-drug conjugate, showed antitumor activity and manageable toxicity in a phase 1 study of patients with SCLC and progression after one or two previous lines of therapy. An objective response was achieved in seven (44%) of 16 patients positive for the DLL3 biomarker treated at the maximum tolerated doses.

Limitations of our study include that the study cohorts were not randomized, and the study was not powered for formal comparisons across cohorts. Baseline characteristics were generally similar across the cohorts, and although the combination treatment cohorts showed similar responses, responses seemed to be deeper with the nivolumab 1 mg/kg plus ipilimumab 3 mg/kg regimen. This dosing regimen has also been shown to be efficacious in previously untreated melanoma.

The activity of nivolumab as monotherapy or combined with ipilimumab in patients irrespective of platinum sensitivity or line of therapy is an important aspect differentiating immune-checkpoint inhibitors from topotecan or amrubicin in SCLC. Response to topotecan depends on chemosensitivity, driven by tumor resistance mutations. By contrast, the genomically unstable nature of SCLC2 might make it sensitive to immune-checkpoint blockade via induction or restoration of a tumor antigen-driven immune response. Because few lymphocytes are observed in SCLC tumors, one hypothesis is that there is a greater need to target the lymphoid compartment with CTLA-4 inhibition in addition to PD-1 inhibition to maximize the treatment effect.

Some studies have shown increased activity of PD-1 blockade in patients with PD-L1-expressing NSCLC. However, data, including from this study, suggest that there is a lower prevalence of PD-L1 expression in SCLC versus NSCLC. A trial of pembrolizumab, a PD-1 immune-checkpoint inhibitor, reported an initial response in four (25%) of 16 patients and durable responses in patients with PD-L1-positive extensive-stage SCLC. In our study, objective responses were observed in patients irrespective of PD-L1 expression, including deep tumor responses in patients with PD-L1 tumor expression less than 1%. Whether PD-L1 expression is predictive of benefit in SCLC must await analysis in a larger population.

Although more than half of patients in this trial had received two or more chemotherapy regimens, 1-year overall survival (33% for nivolumab 3 mg/kg and 43% for nivolumab 1 mg/kg plus ipilimumab 3 mg/kg) was comparable with or better than that reported in historical trials of second-line topotecan or amrubicin. Consistent with other trials with immune-checkpoint inhibitors across multiple solid tumors, and unlike trials of topotecan, findings from our study showed a flattening of the overall survival curves for the nivolumab 3 mg/kg and nivolumab 1 mg/kg plus ipilimumab 3 mg/kg cohorts, suggesting a survival benefit in a subset of patients. However, because of the small numbers in this trial, it is difficult to determine when this occurs. Also consistent with findings from previous randomized trials of immuno-oncology agents, there seems to be a greater effect of nivolumab or ipilimumab treatment on overall survival than progression-free survival.

Adverse events were managed using established safety guidelines. Most toxic effects in the nivolumab 3 mg/kg and nivolumab 3 mg/kg plus ipilimumab 1 mg/kg cohorts were mild to moderate, with only six (6%) patients in the nivolumab 3 mg/kg group and four (7%) in the nivolumab 3 mg/kg plus ipilimumab 1 mg/kg group discontinuing because of toxicity. More treatment-related grade 3 or 4 adverse events occurred in the nivolumab 1 mg/kg plus ipilimumab 3 mg/kg cohort, with seven (11%) patients discontinuing because of toxicity. This regimen was used effectively and safely in a phase 3 trial in patients with melanoma, suggesting that this schedule is feasible in patients with SCLC. In all cohorts, fewer treatment-related toxic effects were reported when compared with trials of topotecan or amrubicin.

Three patients had limbic encephalitis, and one patient receiving nivolumab 1 mg/kg plus ipilimumab 3 mg/kg died of treatment-related myasthenia gravis. Autoimmune encephalitis and myasthenia gravis have been reported, albeit rarely, with both nivolumab and ipilimumab. The frequency of these events seems to be higher in patients with SCLC compared with other malignant diseases, perhaps due to the tendency for paraneoplastic neurological syndromes associated with this disease. Treatment-related pneumonitis was reported in eight patients across all the treatment cohorts and resulted in death in one patient receiving nivolumab 3 mg/kg plus ipilimumab 1 mg/kg. It is crucial to closely monitor for immune-related adverse events or unmasking of previously subclinical autoimmune disease processes, with prompt implementation of safety guidelines for effective management.

On the basis of these encouraging phase 1/2 data, phase 3 studies comparing nivolumab (240 mg intravenously every 2 weeks) as a flat dose or nivolumab plus ipilimumab (1 mg/kg nivolumab and 3 mg/kg ipilimumab intravenously every 3 weeks for two 42-day cycles followed by nivolumab [240 mg intravenously every 2 weeks]) versus placebo as maintenance therapy (in patients without progression) after first-line chemotherapy (CheckMate 451, NCT02538666), and for nivolumab (240 mg every 2 weeks intravenously) versus single-agent chemotherapy as second-line therapy (CheckMate 331, NCT02481830) in SCLC were initiated and are currently ongoing.

Example 2

The phase 1/2 clinical trial detailed in Example 1 has been expanded to include a randomized cohort to further evaluate nivolumab as monotherapy or in combination with ipilimumab in patients with SCLC whose disease progressed after platinum-based therapy. Here, we report an interim descriptive analysis of the SCLC randomized cohort.

Results

Figure 8:
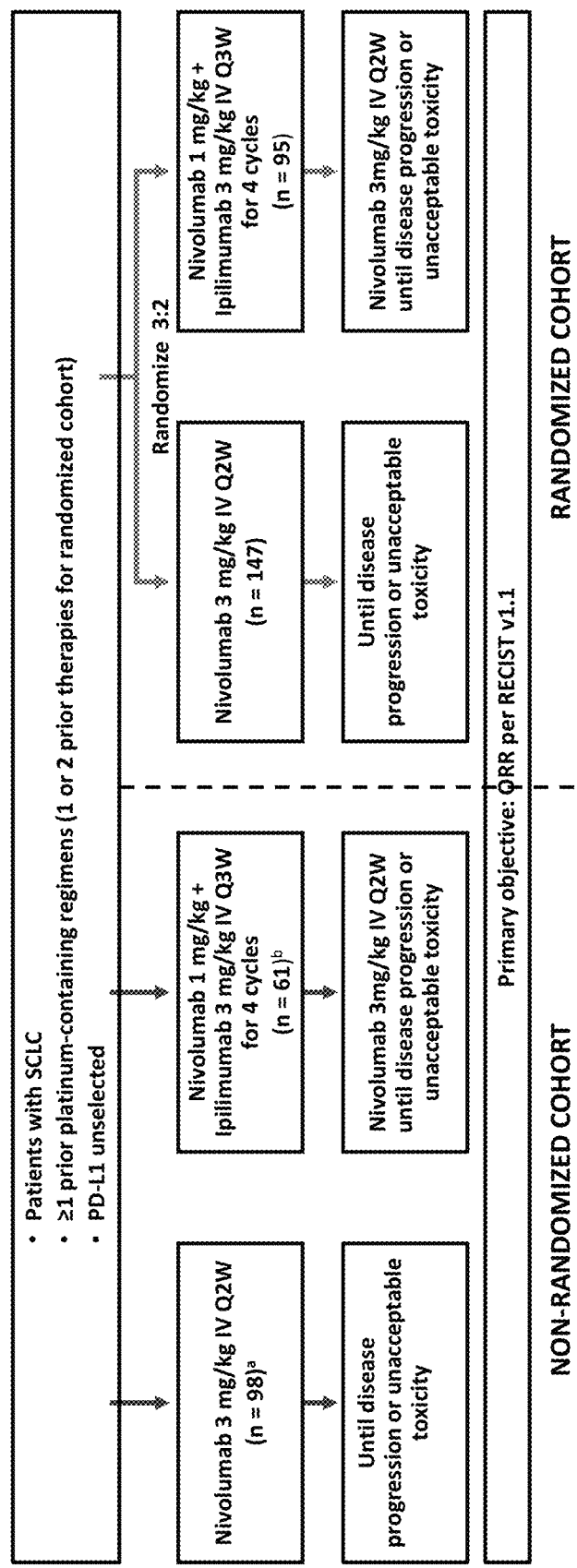
FIG. 8 shows a schematic representation of a study design for treatment of a tumor derived from an SCLC using an anti-PD-1 antibody or a combination of an anti-PD-1 antibody and an anti-CTLA-4 antibody, which includes a randomized cohort and a non-randomized cohort.

Patients with SCLC, having received 1 or 2 prior platinum-containing treatment regimens, were assigned to one of the following treatment groups in the randomized cohort: nivolumab as monotherapy at 3 mg per kilogram of body weight administered intravenously every 2 weeks, or combination treatment of nivolumab plus ipilimumab administered intravenously every 3 weeks for 4 cycles, at nivolumab 1 mg/kg and ipilimumab 3 mg/kg, followed by 3 mg/kg of nivolumab every 2 weeks. A total of 242 patients were randomized 3:2 into the nivolumab monotherapy treatment group (n=147) or the nivolumab and ipilimumab combination therapy treatment group (n=95). See FIG. 8. The primary endpoint of this study was the proportion of patients with a confirmed objective response (defined as the number of patients with a best overall response of complete response or partial response [as per investigator-assessed RECIST, version 1.1 criteria] divided by the number of assigned patients). The objective response rate was the primary endpoint as the trial objective was to evaluate antitumor activity of nivolumab monotherapy or in combination with ipilimumab. Median follow-up for the nivolumab 3 mg/kg group was 10.8 months and was 11.2 months for the nivolumab 1 mg/kg plus ipilimumab 3 mg/kg group.

Baseline characteristics for patients in the randomized cohort are shown in Table 11; all patients in this cohort had been treated with 1 or 2 previous platinum-containing regimens.

TABLE 11

Advanced SCLC baseline patient characteristics-randomized cohort

|  | (n = 147) | (n = 95) |
|---|---|---|
| Median age, years (range) | 63.0 (29ge, | 65.0 (41ge, |
| ≥edian age, | 44 | 51 |
| Male, % | 59 | 63 |
| Prior treatment regimens, % | 67 | 67 |
| 1 | 33 | 33 |
| 2-r |  |  |
| Platinum sensitivity, % | 50 | 42 |
| Sensitive | 49 | 57 |
| Resistant | 1 | 1 |
| Unknown/not reported |  |  |
| Smoking status, % | 92 | 95 |
| Current/former smoker | 7 | 4 |
| Never-smoker | 1 | 1 |
| Unknown |  |  |
| ECOG performance status, % | 33 | 28 |
| 0 | 67 | 71 |
| 1 | 0 | 1 |
| Not reported |  |  |

Figure 10:
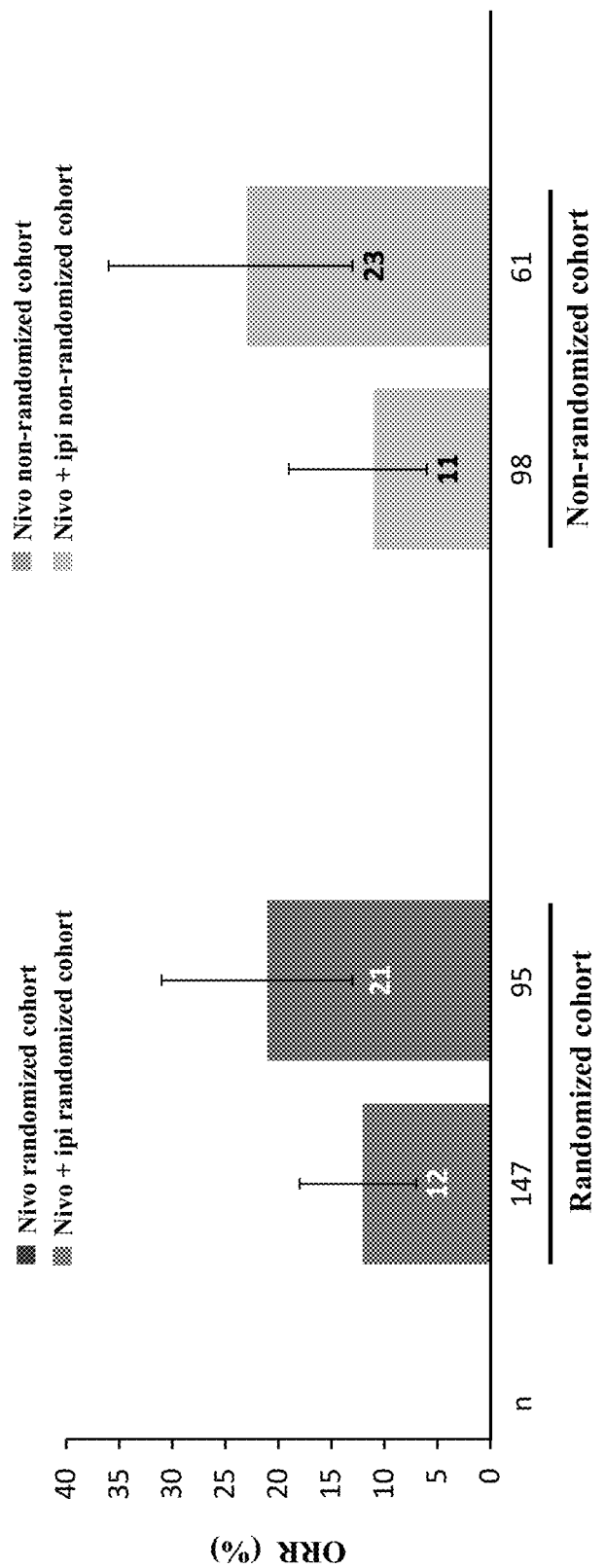
FIG. 10 provides a graphical representation of the overall response rate (ORR) observed in patients treated with nivolumab 1 mg/kg or nivolumab 1 mg/kg plus ipilimumab 3 mg/kg, in the randomized cohort and the non-randomized cohort. Nivo=nivolumab; ipi=ipilimumab.

Complete response (CR) was achieved in 2 patients in the randomized cohort (1 patient in the nivolumab 3 mg/kg group and 1 patient in the nivolumab 1 mg/kg plus ipilimumab 3 mg/kg group). In the randomized cohort, an objective response rate (ORR) of 12% (95% CI) was achieved in the nivolumab 3 mg/kg group, and an ORR of 21% (95% CI) was achieved in the nivolumab 1 mg/kg plus ipilimumab 3 mg/kg group in the randomized cohort; whereas, in the non-randomized cohort, an ORR of 11% (95% CI) was achieved in the nivolumab 3 mg/kg group, and an ORR of 23% (95% CI) was achieved in the nivolumab 1 mg/kg plus ipilimumab 3 mg/kg group. See FIG. 10; Table 9. CIs are as follows: nivolumab (randomized): 7, 18; nivolumab+ipilimumab (randomized): 13, 31; nivolumab (non-randomized): 6, 19; nivolumab+ipilimumab (non-randomized): 13, 36.

The median time to response in the randomized cohort was comparable to that in the non-randomized cohort, i.e., 1.5 months in the nivolumab 3 mg/kg group, and 1.4 months in the nivolumab 1 mg/kg plus ipilimumab 3 mg/kg group.

Figure 11:
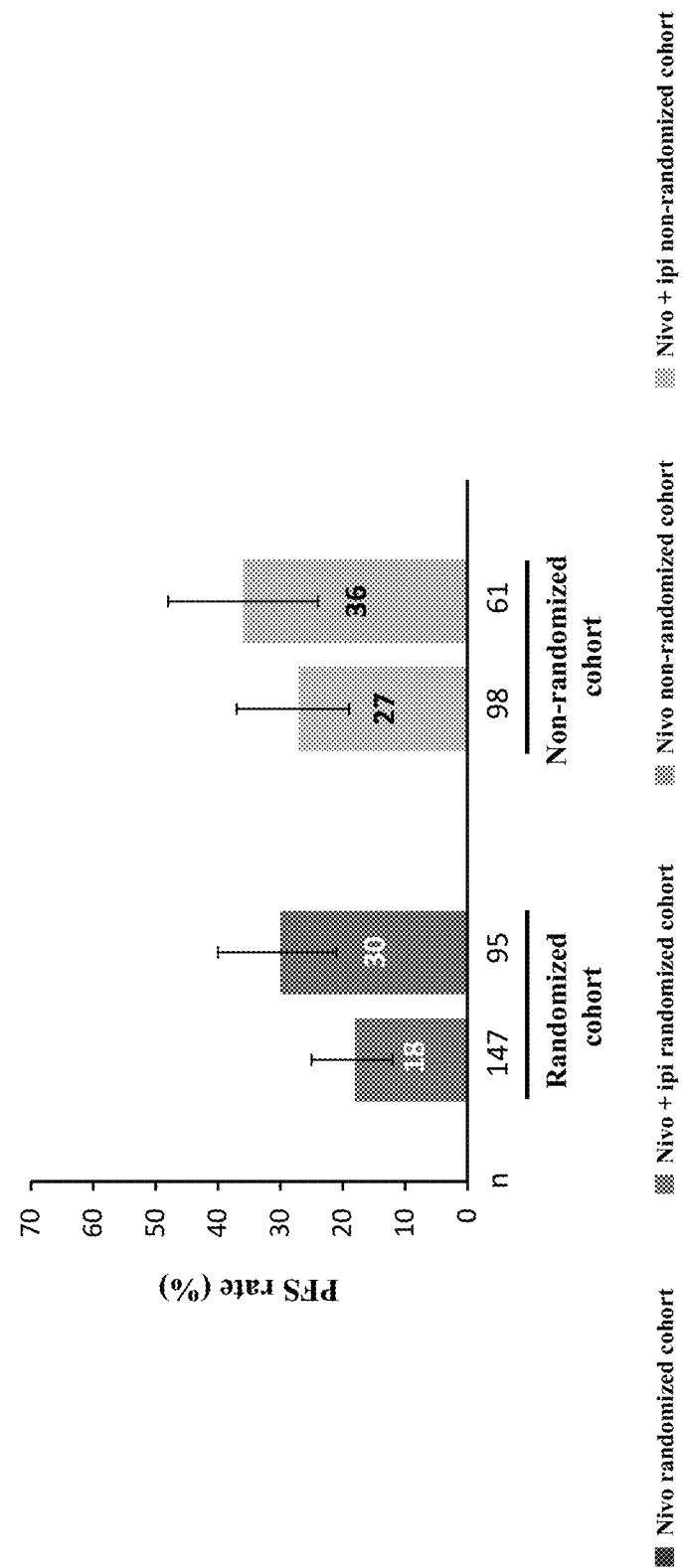
FIG. 11 provides a graphical representation of the rate of progression free survival (PFS) observed in patients treated with nivolumab 3 mg/kg or nivolumab 1 mg/kg plus ipilimumab 3 mg/kg, in the randomized cohort and the non-randomized cohort. Nivo=nivolumab; ipi=ipilimumab.

In the randomized cohort, a progression free survival (PFS) rate of 18% (95% CI) was achieved in the nivolumab 3 mg/kg group, and a PFS rate of 30% (95% CI) was achieved in the nivolumab 1 mg/kg plus ipilimumab 3 mg/kg group in the randomized cohort; whereas, in the non-randomized cohort, a PFS rate of 27% (95% CI) was achieved in the nivolumab 3 mg/kg group, and a PFS rate of 36% (95% CI) was achieved in the nivolumab 1 mg/kg plus ipilimumab 3 mg/kg group. See FIG. 11.

Figure 12:
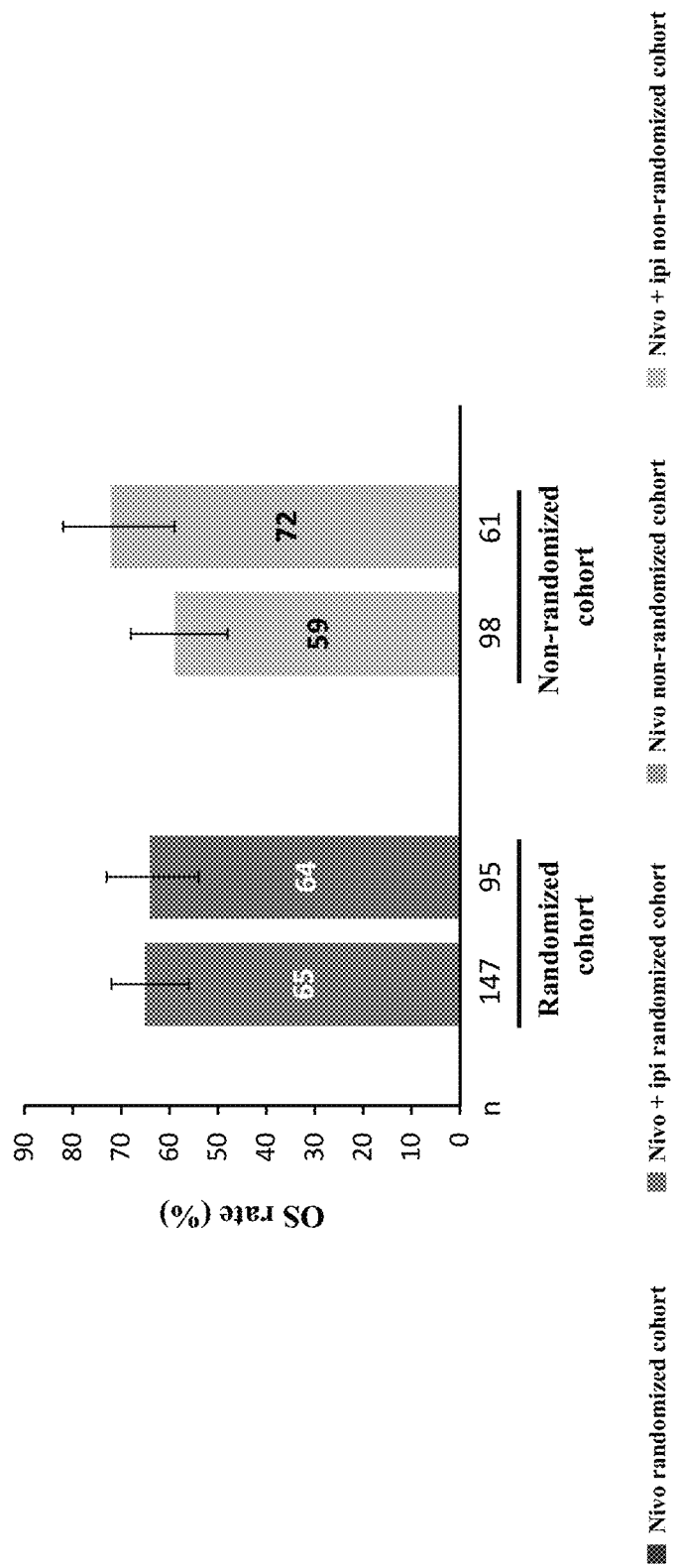
FIG. 12 provides a graphical representation of the overall survival (OS) rate observed in patients treated with nivolumab 3 mg/kg or nivolumab 1 mg/kg plus ipilimumab 3 mg/kg, in the randomized cohort and the non-randomized cohort. Nivo=nivolumab; ipi=ipilimumab.

Overall survival (OS) rate in the randomized cohort was 65% (95% CI) in the nivolumab 3 mg/kg group, and 64% (95% CI) in the nivolumab 1 mg/kg plus ipilimumab 3 mg/kg group; whereas, in the non-randomized cohort, OS was 59% (95% CI) in the nivolumab 3 mg/kg group, and 72% (95% CI) in the nivolumab 1 mg/kg plus ipilimumab 3 mg/kg group. See FIG. 12. The minimum follow-up time was 12 weeks.

Activity and safety of nivolumab monotherapy and nivolumab+ipilimumab combination therapy was also assessed in pooled cohorts, i.e., the nivolumab 3 mg/kg groups from both the randomized cohort and the non-randomized cohort (245 patients combined in the "pooled" nivolumab 3 mg/kg group), and the nivolumab 1 mg/kg+ipilimumab 3 mg/kg groups from both the randomized cohort and the non-randomized cohort (156 patients combined in the "pooled" nivolumab 1 mg/kg+ipilimumab 3 mg/kg group).

The ORR was 11% (95% CI: 8, 6) in the pooled nivolumab 3 mg/kg group, and 22% (95% CI: 16, 29) in the pooled nivolumab 1 mg/kg+ipilimumab 3 mg/kg group. See Table 12.

TABLE 12

ORR in Advanced SCLC by treatment subgroups in pooled cohorts

|  | Nivolumab | | | Nivolumab + Ipilimumab | | |
|---|---|---|---|---|---|---|
|  | n | ORR, % | 95% CI | n | ORR, % | 95% CI |
| Overall population | 245 | 11 | 8, 16 | 156 | 22 | 16, 29 |
| Line of therapy |  |  |  |  |  |  |
| 1 prior therapy | 137 | 12 | 7, 18 | 98 | 19 | 12, 29 |
| 2 or more prior therapies | 108 | 11 | 6, 19 | 58 | 26 | 15, 39 |
| Platinum sensitivity (all treated patients) |  |  |  |  |  |  |
| Platinum-sensitive | 133 | 13 | 8, 20 | 85 | 26 | 17, 36 |
| Platinum-resistant | 110 | 10 | 5, 17 | 65 | 15 | 8, 26 |

Treatment-related adverse events (TRAEs) were assessed in the pooled nivolumab 3 mg/kg group, and the pooled nivolumab 1 mg/kg+ipilimumab 3 mg/kg group. Although TRAEs occurred in 55% of patients in the pooled nivolumab 3 mg/kg group and 73% of patients in the pooled nivolumab 1 mg/kg+ipilimumab 3 mg/kg group, grade 3-4 TRAEs were only observed in 12% of patients in the pooled nivolumab 3 mg/kg group and 37% of patients in the pooled nivolumab 1 mg/kg+ipilimumab 3 mg/kg group. Of those, 78% (31/40 in the pooled nivolumab+ipilimumab group) and 45% (5/11 in the pooled nivolumab group) resolved. Median time to resolution ranged from 1.8 weeks (gastrointestinal events) to 16.3 weeks (hepatic events) in the pooled nivolumab+ipilimumab group, and from 3.4 weeks (pulmonary events) to not reached (renal and hepatic events) in the pooled nivolumab group.

TABLE 13

Safety summary in Advanced SCLC by treatment subgroups in pooled cohorts

|  | Nivolumab (n = 245) | | Nivolumab + Ipilimumab (n = 156) | |
|---|---|---|---|---|
|  | Any grade, % | Grade 3de, % | Any grade, % | Grade 3de, % |
| Any TRAEs | 55 | 12 | 73 | 37 |
| TRAEs leading to discontinuation | 3 | 2 | 13 | 10 |
| Select TRAEs by category |  |  |  |  |
| Skin | 16 | <1 | 36 | 6 |
| Endocrine | 8 | 0 | 21 | 3 |
| Hepatic | 6 | 2 | 12 | 6 |
| Gastrointestinal | 5 | 0 | 24 | 8 |
| Hypersensitivity/infusion reaction | 5 | 0 | 1 | 0 |
| Pulmonary | 3 | 2 | 4 | 3 |
| Renal | 1 | <1 | 1 | 0 |

There were a total of 5 treatment-related deaths, 4 occurring in the pooled nivolumab+ipilimumab group due myasthenia gravis, pneumonitis, seizures/encephalitis, and autoimmune hepatitis (n=1 each) and 1 occurring in the pooled nivolumab group due to pneumonitis. A previously reported death in the nivolumab+ipilimumab group due to renal failure was subsequently determined to not be related to treatment.

Discussion

With a longer follow-up of greater than 2 years, the observed survival and tumor responses to treatment with nivolumab monotherapy or nivolumab and ipilimumab combination therapy remained durable. Efficacy in the randomized cohort was consistent with that observed in the non-randomized cohort. The response to treatment was observed regardless of platinum sensitivity, line of therapy, and/or PD-L1 status.

What is claimed is:

1. A method of treating a subject afflicted with a tumor derived from a small cell lung cancer (SCLC) comprising administering to the subject an antibody or an antigen-binding portion thereof that binds specifically to a Programmed Death-1 (PD-1) receptor and inhibits PD-1 activity ("anti-PD-1 antibody") and an antibody or an antigen-binding portion thereof that binds specifically to Cytotoxic T-Lymphocyte Antigen-4 (CTLA-4) and inhibits CTLA-4 activity ("anti-CTLA-4 antibody")"), wherein the tumor has ≥5% of tumor cells expressing PD-L1, wherein the anti-PD-1 antibody or antigen-binding portion thereof is administered at a flat dose of about 240 mg, about 360 mg, or about 480 mg once about every 2, 3, or 4 weeks, respectively; and wherein the anti-PD-1 antibody or antigen-binding portion thereof comprises nivolumab or pembrolizumab, and the anti-CTLA-4 antibody comprises ipilimumab or tremelimumab.

2. The method of claim 1, wherein the SCLC comprises a small cell carcinoma, a combined small cell carcinoma, or a recurrent SCLC.

3. The method of claim 1, wherein at least one previous line of therapy was administered to treat the tumor.

4. The method of claim 3, wherein the at least one previous line of therapy comprises a chemotherapy, optionally a platinum-based therapy that preferably comprises a platinum-based antineoplastic selected from the group consisting of cisplatin, carboplatin, oxaliplatin, nedaplatin, triplatin tetranitrate, phenanthriplatin, picoplatin, satraplatin, and any combination thereof.

5. The method of claim 1, wherein the anti-PD-1 antibody is nivolumab.

6. The method of claim 1, wherein the anti-CTLA-4 antibody is ipilimumab.

7. The method of claim 1, wherein the anti-CTLA-4 antibody is administered at a dose ranging from about 0.1 mg/kg to about 10.0 mg/kg body weight once about every 1, 2, 3, or 4 weeks.

8. The method of claim 7, wherein
   (i) the anti-CTLA-4 antibody is administered at a dose of about 1 mg/kg body weight once about every 3 weeks; or
   (ii) the anti-CTLA-4 antibody is administered at a dose of about 3 mg/kg body weight once about every 3 weeks.

9. The method of claim 8, wherein the administration of the anti-PD-1 antibody and the anti-CTLA-4 antibody is repeated four times (4 cycles).

10. The method of claim 8, wherein the anti-CTLA-4 antibody is administered at a dose of about 3 mg/kg body weight once about every 3 weeks.

11. The method of claim 1, wherein the subject is further treated with an anti-PD-1 antibody monotherapy following administration of the anti-PD-1 antibody and the anti-CTLA-4 antibody.

12. The method of claim 1, wherein the anti-PD-1 antibody is pembrolizumab.

13. The method of claim 12, wherein the anti-PD-1 antibody is administered at a flat dose of about 360 mg once every 3 weeks.

14. The method of claim 1, wherein the anti-PD-1 antibody is administered at a flat dose of about 240 mg once every 2 weeks.

15. The method of claim 1, wherein the anti-PD-1 antibody is administered at a flat dose of about 480 mg once every 4 weeks.

* * * * *